(12) United States Patent
Cohen-Armon

(10) Patent No.: US 9,486,449 B2
(45) Date of Patent: *Nov. 8, 2016

(54) CANCER THERAPY

(71) Applicant: Malka Cohen-Armon, Tel Aviv (IL)

(72) Inventor: Malka Cohen-Armon, Tel Aviv (IL)

( * ) Notice: Subject to any disclaimer, the term of this patent is extended or adjusted under 35 U.S.C. 154(b) by 45 days.

This patent is subject to a terminal disclaimer.

(21) Appl. No.: 14/246,403

(22) Filed: Apr. 7, 2014

(65) Prior Publication Data

US 2014/0303201 A1    Oct. 9, 2014

Related U.S. Application Data

(63) Continuation-in-part of application No. 12/756,714, filed on Apr. 8, 2010, now Pat. No. 8,729,080, which is a continuation-in-part of application No. PCT/IL2008/001075, filed on Aug. 5, 2008.

(60) Provisional application No. 60/960,666, filed on Oct. 9, 2007.

(51) Int. Cl.
| | | |
|---|---|---|
| *A01N 43/42* | (2006.01) | |
| *A61K 31/44* | (2006.01) | |
| *A61K 31/4743* | (2006.01) | |
| *A61K 31/473* | (2006.01) | |
| *A61K 45/06* | (2006.01) | |

(52) U.S. Cl.
CPC ......... *A61K 31/4743* (2013.01); *A61K 31/473* (2013.01); *A61K 45/06* (2013.01)

(58) Field of Classification Search
CPC . A61K 31/4743; A61K 31/473; A61K 45/06
USPC ................................. 514/291, 298
See application file for complete search history.

(56) References Cited

U.S. PATENT DOCUMENTS

| | | | |
|---|---|---|---|
| 6,121,278 A | 9/2000 | Jackson et al. | |
| 6,277,990 B1 | 8/2001 | Jagtap et al. | |
| 6,476,048 B1 | 11/2002 | Szabo et al. | |
| 6,531,464 B1 | 3/2003 | Szabo et al. | |
| 6,723,733 B2 | 4/2004 | Li et al. | |
| 6,989,388 B2 | 1/2006 | Pellicciari et al. | |
| 7,825,129 B2 | 11/2010 | Pellicciari et al. | |
| 2004/0126755 A1* | 7/2004 | Stephan ............... | C12Q 1/6886 435/6.14 |
| 2004/0265286 A1 | 12/2004 | Desnoyers | |
| 2009/0170860 A1 | 7/2009 | Scotto et al. | |
| 2010/0284964 A1 | 11/2010 | Cohen-Armon | |

FOREIGN PATENT DOCUMENTS

| | | |
|---|---|---|
| CA | 2725911 A1 | 12/2009 |
| WO | 01/42219 A2 | 6/2001 |
| WO | 02/36599 A1 | 5/2002 |
| WO | 2006/039545 A2 | 4/2006 |
| WO | 2007/062413 A2 | 5/2007 |
| WO | 2009047752 A1 | 4/2009 |

OTHER PUBLICATIONS

Ali-Osman (Brain Tumors, Ed. Ali-Osman, p. 359-381).*
Castiel A, Visochek L, Mittelman L., Dantzer F, Izraeli S, Cohen-Armon M. 2011. A small molecule exclusively eradicates human cancer cells: Extra-centrosomes de-clustering agent BMC Cancer 11(1):412.
Godinho SA, Kwon M, Pellman D. 2009. Centrosomes and cancer: how cancer cells divide with too many cetrosomes. Canc Met Rev 28:85-98.
Kwon M, Godunov SA, Chandhok NS, Ganem NJ, Azioune A, Thery M and Pellman D. 2008, Mechanisms to suppress multipolar division in cancer cells with extra centrosomes Gene Dev 22: 2189-2203.
Inbar-Rozensal D., Visochek L., Castel D., Castiel A., Izraeli S., Dantzer F. and Cohen-Armon M. 2009 A selective eradication of human nonhereditary breast cancer cells by phenanthridine-derived polyADP-ribose polymerase inhibitors. Breast CancerRes. 11(6):R78.
Frizzell, KM, W Lee Kraus WL. 2009. PARP inhibitors and treatment of breast cancer: beyond BRCA1/2? Breast Cancer Research, 11:111.
Bryant HE, Schultz N, Thomas HD, Parker KM, Flower D, Lopez E, Kyle S, Meuth M, Curtin NJ, Helleday T: Specific killing of BRCA2-deficient tumours with inhibitors of poly(ADP-ribose) polymerase. Nature 2005, 434: 913-917.
Fong P.C., Boss D.S., YapT.A., Tutt A., Wu P., et al., 2009. Inhibition of Poly(ADP-Ribose)Polymerase in Tumors from BRCA Mutation Carriers. The New Eng. J. Med. 361: 123-134.
Kanai M, Tong WM, Wang ZQ, Miwa M. 2007. Haploinsufficiency of poly(ADP-ribose) polymerase-1-mediated poly (ADP-ribosyl)ation for centrosome duplication. Blochem Biophys Res Commun. 359:426-430.
Wahlberg E., Karlberg T., Kouznetsova E., Markova N., Macchiarulo A., Thorsell A-G., et al., 2012, Family-wide chemical profiling and structural analysis of PARP and tankyrase inhibitors Nature Biotechnology 30: 283-288.
Jagtap P, Soriano FG, Virág L, Liaudet L, Mabley J, Szabó E, Haskió G, Marton A, Lorigados CB, Gallyas F Jr, Sümegi B, Hoyt DG, Baloglu E, VanDuzer J, Salzman AL, Southan GJ, Szabó C. 2002. Novel phananthridine inhibitors of poly(adenosine 5'-diphosphate-ribose)synthetase: Potent cytoprotective and antishock agents. Crit. Care Med. 30: 1071-1082.
Levy EM, Roberti MP and Mordoh J. 2011. Natural Killer Cells in Human Cancer: From Biological Functions to Clinical Applications. J. Biomed Biotechnol 2011:676198. doi:10.1155/2011/676198.
International Search Report in PCT/IL2008/001075.
IPER and Written Opinion (Form PCT/ISA/237) in PCT/IL2008/001075.
Tentori and Graziani "Chemopotentiation by PARP inhibitors in cancer therapy," Pharmacological Research 52: 25-33(2005).
Graziani and Szabó, "Clinical perspectives of PARP inhibitors," Pharmacological Research 52: 109-118 (2005).
Bryant et al., "Specific killing of BRCA2-deficient tumours with inhibitors of poly(ADP-ribose) polymerase," Nature 434: 913-917 (2005).

(Continued)

*Primary Examiner* — Uma Ramachandran
(74) *Attorney, Agent, or Firm* — Browdy and Neimark, PLLC

(57) ABSTRACT

The subject invention provides for cancer therapy.

9 Claims, 41 Drawing Sheets

(56) References Cited

OTHER PUBLICATIONS

Farmer et al., "Targeting the DNA repari defect in BRCA mutant cells as a therapeutic strategy," Nature 434: 917-921 (2005).
De Soto and Deng, "PARP-1 inhibitors: are they the long-sought genetically specific drigs for BRCA 1/2—associated breast cancers?" Int. J. Med. Sci, 3: 117-123 (2006).
Pellicciari et al., "Towards new neuroprotective agents: design and synthesis of 4H-thieno[2,3-c] isoquinolin-5-one derivatives as potent PARP-1 inhibitors," Farmaco 58: 851-858 (2003).
Chiarugi et al., "Novel Isoquinolinone—Deroved Inhibitors of Poly(ADP-ribose) Polymerase-1: Pharmacological Characterization and Neuroprotective Effects in an in Vitro Model ofCerebral Ischemia," J. Pharmacol. Exp. Ther. 305, 943-949 (2003).
Banasik et al., Specific Inhibitors of Poly(ADP-Ribose) Synthetase and Mono(ADP-Ribosyl)transferase: J. Biol. Chem. 267: 1569-1575 (1992).
Weltin et al., "Immunosuppressive activities of 6(5H)-Phenanthridinone, a new poly(ADP-rebose)Polymerase inhibitor" Int. J. Immunopharmacol. 17: 265-271 (1995).
Weltin et al., "Effect of 6(5H)-phenanthridinone, a ploy (ADP-ribose)polymerase inhibitor, and ionizing radiation on the growth of cultured lymphoma cells" Int. J. Radiat. Biol. 72(6): 685-692(1997).
Cookson et al., "Peroxynitrite and Hydrogen Peroxide induced cell death in the NSC34 Neuroblastoma X Spinal Cord cell line: role of poly(ADP-ribose) polymerase" J. Neurochem. 70: 501-508 (1998).
Richardson et al., "Effects of PARP inhibition on drug and FAS-induced apoptosis in leukaemic cells," Adv. Exp. Med. Biol. 457: 267-279 (1999).
Bernges and Zeller, "Combination effects of poly(ADP-ribose) polymerase inhibitors and DNA-damaging agents in ovarian tumor cells lines—with special reference to cisplatin" J. Cancer Res. Clin. Oncol. 122: 665-670 (1996).
Pacher et al., "Pharmacologic inhibition of poly(adenosine diphosphate-ribose) polymerase may represent a novel therapeutic approach in chronic heart failure" J. Am. Coll. Cardiol. 40(5): 1006-1009 (2002).
Cohen-Armon et al., "DNA-independent PARP-1 Activation by Phosphorylated ERK2 Increases Elk1 activity: a link to histone acetylation" Mol Cell 25: 297-308 (2007).
Homburg et al., "A fast signal-induced activation of poly(ADP-ribose)polymerase: a novel downstream target of phospholipase C" J. Cell Biol. 150: 293-308 (2000).
Visochek et al., "PolyADP-ribosylation is involved in neurotrophic activity" J. Neurosci. 25(32): 7420-7428 (2005).
Abdelkarim et al., "Protective effects of PJ34, a novel, potent inhibitor of poly(ADP-ribose) Polymerase (PARP) in in vitro and in vivo models of stroke" International Journal Molecular Medicine 7: 255-260 (2001).
Park et al., "Interaction between inducible nitric oxide synthase and ploy(ADP-ribose) polymerase in focal ischemic brian injury" Stroke—J. Am Heart Assn, 35: 2896-2901 (2004).
Cepeda et al., "Poly(ADP-ribose) polymerase-1 (PARP-1) inhibitors in cancer chemotherapy" Recent Patents on Anti-Cancer Drug Discovery 1: 39-53 (2006).
Weltin et al., "N-Acetylcysteine protects lymphocytes from nitrogen mustard-induced apoptosis" Biochemical Pharmacology 51: 1123-1129 (1996).
Curtin, "PARP inhibitors for cancer therapy" Expert Rev Mol Med. 7(4):1-20 (2005).
Godinho et al., "Centrosomes and cancer: how cancer cells divide with too many centrosomes" Cancer Metastasis Rev 28: 85-98 (2009).
Cohen-Armon, "PARP-1 activation in the ERK signaling pathway" Trends in pharmacological sciences 28(11): 556-60 (2007).
Lamoral-Theys et al., "Lycorine, the main phenanthridine Amaryllidaceae alkaloid, exhibits significant antitumor activity in cancer cells that display resistance to proapoptotic stimuli: an investigation of structure-activity relationship and mechanistic insight" J Med. Chemistry 52(20): 6244-6256 (2009).
Inbar-Rozensal et al., "A selective eradication of human nonhereditary breast cancer cells by phenanthridine-derived polyADP-ribose polymerase inhibitors" Breast Cancer Research 11: R78 (2009).
Chevanne et al., "Inhibition of PARP Activity by PJ-34 leads to growth impairment and cell death associated with aberrant mitotic pattern and nucleolar actin accumulation in M14 melanoma cell line" J Cell Physiol.; 222(2):401-10 (2010).
Zaremba et al., "PARP Inhibitor Development for Systemic Cancer Targeting" Anti-Cancer Agents in Medicinal Chemistry 7: 515-523 (2007).
Tutt et al., "Mutation in BRCA1 and BRCA2 results in profound sensitivity to small molecule inhibitors of PARP—A potential novel therapeutic strategy for familial breast cancer" Abstracts—Poster Session IV, S181: XP-002501035.
Wang et al., "Haploinsufficiency of PARP1 accelerates BRCA1—associated centrosome emplification, telomere shortening, genetic instability, apoptosis, and embryonic lethality" Cell Death and Differentiation 14: 924-931 (2007).
Chiarugi et al., "Novel Isoquinolinone-derived inhibitors of poly(ADP-ribose) Polymerase-1: pharmacological characterization and neuroprotective effects in an in vitro model of cerebral ischemia" J Pharm and Experimental Therapeutics 305(3): 943-949 (2003).
Szijarto et al., "Effect of Pj-34 Parp-Inhibitor on rat liver microcirculation and antioxidant status" J of Surgical Research 142: 72-80 (2007).
Ferraris et al., "Design and synthesis of poly(ADP-ribose) Polymerase-1 (PARP) inhibitors. Part 4: Biological Evaluation of Imidazobenzodiazepines as potent PARP-1 inhibitors for treatment of ischemic injuries" Bioorganic & Medicinal Chemistry 11: 3695-3707 (2003).
Rajesh et al., "Poly(ADP-ribose)polymerase inhibition decreases angiogenesis" Biochemical and Biophysical Communications 350: 1056-1062, (2006).
Castiel A., Visochek L., Mittelman L., Zilberstein Y., Dantzer F., Izraeli S., Cohen-Armon M. 2013, Confocal imaging of live cancer cells harboring extra-centrosomes in mitosis, JoVE (Journal of Visualized Experiments) in press.
Chang P, Coughlin M and Mitchison TJ. 2005. Tankyrase-1 polymerization of poly(ADP-ribose) is required for spindle structure and function, Nature Cell Biol. 7, 1133-1139.
Weltin et al., Effect of 6(5H)-phenanthridinone, an inhibitor of poly(ADP-ribose) polymerase, on cultured tumor cells, Oncology Research, 6(9):399-403 (1994).
Krämer et al., Mechanisms and Consequences 3 of Centrosome Clustering in Cancer Cells, The Cenrosome, Chapter 17 pp. 1-23 (2012).

\* cited by examiner

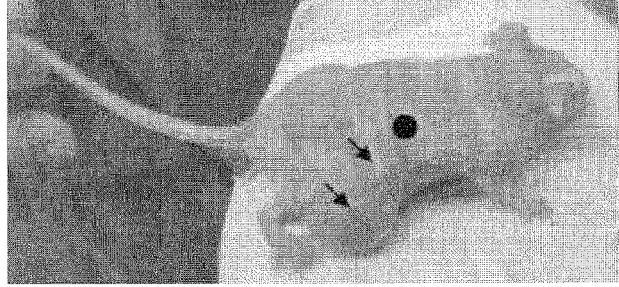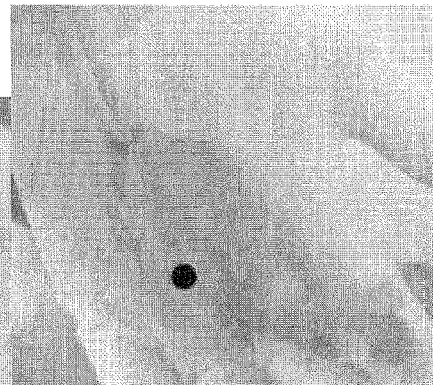
FIG. 6A  FIG. 6B
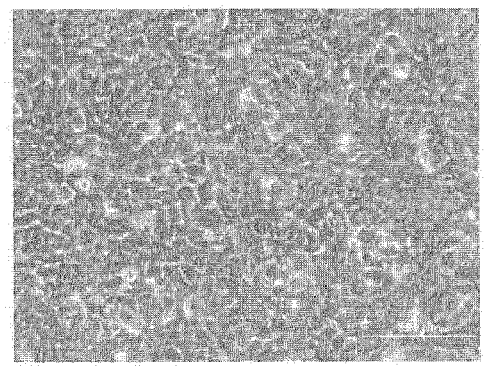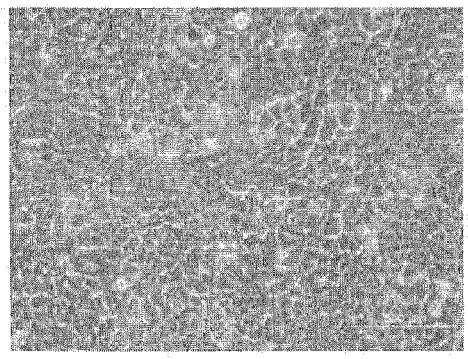
FIG. 7A  FIG. 7B

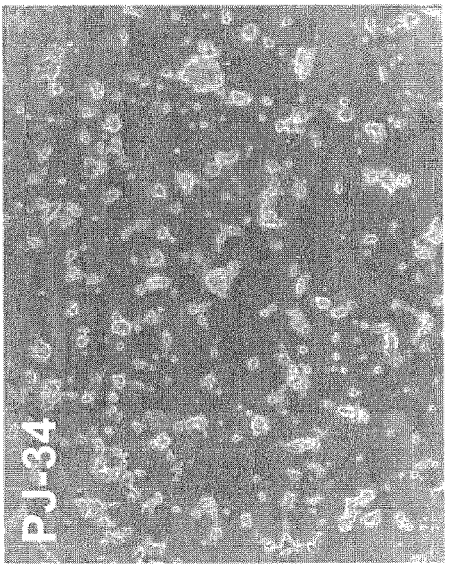
FIG. 11A-II
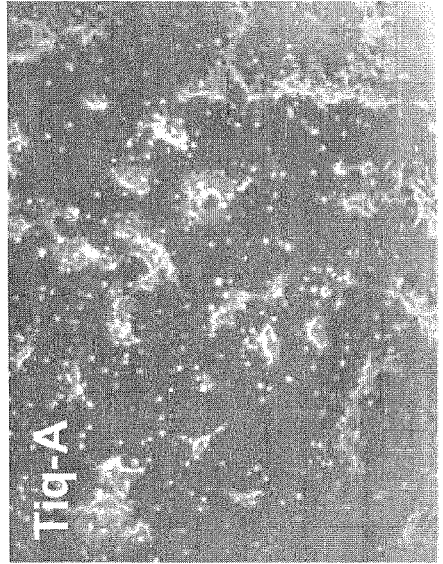
FIG. 11A-IV
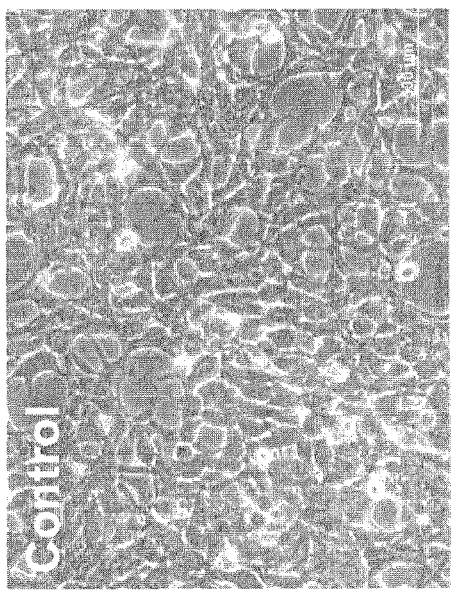
FIG. 11A-I
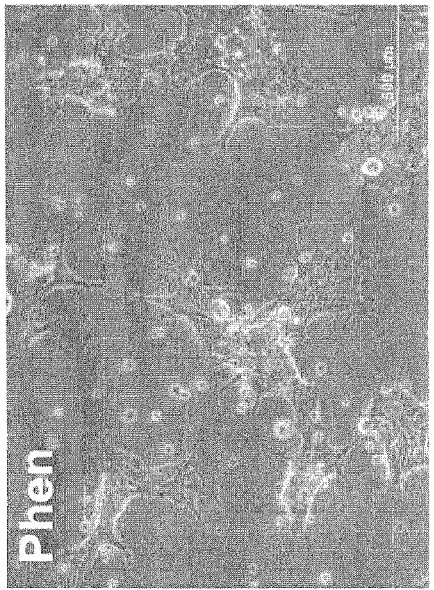
FIG. 11A-III

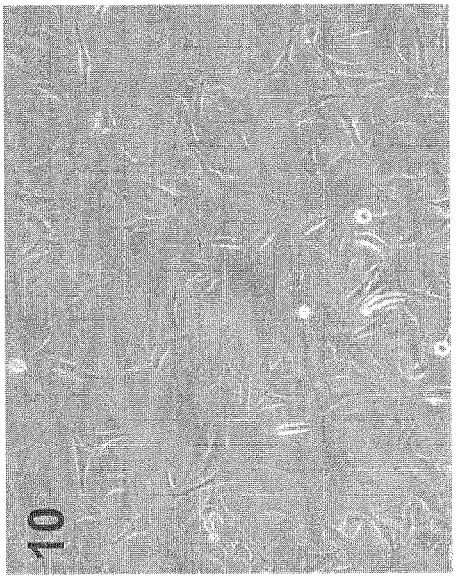
FIG. 11D-II
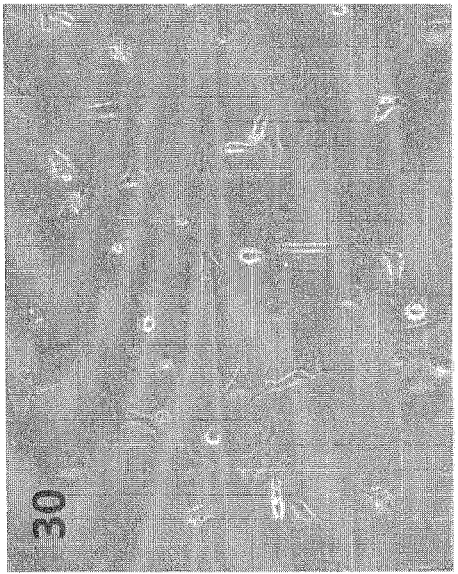
FIG. 11D-IV
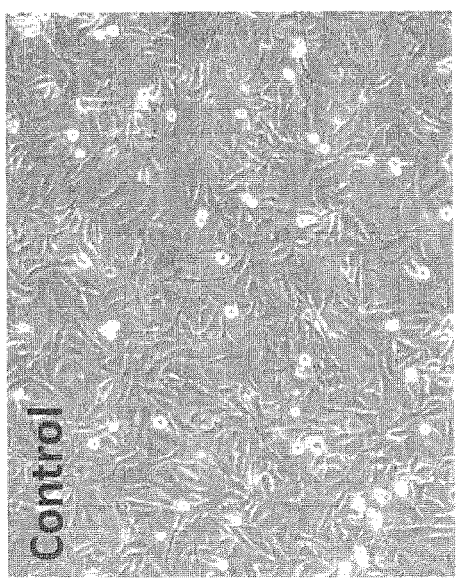
FIG. 11D-I
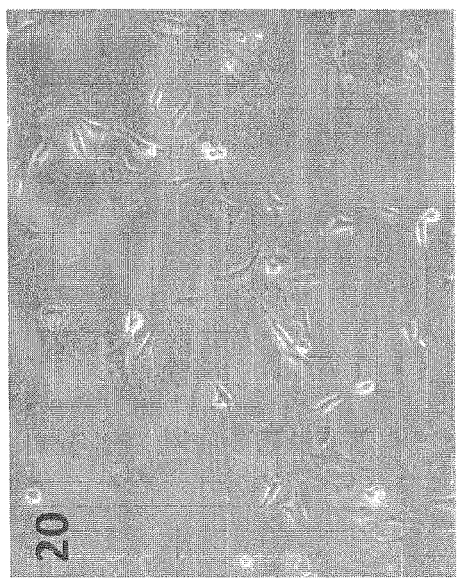
FIG. 11D-III

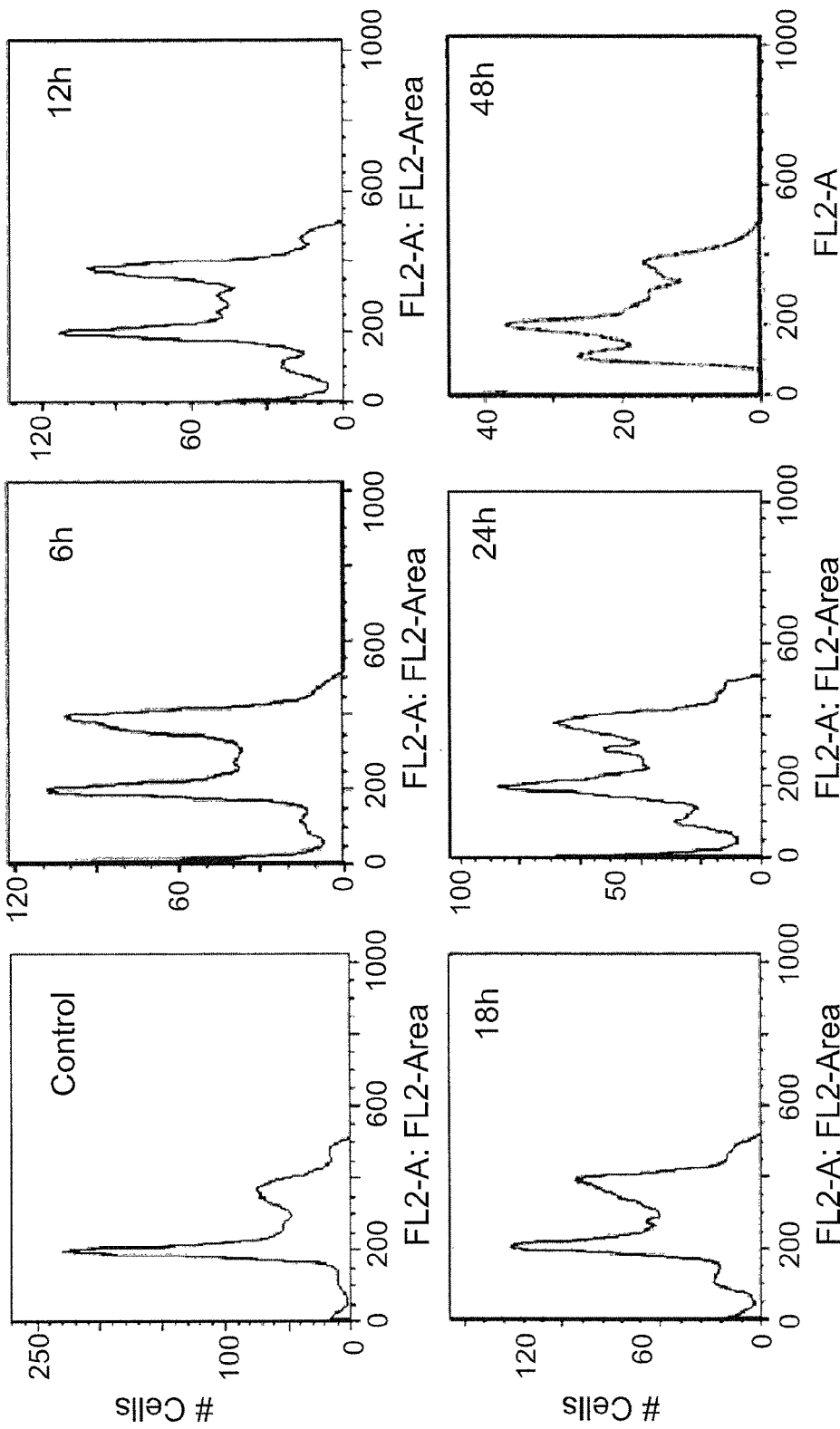

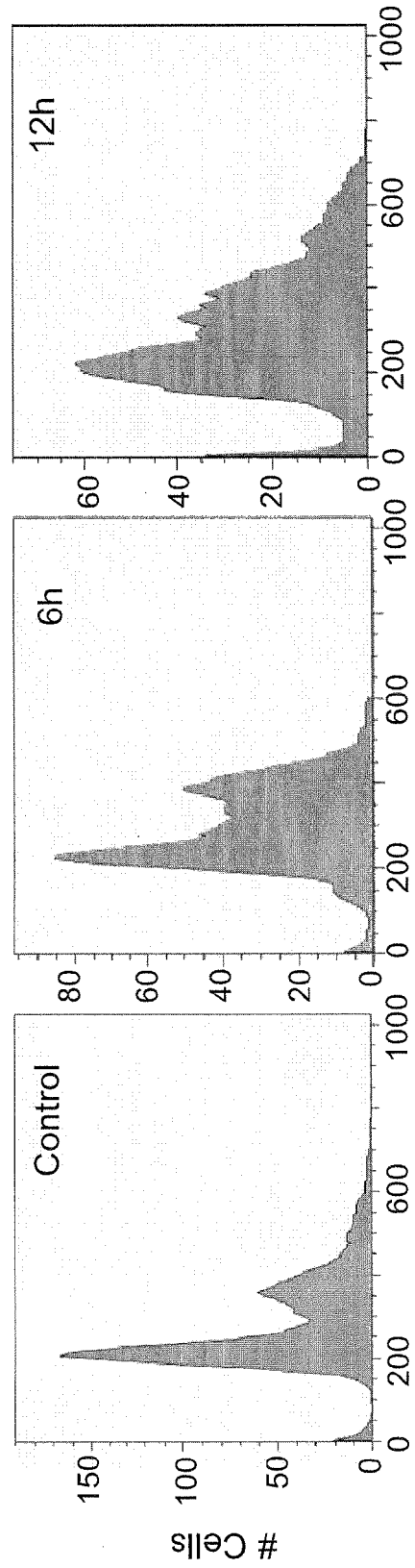
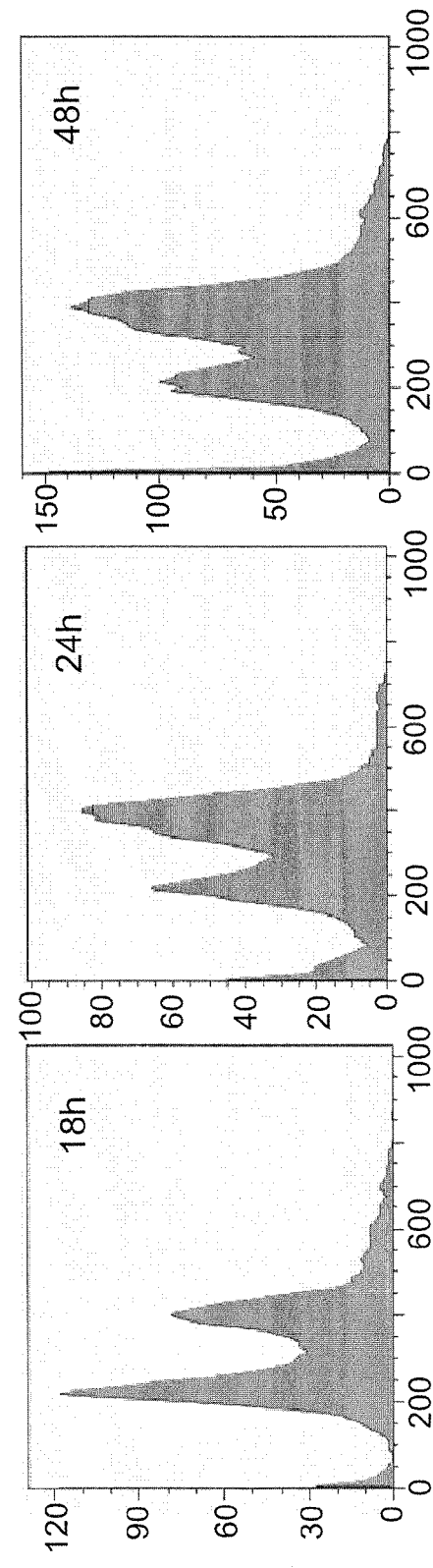
FIG. 12G　FIG. 12H　FIG. 12I
FIG. 12J　FIG. 12K　FIG. 12L

FIG. 13A-I 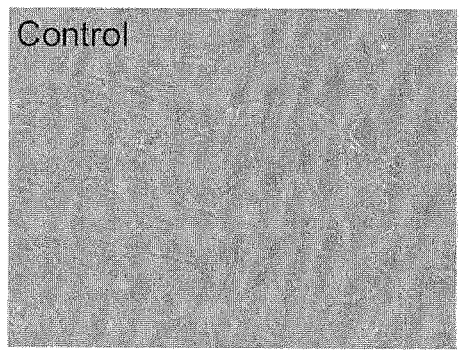 FIG. 13A-II 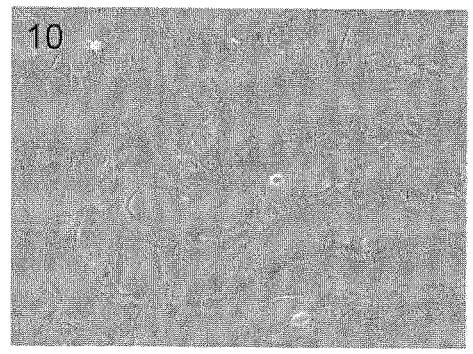
FIG. 13A-III 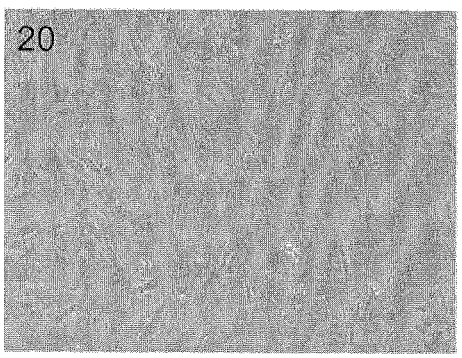 FIG. 13A-IV 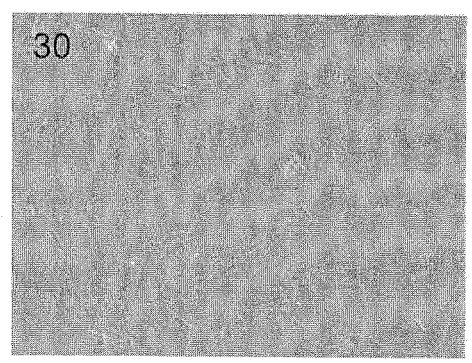
FIG. 13A-V  FIG. 13A-VI 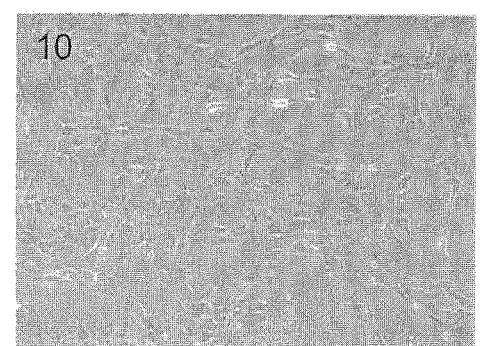

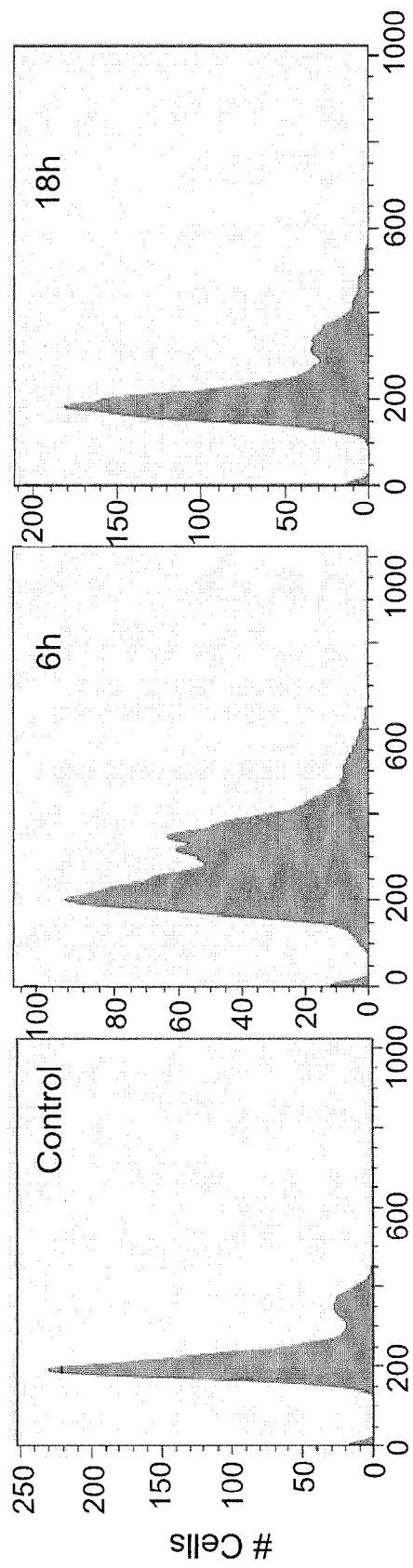
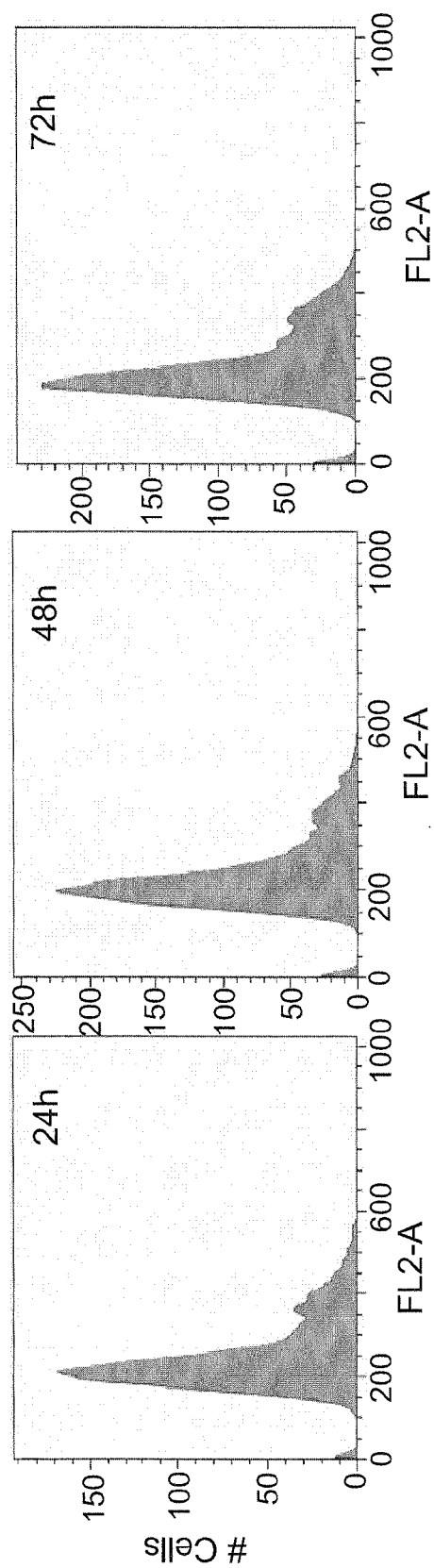
FIG. 13B-I  FIG. 13B-II  FIG. 13B-III
FIG. 13B-IV  FIG. 13B-V  FIG. 13B-VI

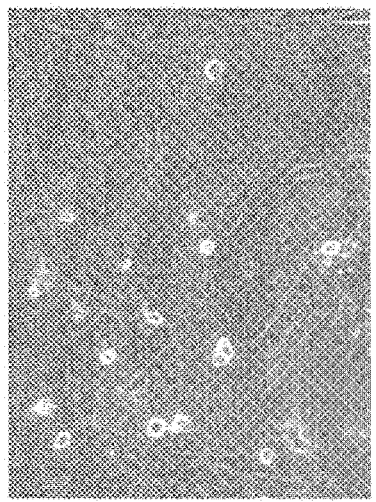
FIG. 14A-II
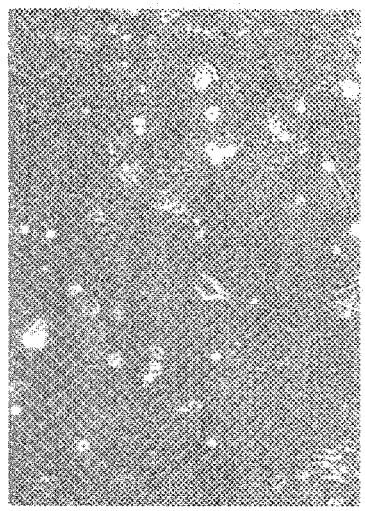
FIG. 14A-IV
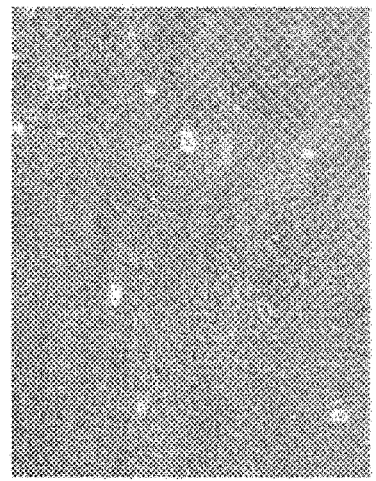
FIG. 14A-I
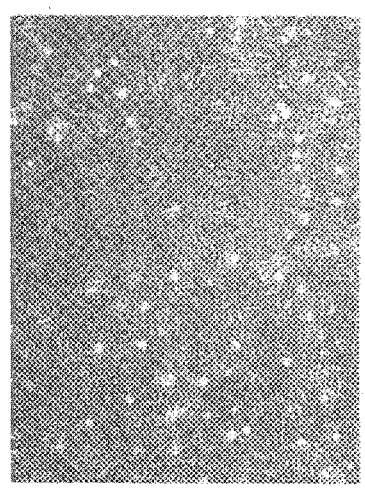
FIG. 14A-III

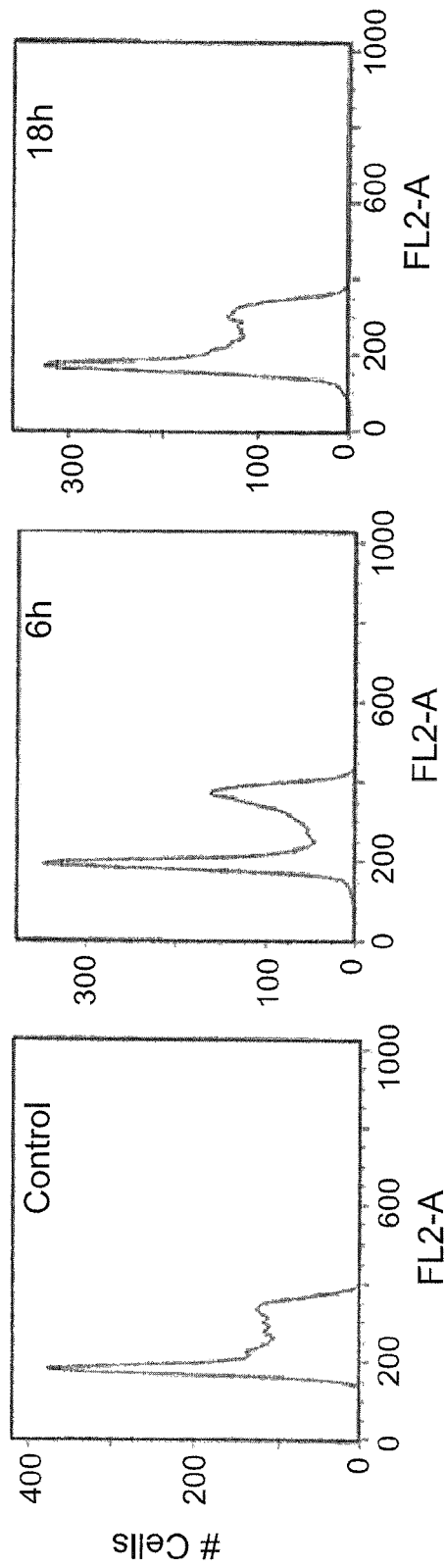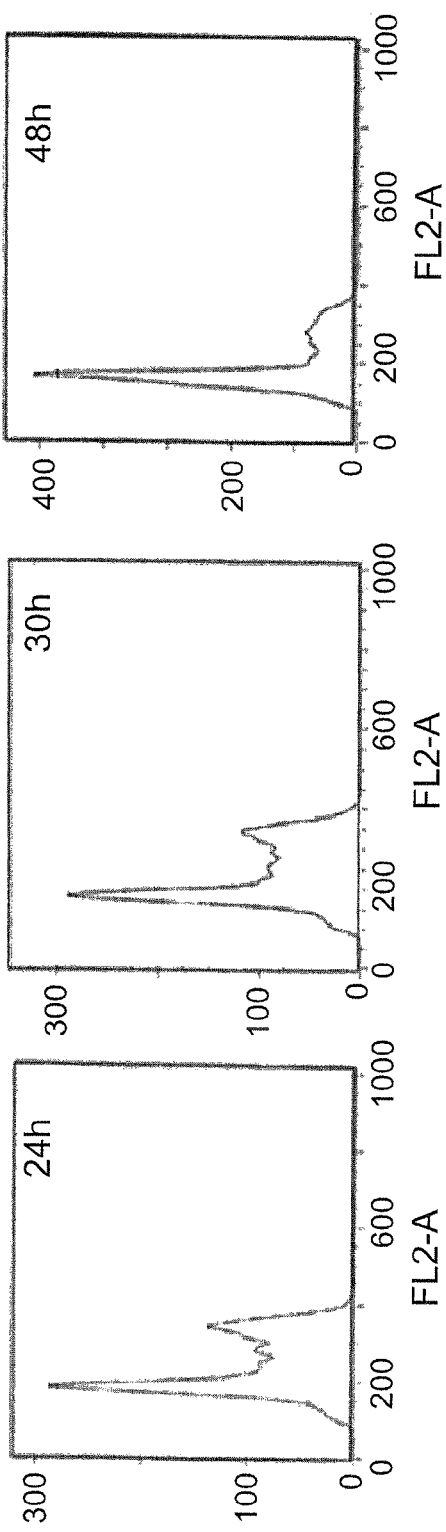

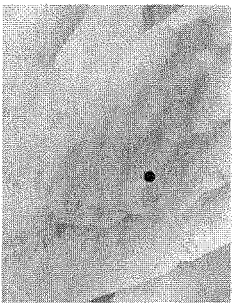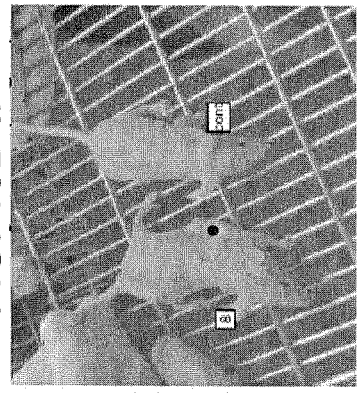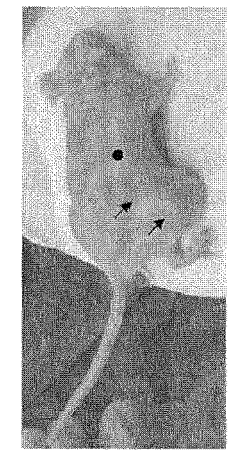
FIG. 15A-II
FIG. 15B-II
FIG. 15A-I
FIG. 15B-I

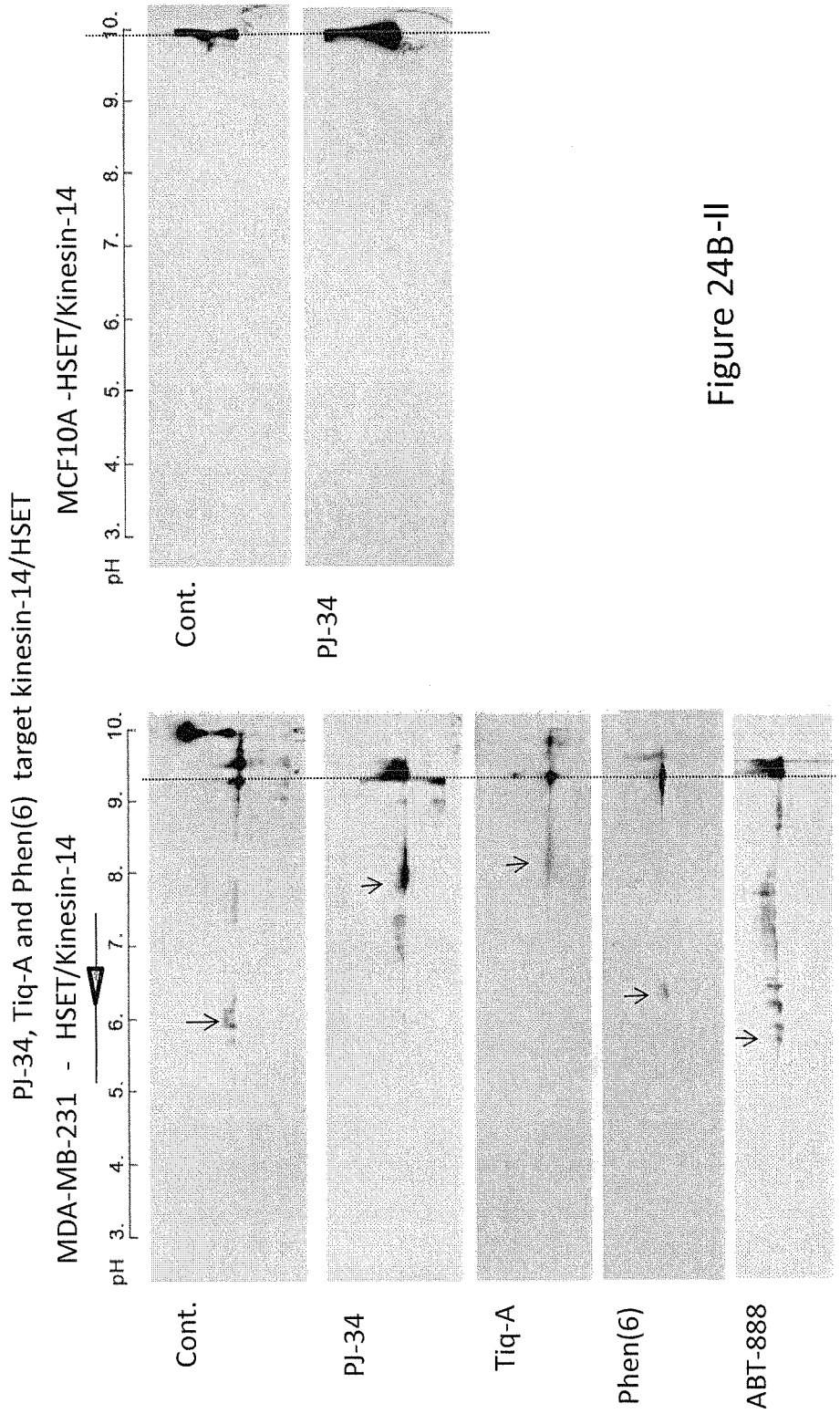
Figure 24B-II
Figure 24B-I

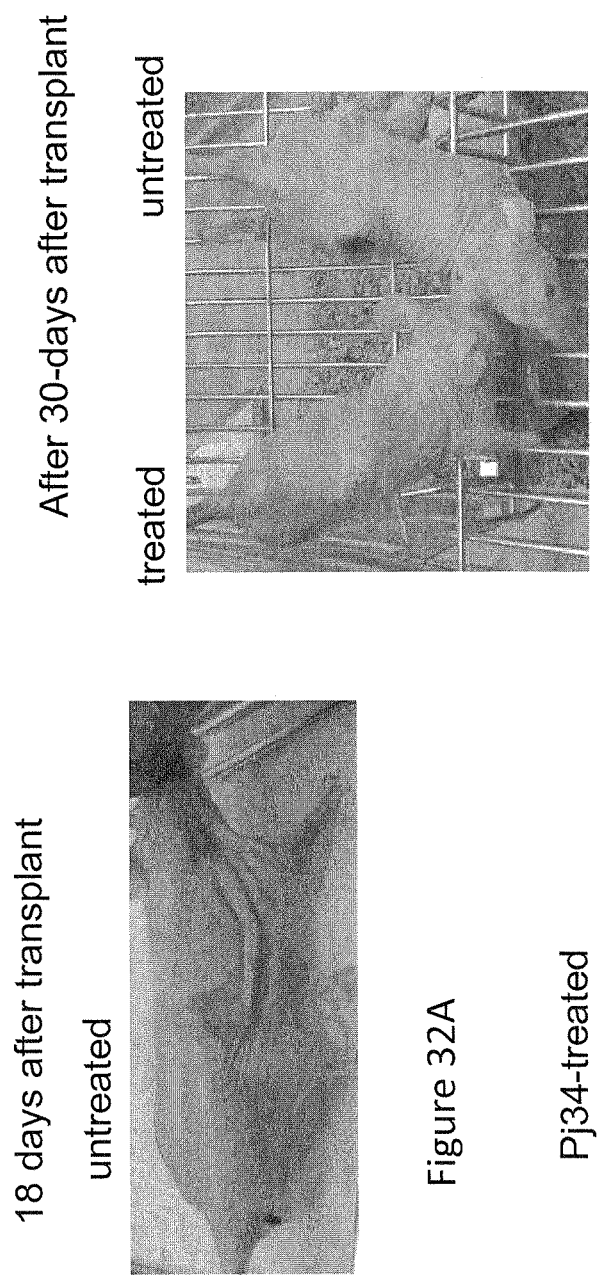
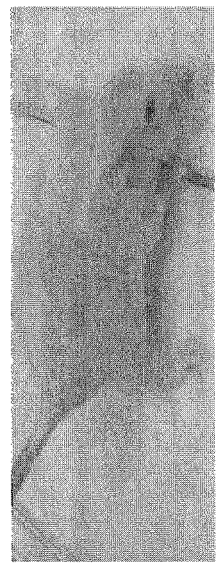
Figure 32A
Figure 32B
Figure 32C

CANCER THERAPY

FIELD OF THE INVENTION

This invention relates to the field of cancer therapy.

BACKGROUND OF THE INVENTION

Cancer is a class of diseases in which a group of cells display uncontrolled growth, invasion and sometimes metastasis. Cancer affects people at all ages with the risk for most types increasing with age. Cancer causes about 13% of all human deaths.

Breast cancer is the leading cause of cancer in women and the second cause for women's mortality. Only 5-10% of the most abundantly occurring human breast cancers are familial breast cancers, induced by deficiencies and mutations of the tumor suppressor genes brca1 and brca2. All other human breast cancers are not induced by mutations of the tumor suppressor genes brca1 and brca2.

Tentori et al., *Pharmacological research* 52: 25-33 (2005) and Graziani et al. *Pharmacological research* 52: 109-118 (2005) review the use of several poly (ADP-ribose) polymerase (PARP) inhibitors (also named poly (ADP-ribose) synthetases and poly (ADP-ribose) transferases) in contributing to the treatment of cancer in combination with cytotoxic drugs.

Bryant et al., *Nature* 434, 913-917 (2005) and Farmer et al., *Nature* 434, 917-921 (2005) demonstrate that certain PARP inhibitors (such as AG14361) kill brca1 and brca2 deficient malignant cancer cells without affecting wild-type MCF-7 breast cancer cells. According to Bryant et al., supra, the sensitivity to the PARP inhibitor appears to be a direct consequence of the brca2 defect. Bryant et al., supra, further show that the survival of MCF7 cancer cells was reduced with PARP inhibitors only when brca2 was depleted from these cells.

In addition, De Soto et al., *Int. J. Med. Sci*, 3, 117-123 (2006) reviewed several papers showing, apart from the findings in Bryant et al., supra, and Farmer et al., supra, that CAPANI cells (which are deficient in brca2) were not inhibited by certain PARP inhibitors (such as NU1025), but were inhibited by other PARP inhibitors (such as KU0058684). Also, Bryant et al., supra, showed that only 50% MCF-7 brca1+/+ cells were eradicated by exposure for 10 consecutive days to the potent PARP inhibitor AG14361 (10 µM).

Pellicciari et al., (2003), *Farmaco* 58, 851 and Chiarugi et al. (2003), *J. Pharmacol. Exp. Ther.* 305, 943 describe the PARP-1 inhibitor Tiq-A (4H-thieno[2,3-c]isoquinolin-5-one) and its potential as neuroprotective agent.

M. Banasik, et al., *J. Biol. Chem.* 267, 1569 (1992) describe the PARP inhibitor Phen (6(5H)-phenanthridinone). D. Weltin, et al., *Int. J. Immunopharmacol.* 17, 265 (1995) describe immunological properties of Phen; D. Weltin, et al., *Int. J. Radiat. Biol.* 72, 685 (1997) describe the ability of Phen to increase radiation induced inhibition of cell proliferation. M. R. Cookson, et al, *J. Neurochem.* 70, 501 (1998) describe that Phen prevented cell death induced by hydrogen peroxide or peroxynitrite. D. S. Richardson, et al.; *Adv. Exp. Med. Biol.* 457, 267 (1999) describe that pretreatment with Phen and 3-aminobenzamide (3AB) in HL-60 myeloid leukemia cell lines resulted in resistance to apoptotic death rather than potentiation thereof.

F. Bernges & W. J. Zeller, *J. Cancer Res. Clin. Oncol.* 122, 665 (1996) describe that the PARP inhibitor 3-AB had no effect on the cytotoxicity of cisplatin.

WO 01/42219 discloses the PARP inhibitor PJ-34 (N-(6-oxo-5,6-dihydro-phenanthridin-2-yl)-N,N-dimethylacetamide, HCl) as a compound protecting against neuronal cell death induced by stroke or inflammation.

Tentori et al., supra, describes PJ-34 and its protective effects against cardiac dysfunction.

Pacher et al., (2002) *J. Am. Coll. Cardiol.* 40, 1006-1009 injected PJ-34 in rodents for a 10 week period to diminish cardiomyocytes cell death after cardiac stroke and to avoid chronic heart disease.

Cohen-Armon M. et al., (2007) *Mol Cell* 25, 297-308; Homburg et al., (2000) *J. Cell Biol.* 150:293-308; Visochek et al., (2005) *J. Neurosci.* 25:7420-742 describe that the survival of non-dividing cells, such as brain cortical neurons or cardiomyocytes is not affected following treatment with PJ-34.

Abdelkarim et al., (2001) *Int. J. Mol. Med*, 7, 255-260 and Park et al., (2004) *Stroke*, 35, 2896-2901 describe the neuroprotective effect of PJ-34 after stroke both in vivo and in vitro.

Inbar-Rozendal et al., (2009) *Breast Cancer Research* 11: R78 describe selective eradication of human nonhereditary breast cancer cells by phenanthridine-derived polyADP-ribose polymerase inhibitors.

Castiel A. et al., (2011) *Cancer* 11(1):412A discloses small molecule exclusively eradicates human cancer cells: Extra-centrosomes de-clustering agent BMC.

Castiel A. and Malka Cohen-Armon (2013) *Journal of Visualized Experiments* (*JoVE*) disclose cell death associated with abnormal mitosis observed by confocal imaging in live and fixed cancer cells.

SUMMARY OF THE INVENTION

It has now been found that phenanthridine derivatives of general formula (I), including the compounds N-(6-oxo-5,6-dihydro-phenanthridin-2-yl)-N,N-dimethylacetamide, salts thereof and particularly HCl salt thereof (referred to herein as PJ-34), 6-(5H)-phenanthridinone (referred to herein as Phen) and its salts, and 4H-thieno[2,3-c]isoquinolin-5-one (referred to herein as Tiq A) and its salts, are effective in the treatment and/or prevention of cancer, have lethal effects on cancer cells, both in vitro and in vivo, in particular on breast cancer, lung cancer, pancreatic cancer, ovary cancer, colon cancer and leukemia.

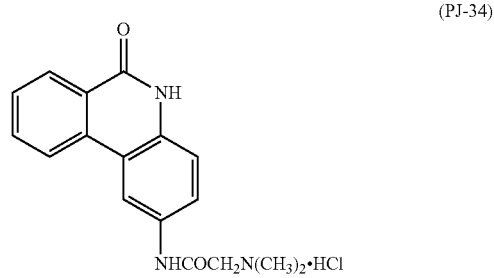

(PJ-34)

The compounds used in accordance with the invention were found effective against human cancer cells, which underwent mitotic catastrophe cell death, as compared to normal cells that were found unaffected. Thus, the invention is further directed at the treatment of cancers which are characterized by high occurrence of multi-centrosomal cells.

The invention thus provides a method for de-clustering multi-centrosomes and for distorting the spindles in cancer cells during mitosis, the method comprising contacting said cell with at least one compound as disclosed herein. In some embodiments, the compound is one or more of PJ-34, Tiq-A and Phen. In some embodiments, the compound is PJ-34.

As noted hereinbelow, the activity of each of the compounds is not attributed to PARP-1 inhibition but to a different mechanism, which is not shared by other PARP-1 inhibitors. For this reason, for example, PJ-34, Tiq-A and Phen eradicate non-brca cancer cells that are not eradicated by other even more potent PARP1 inhibitors.

Moreover, the activity of PJ-34 was independent on the presence of PARP-1.

The compounds used in accordance with the invention act on the human kinesin-14 (HSET), one of the proteins responsible for extra-centrosomes clustering in human cancer cells. The compounds were found to affect post-translation modification of HSET in human cancer cells (e.g., MDA-MB-231 cells, A549 Lung cancer cell-line and U87 glioblastoma cell-line), with no similar effect on HSET in human normal cells (e.g., epithelial cells MCA10A). In addition, or as a consequence of HSET modification block, PJ-34 was found to interfere with the binding of HSET to alpha-tubulin and gamma-tubulin. Thus, the invention further provides a method for deactivating function of HSET, causing distorted and short spindles and preventing bi-focal extra-centrosomes clustering (causing de-clustering of extra-centrosomes in human cancer cells).

The invention further provides use of a compound, as defined herein, e.g., PJ-34, Phen and Tiq-A, as HSET inhibitors. In some embodiments, the HSET inhibition is inhibition of HSET interaction with tubulin.

As used herein, the inhibition of HSET causes at least one or more of arresting, diminishing, minimizing or preventing interaction between HSET and tubulin; arresting, diminishing, minimizing or preventing proper spindle assembly; and arresting, diminishing, minimizing or preventing stable spindle poles. A person versed in the art would understand that although HSET is dispensable in non-transformed human cells, it is essential for bipolar spindle formation in mitosis of human cancer cells, and its function is crucial for their cell division and survival. The acentrosomal organization mediated by HSET is required for bipolar spindle formation in cancer cells, irrespective of the presence and number of normal or supernumerary centrosome. When cells are contacted (e.g., incubated) with a compound used herein, HSET deactivation ensues, causing damage to spindle assembly and pole-focusing with the end result of having the spindle poles fragment into multipolar spindles. As such, the ability of compounds such as those utilized in accordance with the invention in interrupting HSET activity, as defined, causes eradication of cancer cells.

The expression "arresting, diminishing, minimizing or preventing" refers to the ability of a compound as disclosed to interrupt or inhibit HSET activity to an extent which the interaction between HSET and tubulin, and/or spindle assembly, and/or pole focusing are stopped or minimized or otherwise affected to an extent that cell division does not occur or is not possible or cell death ensues. The activity of compounds as disclosed herein to achieving any one or more of the above may be measured and quantified as detailed and demonstrated herein.

Thus, the method of the invention also concerns the use of compounds of formula (I) such as PJ-34, Tiq-A and Phen, which were found to have a lethal effect on human breast cancer cells, such as MDA-MB-231 and MCF-7, on human lung cancer cells H1299 and A549, on human pancreas cancer cells PANC1, on human ovarian cancer cells HeyAB and skoV3, on human colon cancer cells DLD-1 and human glioblastoma brain cancer and human lymphoid leukemia REH, while not impairing normal dividing cells as human epithelial cells MCF-10A or Huvec endothelial cells and human mesenchymal cells, in a method of treatment of cancer.

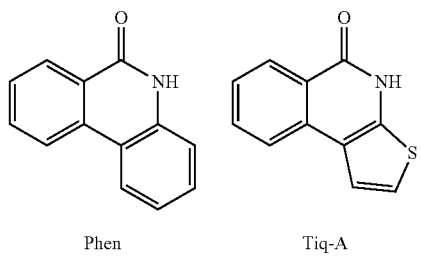

Phen            Tiq-A

In another aspect, the present invention provides a method of treating and/or preventing cancer in a subject, the method comprising administering to the subject at least one compound of the general formula (I), or a pharmaceutically acceptable salt thereof:

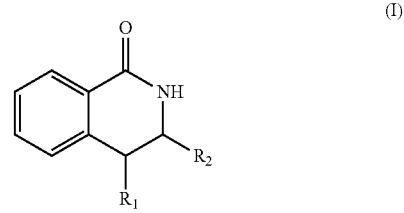

(I)

wherein $R_1$ and $R_2$ together with the carbon atoms to which they are bonded form a 5 or 6 membered aromatic or hetero-aromatic ring, optionally substituted by at least one group selected from amino, formamido, alkyl substituted amido, amine substituted amido, and alkyl amino substituted amido.

In some embodiments, the compound of formula (I) is a compound selected from the group consisting of N-(6-oxo-5,6-dihydro-phenanthridin-2-yl)-N,N-dimethylacetamide, 4H-thieno[2,3-c]isoquinolin-5-one (Tiq-A), and 6-(5H)-phenanthridinone (Phen) or any pharmaceutically acceptable salt thereof or any combination of the aforesaid compounds and/or salts thereof. In some embodiments, the compound of formula (I) is N-(6-oxo-5,6-dihydro-phenanthridin-2-yl)-N,N-dimethylacetamide HCl (PJ-34).

In another aspect, the invention provides a pharmaceutical composition comprising a compound of the general formula (I), or a pharmaceutically acceptable salt thereof:

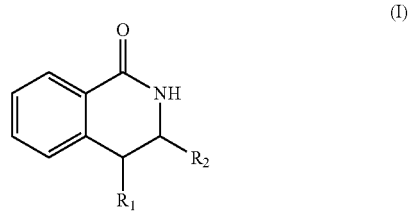

(I)

wherein $R_1$ and $R_2$ together with the carbon atoms to which they are bonded form a 5 or 6 membered aromatic or hetero-aromatic ring, optionally substituted by at least one group selected from amino, formamido, alkyl substituted amido, amine substituted amido, alkyl amino substituted amido or any salts thereof and a pharmaceutically acceptable carrier for use in the treatment or prevention of cancer.

It has also been found that the compound PJ-34 (N-(6-oxo-5,6-dihydro-phenanthridin-2-yl)-N,N-dimethylacetamide, HCl) has a lethal effect on breast cancer cells, both in vitro and in vivo, in particular on breast cancer MCF-7 and MDA-MB-231. MCF-7 and MDA-MB-231 breast cancer cells are not deficient, depleted or mutated with respect to brca1 or brca2.

(PJ-34)

It has further been found that each of the compounds Tiq-A (4H-thieno[2,3-c]isoquinolin-5-one) and Phen (6-(5H)-phenanthridinone) also have a lethal effect on breast cancer cells, in particular on breast cancer MCF-7 and MDA-MB-231.

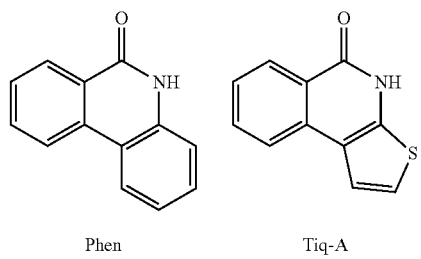

Phen    Tiq-A

In another aspect, the present invention thus provides a use of a compound of the general formula (I), or a pharmaceutically acceptable salt thereof:

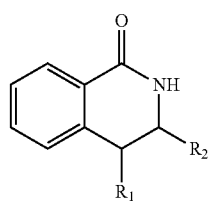

(I)

wherein $R_1$ and $R_2$ together with the carbon atoms to which they are bonded form a 5 or 6 membered aromatic or hetero-aromatic ring, optionally substituted by at least one group selected from amino, formamido, alkyl substituted amido, amine substituted amido, alkyl amino substituted amido or any salts thereof for the preparation of a medicament to treat or prevent cancer.

The subject invention further provides a use of a compound selected from the group consisting of N-(6-oxo-5,6-dihydro-phenanthridin-2-yl)-N,N-dimethylacetamide HCl (PJ-34), 4H-thieno[2,3-c]isoquinolin-5-one (Tiq-A), and 6(5H)-phenanthridinone (Phen) or combinations thereof for the preparation of a medicament to treat or prevent cancer.

In a further aspect, the invention provides a method for the treatment or prevention of a disease in a subject, said method comprising administering to said subject a compound of the general formula (I), as defined herein, in combination with at least one agent selected from the group consisting of a chemotherapeutic agent, a cytotoxic agent, a cytostatic agent, an immunological modifier, an interferon, an interleukin, a MEK inhibitor, an anti-progestogen agent, a cytokine, folic acid, a vitamin, a mineral and any combination thereof.

In some embodiments, the disease is a proliferative disease, e.g., cancer as defined herein. In some embodiments, said at least one agent is at least one MEK inhibitor.

BRIEF DESCRIPTION OF THE DRAWINGS

FIG. 1

Survival rate (%) of MCF-7 breast cancer cells after incubation for 48 hours upon exposure to several concentrations of PJ-34 applied only once 24 hours after seeding.

FIG. 3

Survival rate (%) of MCF-7 breast cancer cells reseeded and incubated for two weeks in PJ-34-free medium, after 48 hours exposure to a single application of several concentrations of PJ-34 applied 24 hours after initial seeding.

FIG. 4

Figure 4A:
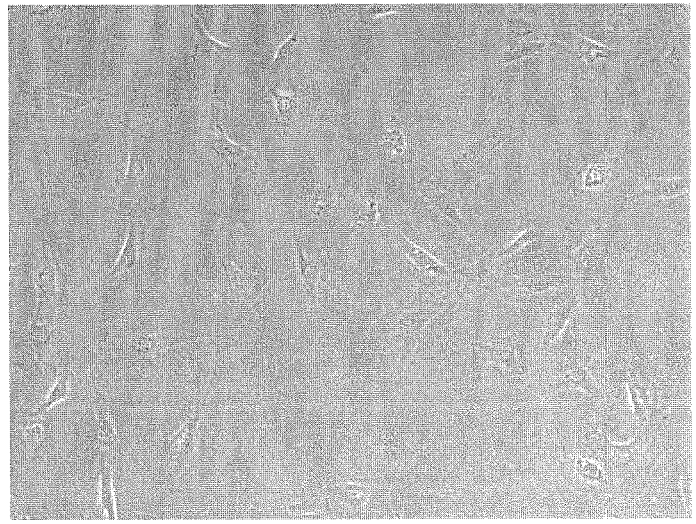

FIG. 4A: Fibroblast cell proliferation (control) 12 hours after seeding.

Figure 4B:
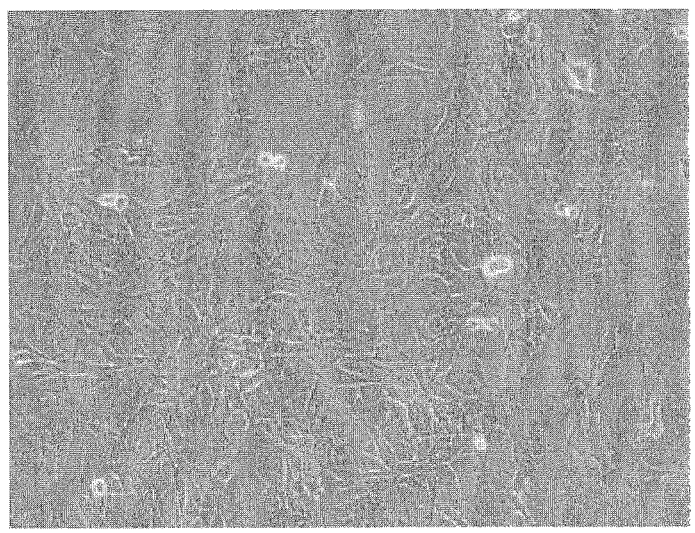

FIG. 4B: Fibroblast cell proliferation (control) 72 hours after seeding.

Figure 4C:
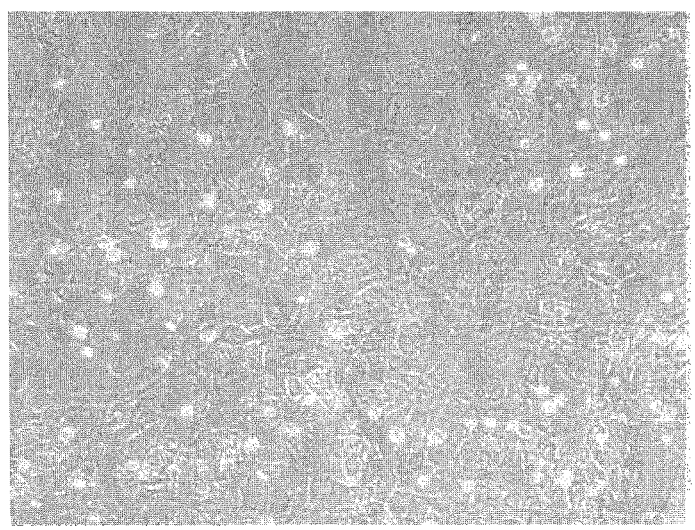

FIG. 4C: Fibroblast cell proliferation (control) 170 hours after seeding.

Figure 4D:
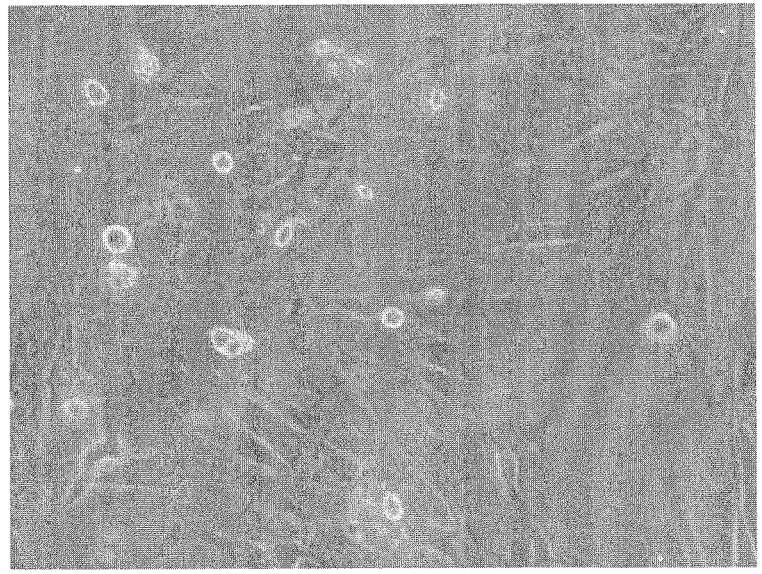

FIG. 4D: Fibroblast cell proliferation in the presence of 10 μM PJ-34 (applied 24 hours after seeding) after 72 hours.

Figure 4E:
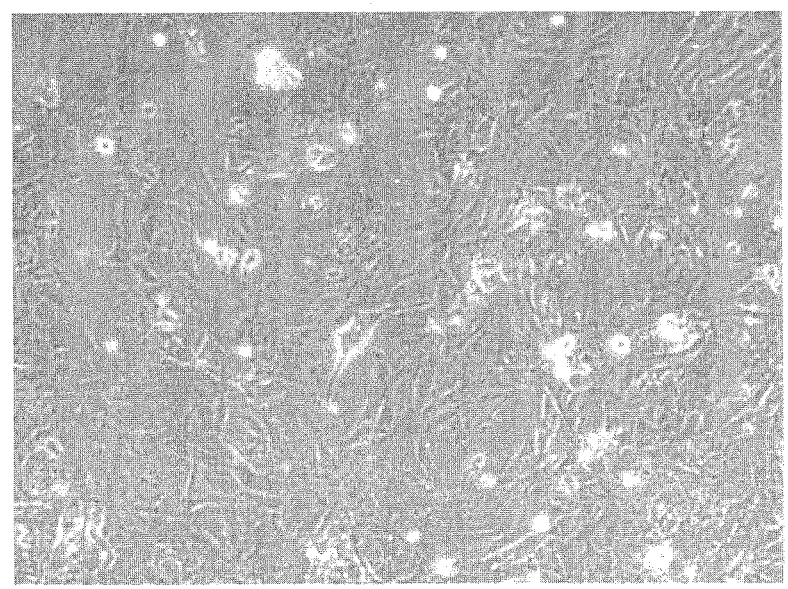

FIG. 4E: Fibroblast cell proliferation in the presence of 20 μM PJ-34 (10 μM PJ-34 applied twice, 24 hours and 72 hours after seeding) after 170 hours.

FIG. 5

Survival rate (cells per field) of fibroblasts after repeated exposure to PJ-34 as indicated by the arrows.

FIG. 6

Xenotransplants of MCF-7 established in female CD-1 nu/nu mice (n=6).

FIG. 6A: Three mice not treated with PJ-34 developed tumors (labeled by arrows).

FIG. 6B: Three mice treated with PJ-34 did not develop tumors.

FIG. 7

FIG. 7A: MCF-7 breast cancer cells (control).

FIG. 7B: MCF-7 breast cancer cells in medium containing 0.1% DMSO (control).

FIG. 8

Figure 8C:
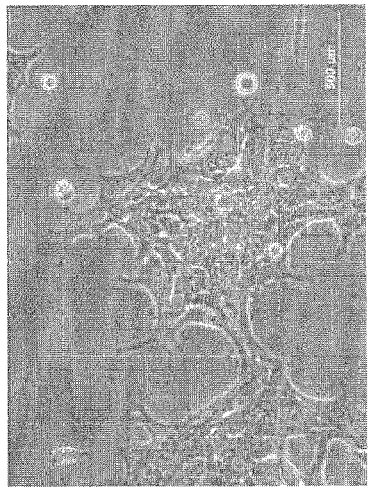
Figure 8F:
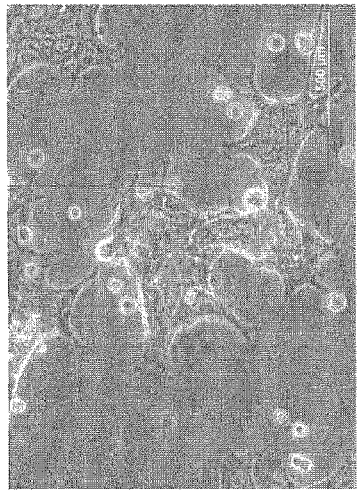
Figure 8B:
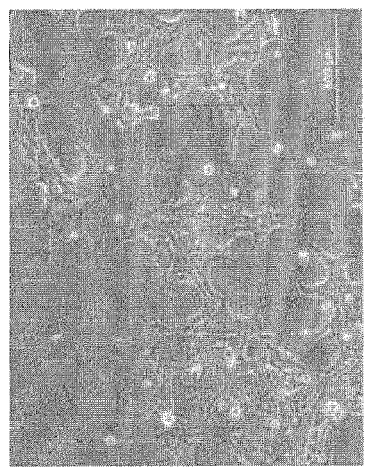
Figure 8E:
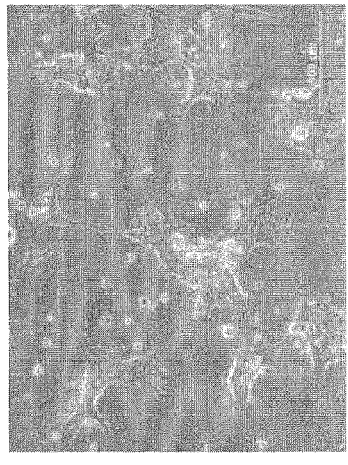
Figure 8A:

FIGS. 8A, 8B and 8C: MCF-7 breast cancer cells incubated for 72 hours after a single application of Tiq-A at a concentrations of 50 μM applied 24 hours after seeding.

Figure 8D:
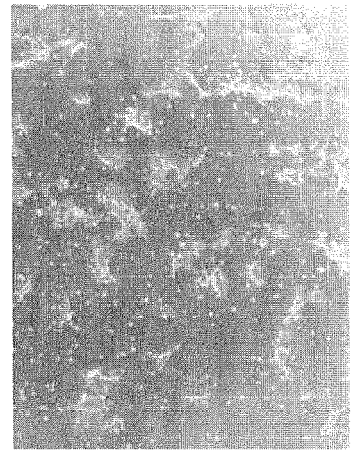

FIGS. 8D, 8E and 8F: MCF-7 breast cancer cells incubated for 72 hours after a single application of Tiq-A at a concentrations of 100 μM applied 24 hours after seeding.

FIG. 9

Figures 9A, 9B:
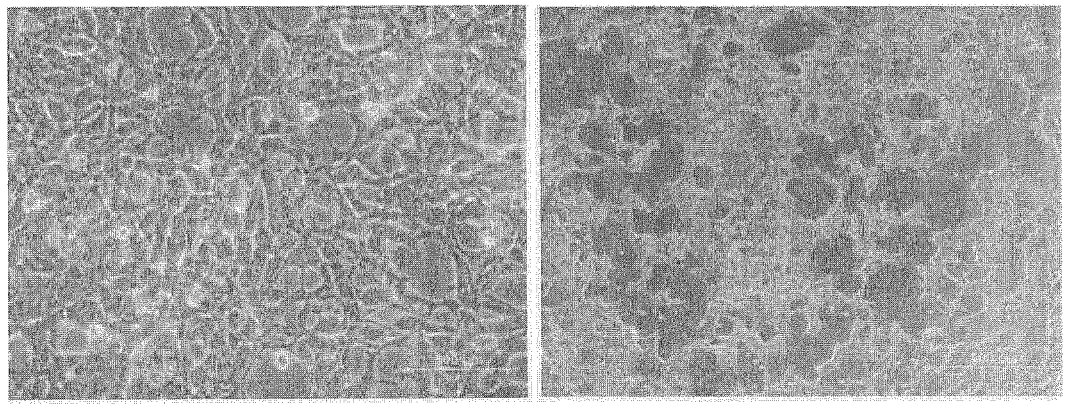

FIG. 9A: MCF-7 breast cancer cells incubated for 48 hours after a single application of Phen at a concentration of 25 μM applied 24 hours after seeding.

Figure 9C:
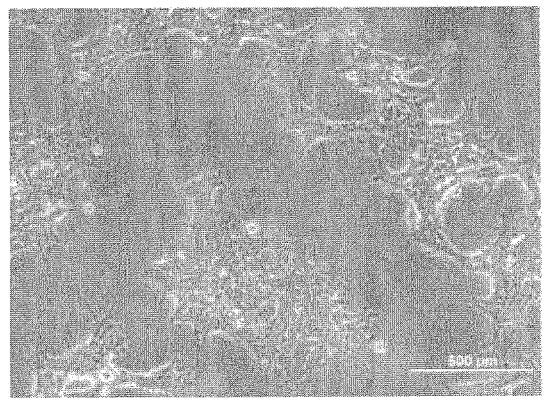

FIGS. 9B and 9C: MCF-7 breast cancer cells incubated for 72 hours after a single application of Phen at a concentration of 50 μM applied 24 hours after seeding.

FIG. 10

MCF-7 breast cancer cells incubated for 72 hours after single application of 3-AB 1 mM applied 24 hours after seeding.

FIG. 11

FIGS. 11A(I), 11A(II), 11A(III) and 11A(IV): phenanthridine derived PARP inhibitor eradicated MCF-7 breast cancer cells 24 hours after seeding 48 hours with: control—FIG. 11A(I); PJ-34 (10 μM)—FIG. 11A(II); Phen (25 μM)—FIG. 11A(III); and Tiq-A (50 μM)—FIG. 11A(IV).

Figure 11B:
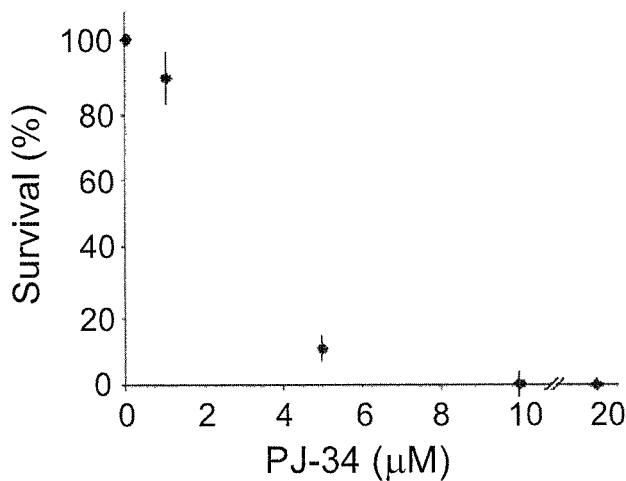

FIG. 11B: survival rate of MCF-7 breast cancer cells after incubation for 48 hours with several concentrations of PJ-34.

Figure 11C:
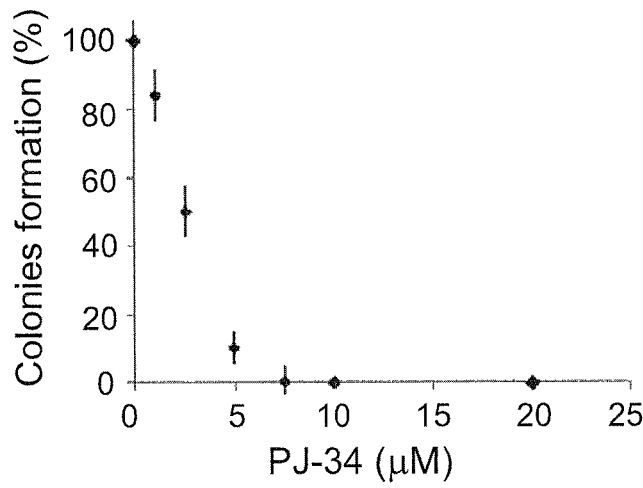

FIG. 11C: colony formation of MCF-7 breast cancer cells reseeded and incubated for 2 additional weeks in the absence of PJ-34, 48 hours after a single application of PJ-34 was applied 24 hours after the initial seeding.

FIGS. 11D(I), 11D(II), 11D(III) and 11D(IV): phenanthridine derived PARP inhibitor eradicated MDA-MB-231 breast cancer cells 24 hours after seeding 48 hours with: control—FIG. 11D(I); PJ-34 (10 μM)—FIG. 11D(II); PJ-34 (20 μM)—FIG. 11D(III); and PJ-34 (30 μM)—FIG. 11D(IV).

Figure 11E:
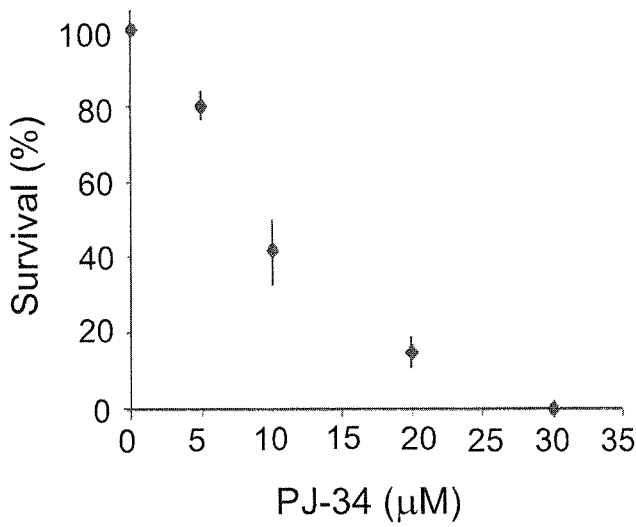
Figures 12M, 12N, 12O:
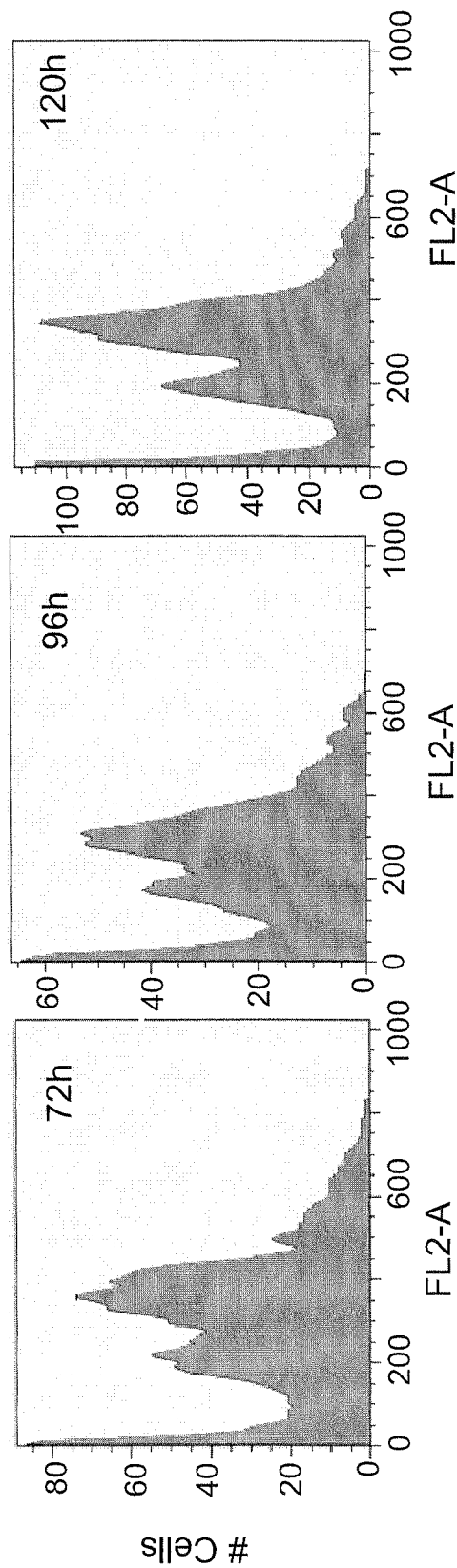

FIG. 11E: survival rate of MDA-MB-231 breast cancer cells after 72 hours of incubation with several concentrations of PJ-34, applied (a single application) 24 hours after seeding. Each value is an average of three measurements obtained in three different experiments.

FIGS. 12A-O

FACS (flow cytometry) analysis indicates G2/M cell cycle arrest and cell death in MCF-7—FIGS. 12A-F—and MDA-MB-231—FIGS. 12G-O—human breast cancer cells treated with PJ-34 (10 μM) applied 24 hours after seeding.

FIG. 13

FIGS. 13A(I), 13A(II), 13A(III), 13A(IV), 13A(V), 13A(VI): human epithelial MCF-10A cells incubated for 72 hours with PJ-34 96 hours after seeding at the indicated concentrations. Control—FIG. 13A(I), PJ-34 (10 μM)—FIG. 13A(II), PJ-34 (20 μM)—FIG. 13A(III), PJ-34 (30 μM)—FIG. 13A(IV), control after two weeks—FIG. 13A(V), and PJ-34 (10 μM) after two weeks—FIG. 13A(VI).

FIGS. 13B(I), 13B(II), 13B(III), 13B(IV), 13B(V) and 13B(VI): FACS analysis indicated that MCF-10A cells overcome G2/M arrest induced by treatment with PJ-34 (10 μM). Control—FIG. 13B(I), after 6 hours incubation with PJ-34—FIG. 13B(II), after 18 hours incubation with PJ-34—FIG. 13B(III), after 24 hours incubation with PJ-34—FIG. 13B(IV), after 48 hours incubation with PJ-34—FIG. 13B(V) and after 72 hours incubation with PJ-34—FIG. 13B(VI).

FIG. 14

FIGS. 14A(I), 14A(II), 14A(III) and 14A(IV): effect of PJ-34 on mouse embryonic fibroblasts (MEF). Control—FIG. 14A(I), taken 72 hours after treatment over a period of 48 hours with PJ-34 (10 μM)—FIG. 14A(II), control after 170 hours—FIG. 14A(III), and taken 170 hours after treatment over a period of 100 hours with PJ-34 (20 μM)—FIG. 14A(IV).

Figure 14B:
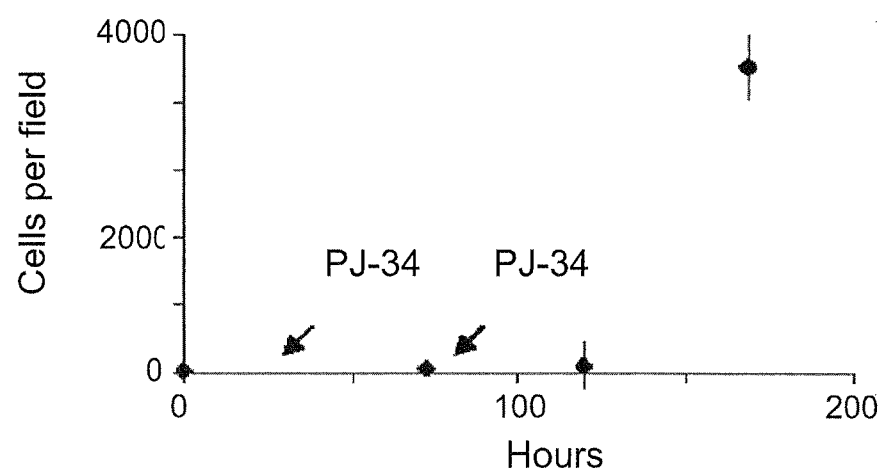

FIG. 14B: number of cells treated with PJ-34 as a measure of time.

FIGS. 14C(I), 14C(II), 14C(III), 14C(IV), 14C(V) and 14C(VI): MEF cells overcame G2/M arrest induced by treatment with PJ-34 (10 μM). Control—FIG. 14C(I), after 6 hours—FIG. 14C(II), after 18 hours—FIG. 14C(III), after 24 hours-FIG. 14C(IV), after 30 hours—FIG. 14C(V) and after 48 hours—FIG. 14C(VI).

FIG. 15

FIGS. 15A(I), 15A(II) and FIGS. 15B(I), 15B(II): treatment with PJ-34 prevented the development of MCF-7 xenotransplants in nude mice (untreated—FIG. 15A(I) and treated—FIG. 15A(II)) and MDA-MB-231 xenotransplants in nude mice (untreated-FIG. 15B(I) and treated—FIG. 15B(II)).

Figures 15C, 15D:
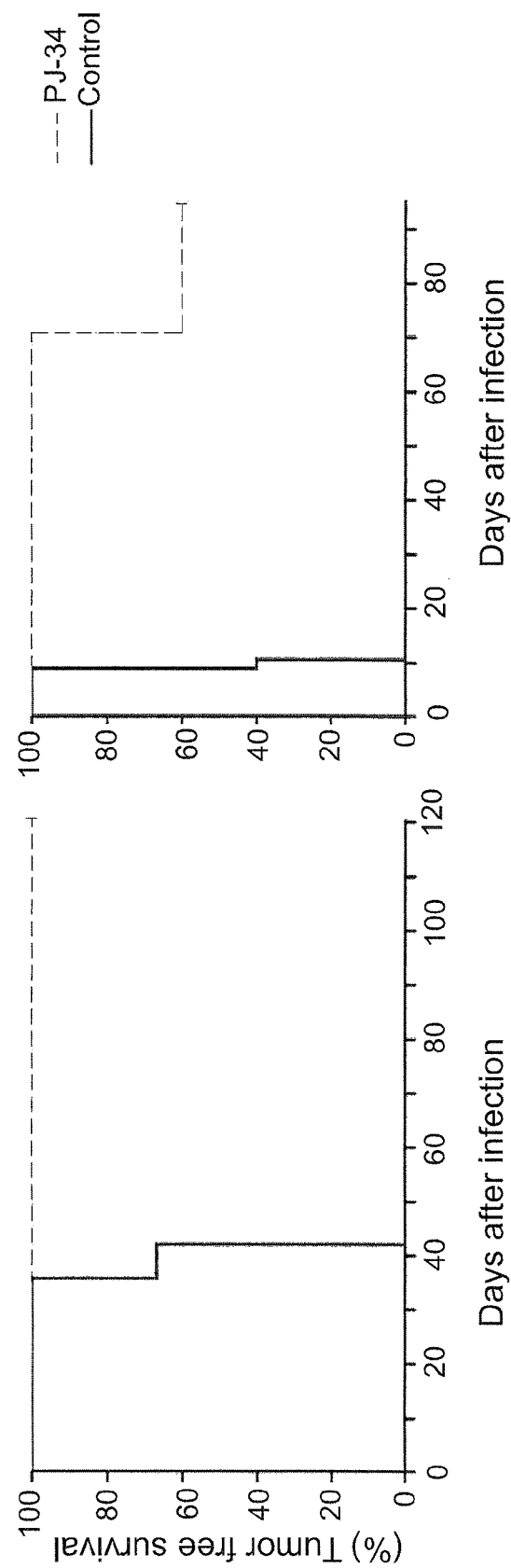

FIG. 15C and FIG. 15D: tumor survival rate of female nude mice after injection of human MCF-7 or MDA-MB-231 cells in the absence or presence of treatment with PJ-34.

FIG. 16

Figure 16B:
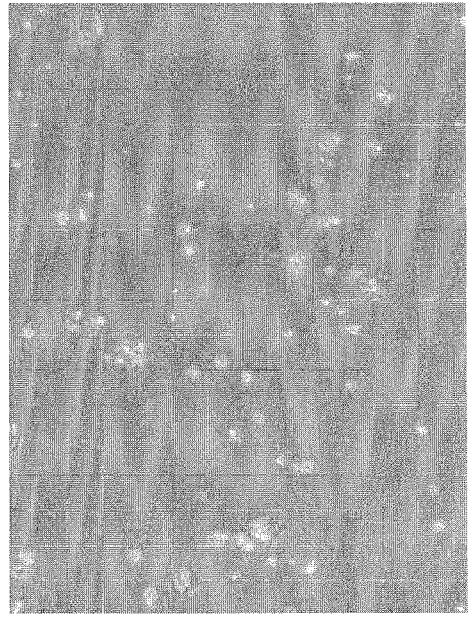
Figure 16A:
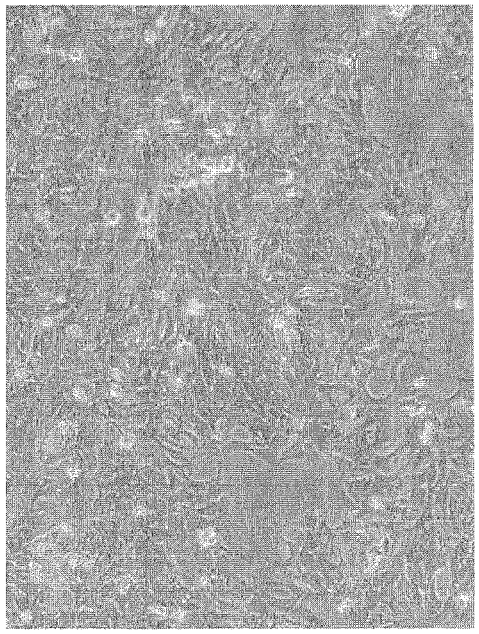

FIGS. 16A-16B: human colon cancer DLD-1 cells incubated with PJ-34 for 96 hours, 24 hours after seeding. Control—FIG. 16A and treated—FIG. 16B.

FIG. 17

Figure 17B:
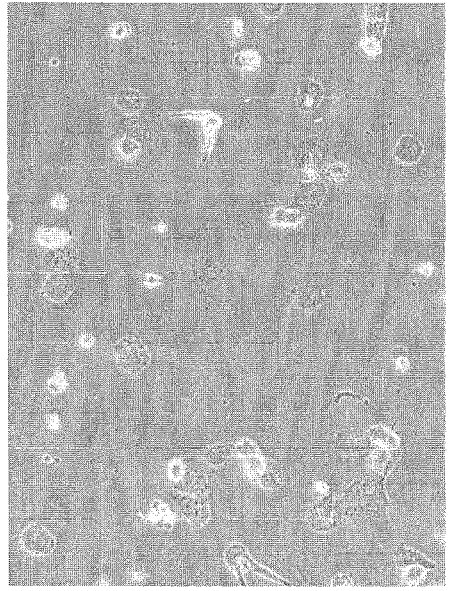
Figure 17A:

FIGS. 17A-17B: human lung cancer H1299 cells incubated with PJ-34 for 96 hours, 24 hours after seeding. Control—FIG. 17A and treated—FIG. 17B.

FIG. 18

Figure 18A:
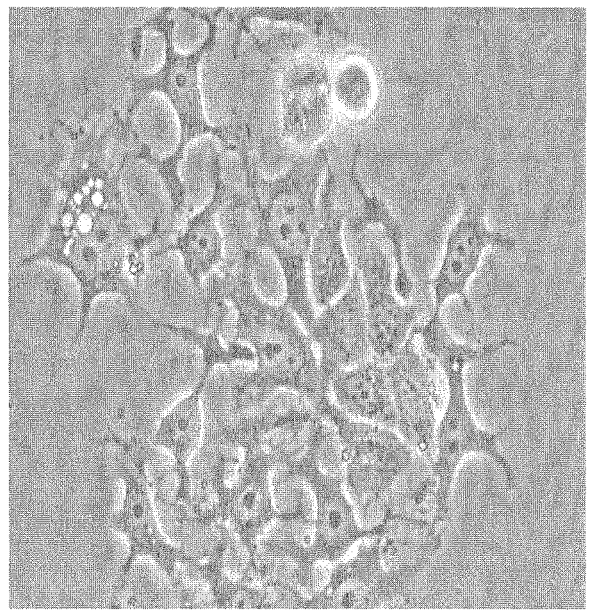
Figure 18B:
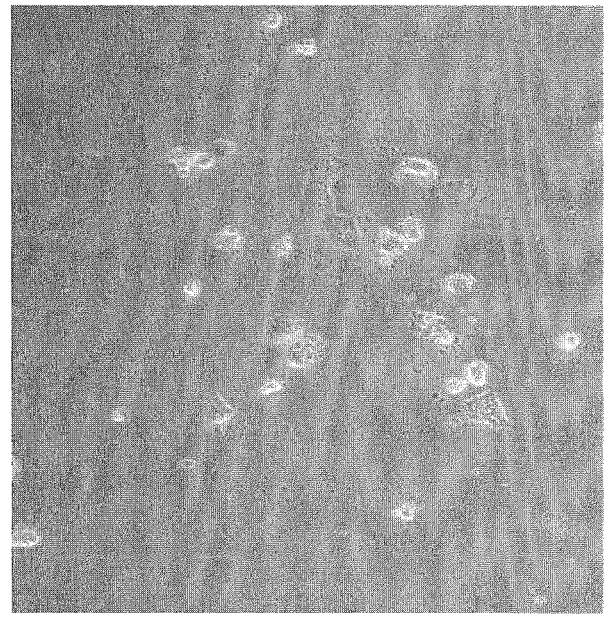

FIGS. 18A-18B: human pancreatic cancer cells, PANC1, incubated with PJ-34 for 96 hours, applied 24 hours after seeding. Control—FIG. 18A, PJ-34 (20 μM)—FIG. 18B.

FIG. 19

Figure 19A:
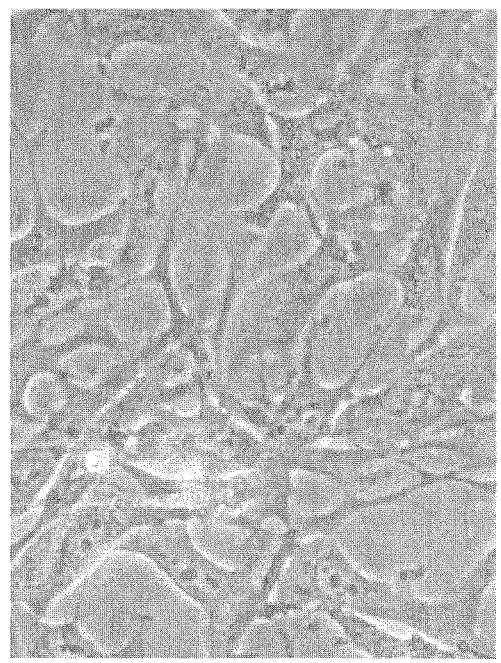
Figure 19B:
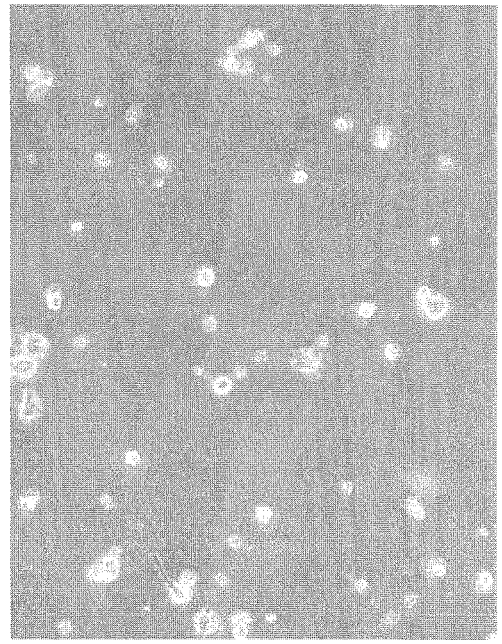

FIGS. 19A-B: human ovarian cancer HeyAB cells, incubated with PJ-34 for 96 hours, 24 hours after seeding. Control—FIG. 19A, PJ-34 (20 μM)—FIG. 19B.

FIG. 20

Figures 20A, 20B:
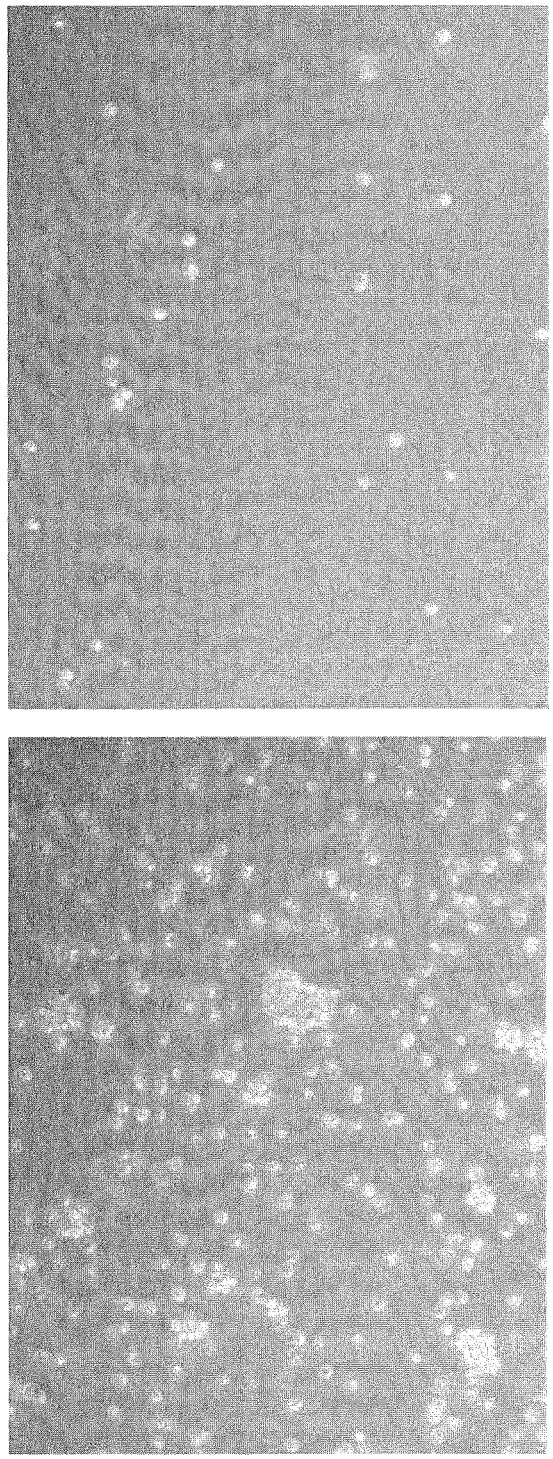

FIGS. 20A-B: human lymphoid leukemia REH, incubated with PJ-34 for 96 hours applied only once, 24 hours after seeding. Control—FIG. 20A, PJ-34 (20 μM)—FIG. 20B.

FIG. 21

FIGS. 21A-H: synergistic effect between MEK and PARP inhibitors in eradication of the triple negative BRCA deficient human breast cancer HCC1937 cells. Control—FIG. 21A, with MEK inhibitor (5 μM) only—FIG. 21B, with MEK inhibitor (10 μM) only—FIG. 21C, with PJ-34 (5 μM) only—FIG. 21D, with PJ-34 (10 μM) only—FIG. 21E, PJ-34 and U0126 (5 μM each)—FIG. 21F, PJ-34 (10 μM) and U0126 (5 μM)—FIG. 21G, Tiq-A (50 μM) and U0126 (5 μM)—FIG. 21H.

Figure 22:
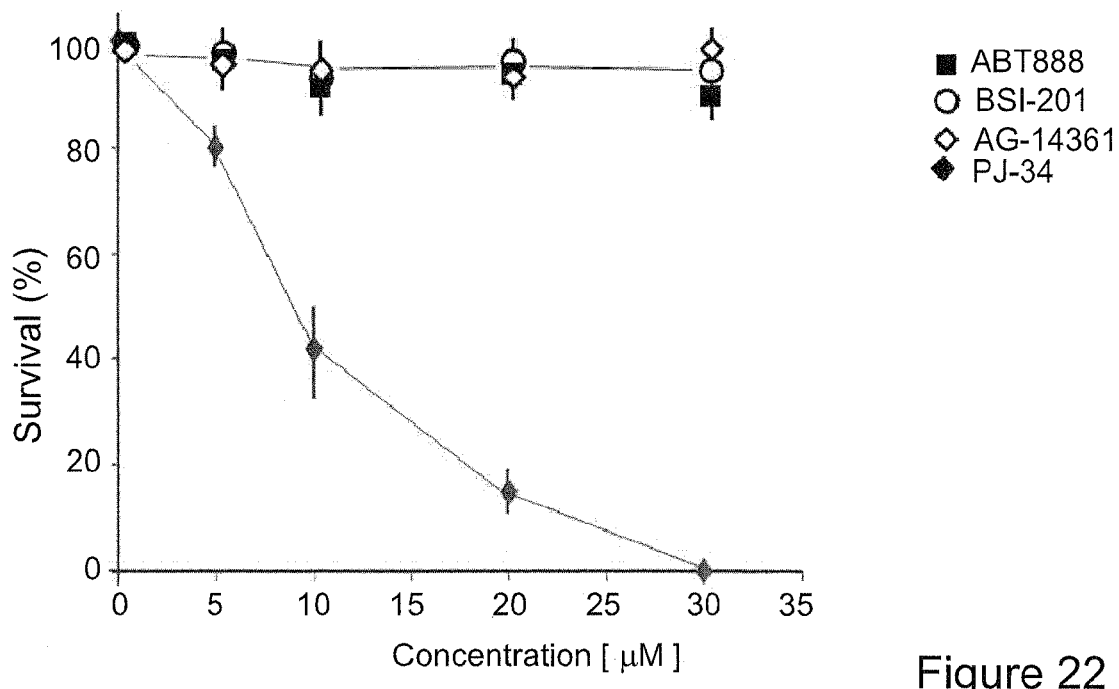

FIG. 22: A comparison between the efficiency of PJ-34 and other PARP-1 inhibitors for eradication of breast cancer MDA-MB-231 cells in a cell culture.

FIG. 23

Figure 23A:
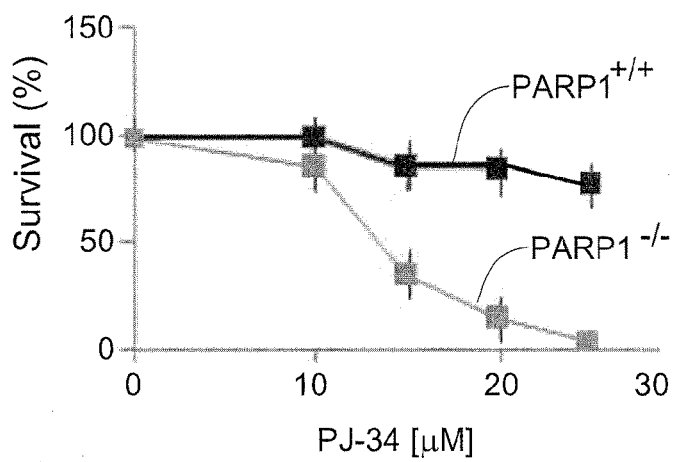
Figure 23B:
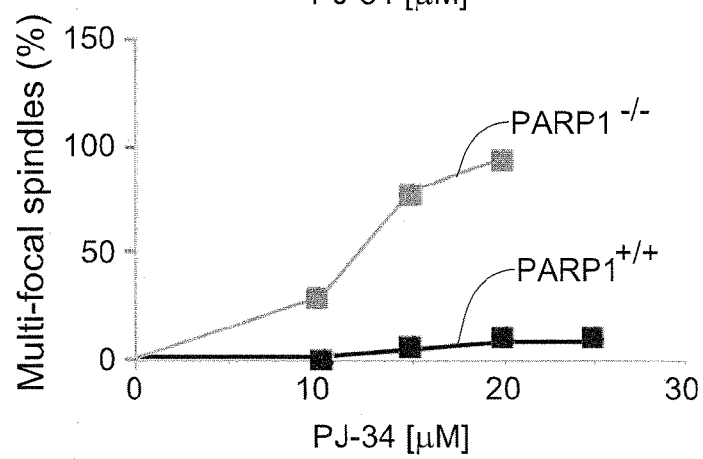

FIG. 23A and FIG. 23B: PJ-34 is cytotoxic to Parp-1$^{-/-}$ mouse embryonic fibroblasts (MEF).

Figure 24A:
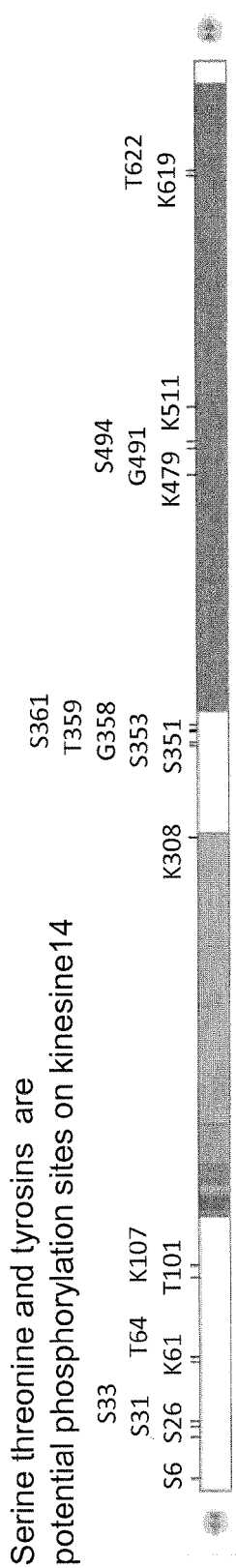

FIG. 24: FIG. 24A shows several phosphorylation sites that may be involved in post-translational modifications of HSET. FIG. 24B(I) shows the effect of PJ-34, Tiq-A, Phen and ABT-888 on the post-translational modifications of HSET by measuring changes in the pI of the protein in MDA-MB-231 breast cancer cells. FIG. 24B(II) shows the effect of PJ-34 on the post-translational modifications of HSET by measuring changes in the pI of the protein in MCF10A cells.

Figure 25:
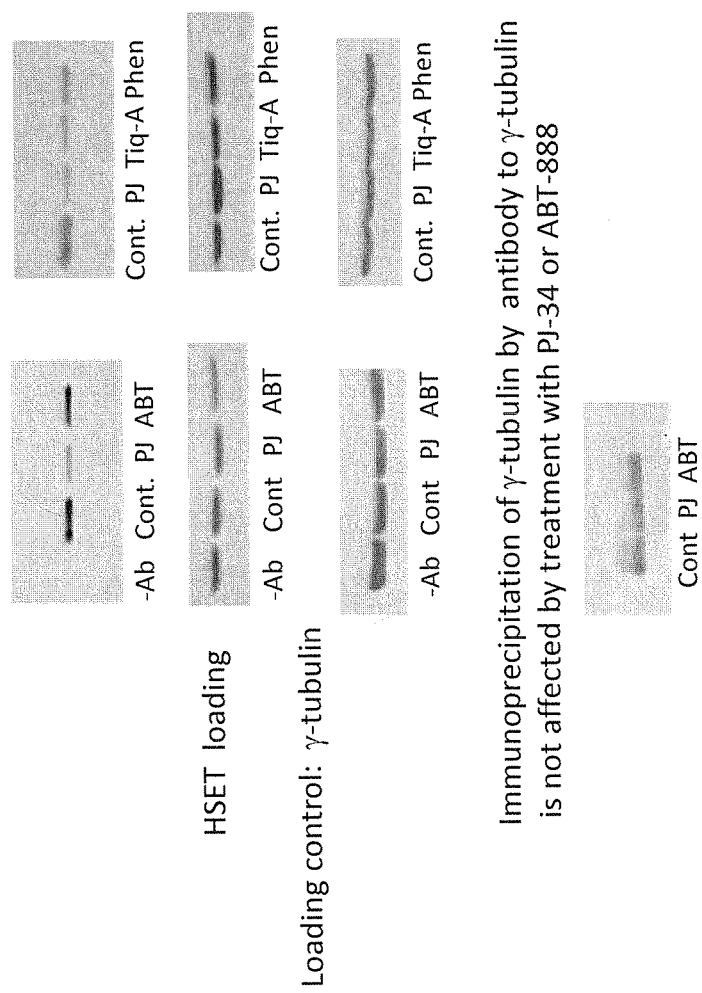

FIG. 25: Co-IP of kinesin-14/HSET with γ-tubulin.

Figure 26:
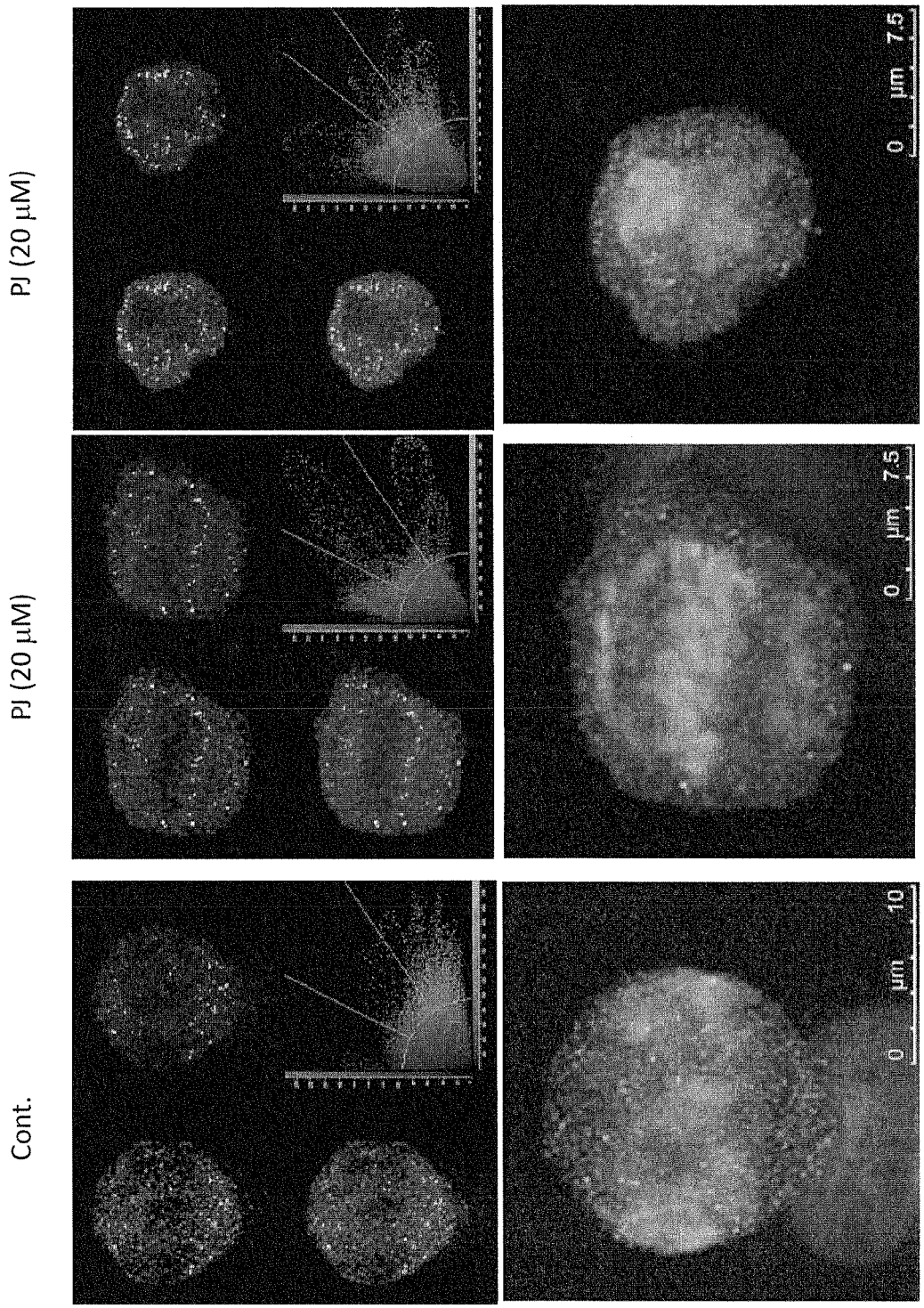

FIG. 26: Co-localization of γ-tubulin and tankyraseI in MDA-MB-231 cells.

Figure 27:
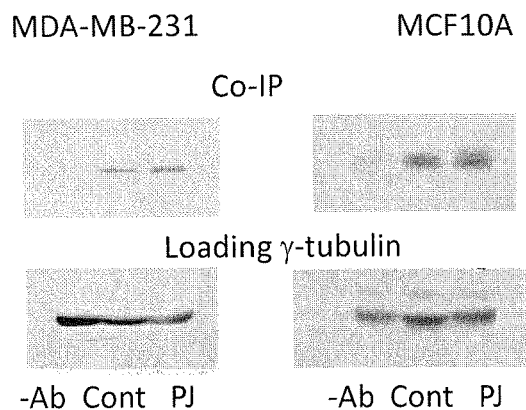

FIG. 27: Co-immunoprecipitation of γ-tubulin with tankyrase1.

Figure 28:
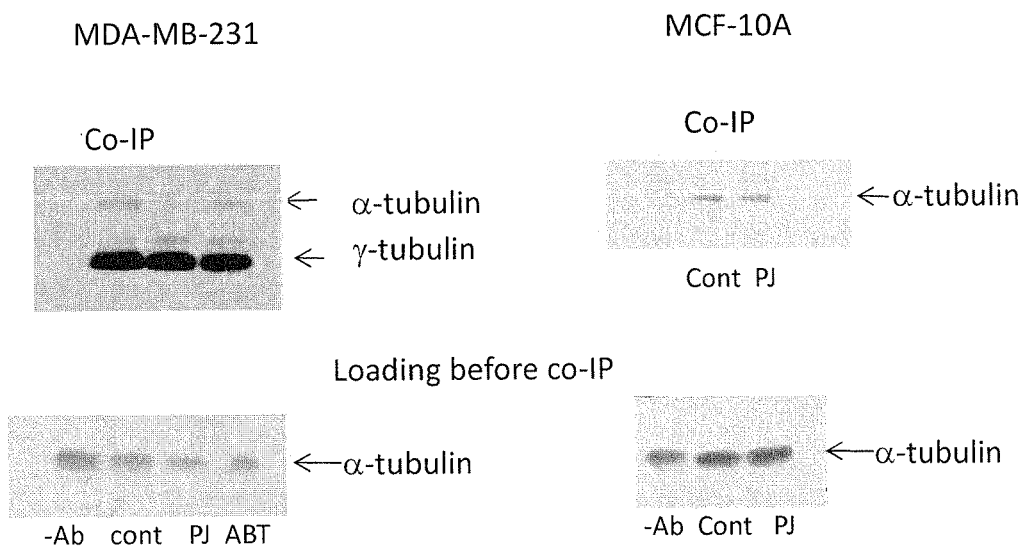

FIG. 28: co-immunoprecipitation of α-tubulin with γ-tubulin in cancer cells.

Figure 29A:
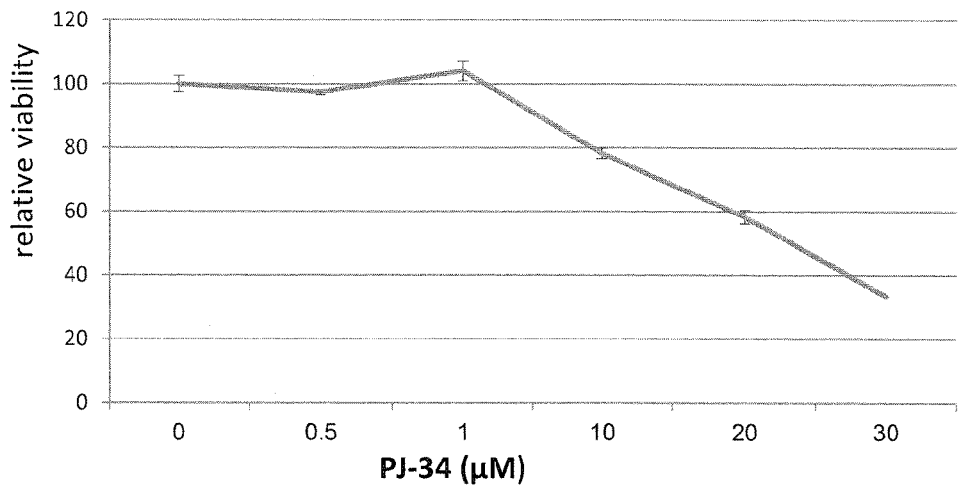

FIG. 29A: Eradication of the malignant U-87 Glioblastoma cells treated with PJ-34 (72 h).

Figure 29B:
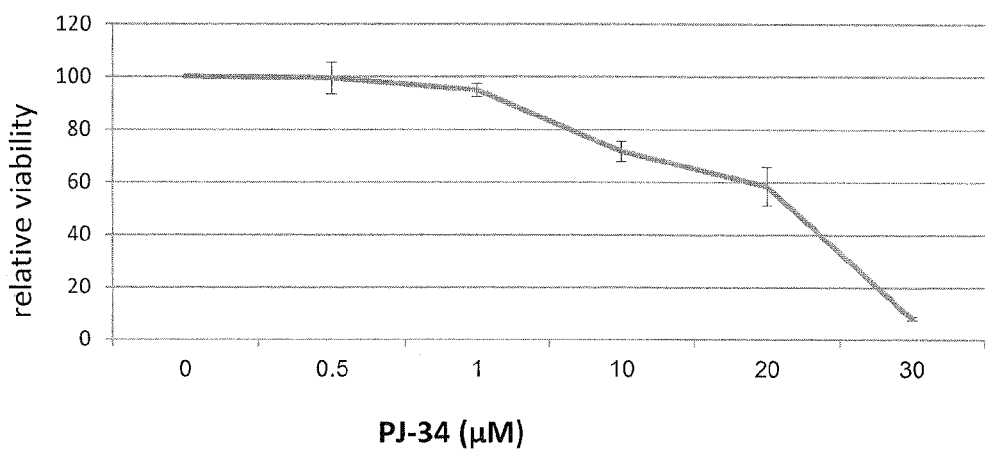

FIG. 29B: Eradication of the malignant U-87 Glioblastoma cells treated with PJ-34 (96 h).

Figure 30:
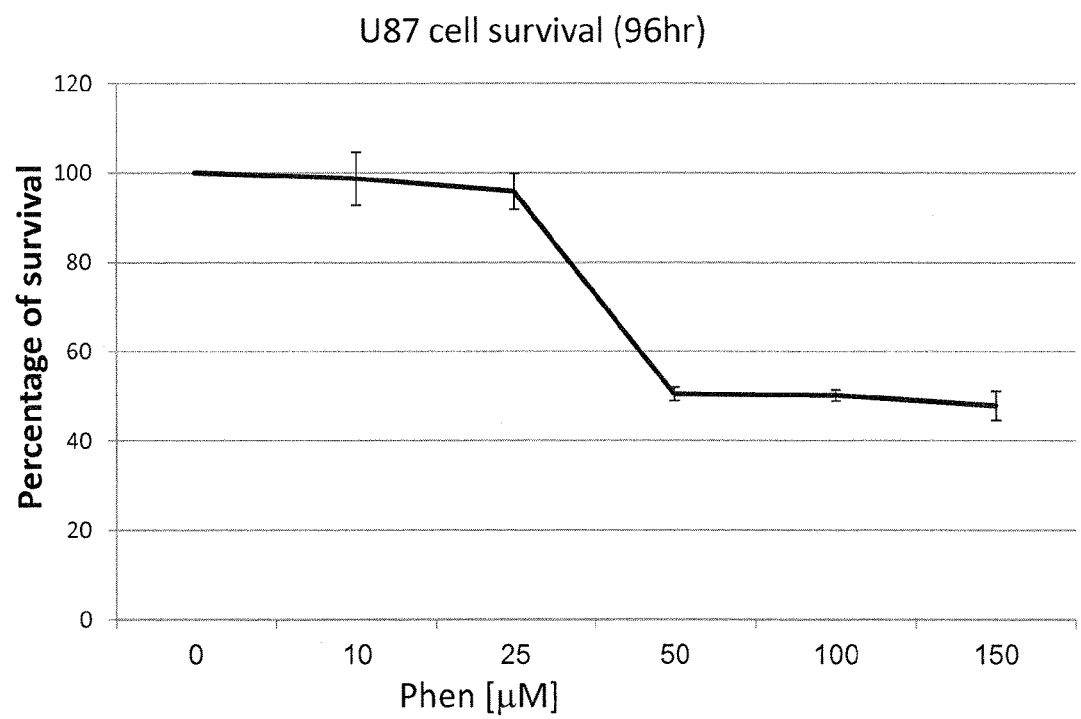

FIG. 30: Eradication of the malignant U-87 Glioblastoma cells treated with Phen (96 h).

Figure 31:
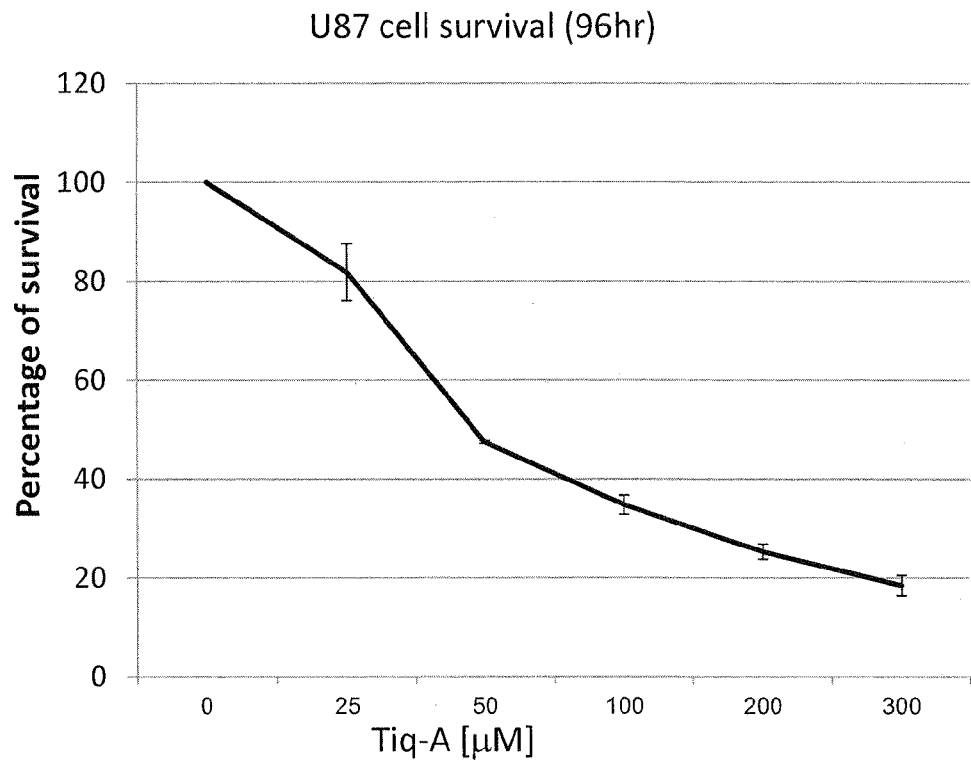

FIG. 31: Eradication of the malignant U-87 Glioblastoma cells treated with Tiq-A (96 h).

Figure 32D:
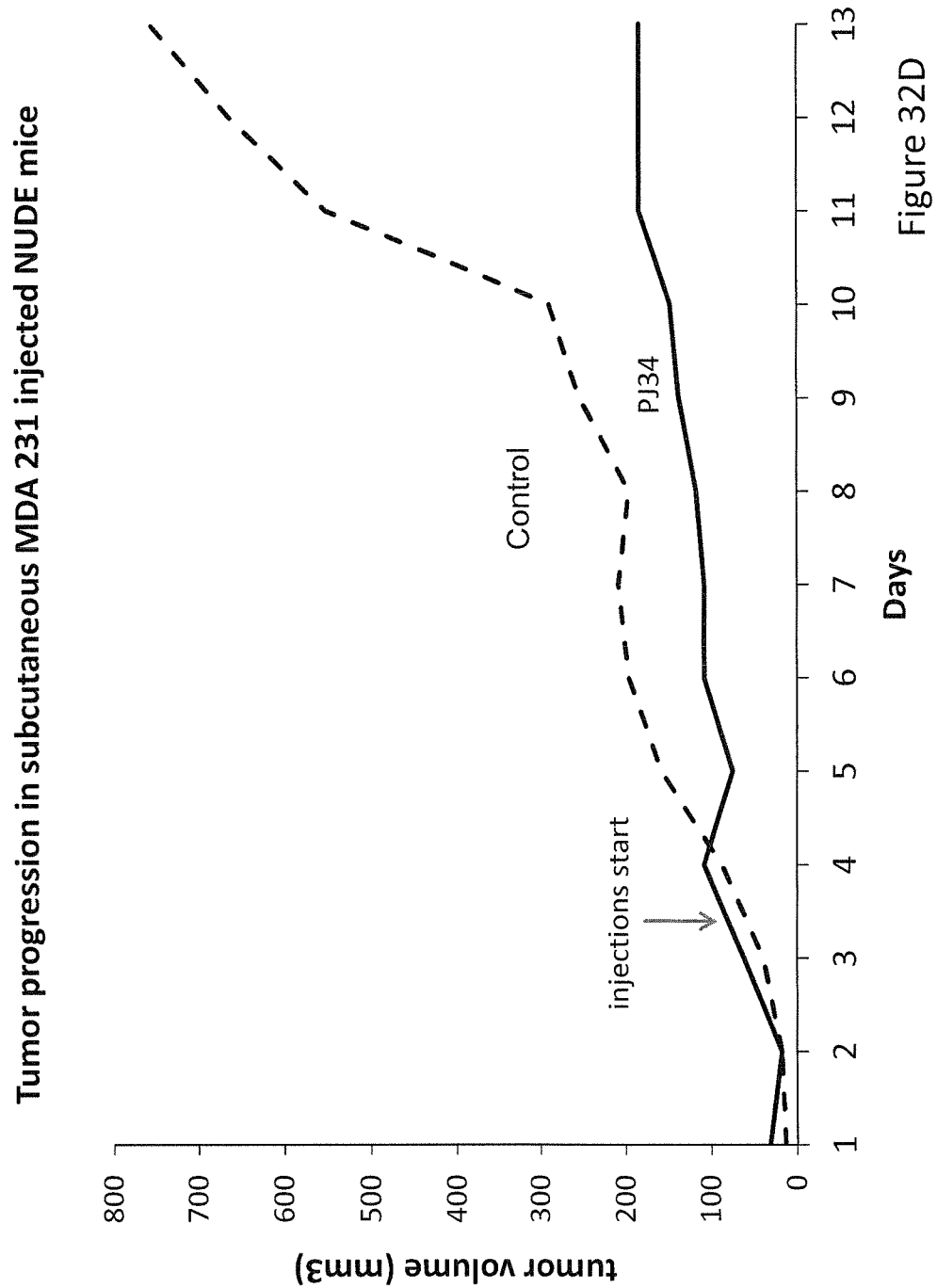

FIGS. 32A-D: treatment with PJ-34 prevented development of MDA-MB-231 xenotransplants in nude mice (untreated—FIG. 32A, treated—FIG. 32B and FIG. 32C. FIG. 32D: tumor progression in female nude mice after subcutaneous injection of human MDA-MB-231 cells in the absence or presence of treatment with PJ-34 injected i.p. (intra-peritoneal) daily for 14 days.

DETAILED DESCRIPTION OF THE INVENTION

As disclosed, the subject invention provides a new and efficient methodology to the treatment or prevention of cancer.

The inventors have discovered that unlike other PARP-1 inhibitors, the compounds PJ-34, Tiq-A and Phen act as multi-centrosome de-clustering agents and are useful in eradicating multi-centrosomal human cancer cells by mitotic catastrophe cell death while normal bi-centrosomal cells were unaffected. The activity of PJ-34, Tiq-A and Phen is not attributed to PARP-1 inhibition but to a different mechanism, which is not shared by other PARP-1 inhibitors. For this reason, PJ-34, Tiq-A and Phen eradicate non-brca cancer cells that are not eradicated by other even more potent PARP1 inhibitors.

Moreover, the activity was independent on the presence of PARP1 in the eradicated cells. Moreover, PARP1 KO MEF (mouse embryonic fibroblasts) were efficiently eradicated by PJ-34 despite PARP-1 deficiency, while normal MEF were resistant to the treatment. PARP1 KO MEF are multi-centrosomal cells, and therefore these cells were chosen for testing the effect of PJ-34 in PARP1 deficient multi-centrosomal cells.

Furthermore, the inventor found the target of PJ-34, Tiq-A and Phen that may explain their cytotoxic activity in multicentrosomal cells. These small molecules act on the human kinesin-14 (HSET), one of the proteins responsible for extra-centrosomes bi-focal clustering in human cancer cells. HSET is one of the 'motor' proteins 'walking' on the microtubules, enabling spindle arrangement and transfer of proteins to the spindle poles in mitosis. Its binding to α-tubulin in the microtubules is apparently required for formation of normal bi-focal spindles and extra-centrosomes bi-focal clustering. The inventor found that this protein is transformed only in human cancer cells (e.g., MDA-MB-231 cells), but not in human normal cells (e.g., epithelial cells MCA10A).

It should also be noted that the activity of PJ-34 in extra-centrosomes de-clustering occurs at higher concentrations as compared to its activity in PARP1 inhibition. PJ-34 acts as a centrosomes de-clustering agent above 20 microM, at 1000-1500 times higher concentrations than the $EC_{50}$ required for PARP1 inhibition by PJ-34 (20 nM). For example, FIGS. 29A and 29B demonstrate the effect of PJ-34 on survival of glioblastoma U-87 cell. Glioblastoma U-87 cells were incubated for 72 and 96 hours after a single application of PJ-34 at a concentration of 0, 0.5, 1, 10, 20 and 30 μM applied 24 hours after seeding. As can be seen from the figures, PJ-34 does not eradicate these cancer cells at concentrations inhibiting the activity of PARP1. Moreover, PARP1 inhibitors did not eradicate the types of cancer cells efficiently eradicated by PJ-34.

In view of the experimental results discussed and presented in the figures, one of skill in the art would recognize that PJ-34 as well as the other compounds are effective in inhibiting and eradicating human breast cancer cells (several cell lines), human colon cancer cells, human lung cancer cells, human pancreatic cancer cells, human lymphoid leukemia cells, and human ovarian cancer cells, along with glioblastoma brain cancer cells (see FIGS. 29A and 29B). Furthermore, the Tiq-A and Phen compounds, which are structurally similar to PJ-34, also correlate very closely to the experimental results observed for PJ-34 in its effect on human breast cancer cells (Examples 7, 10 and 17) and in targeting HSET post-translational modification and the binding of HSET to γ-tubulin (FIGS. 24 and 25) in human cancer cells.

The experimental results clearly demonstrate that PJ-34 and Tiq-A and Phen do not act as PARP1 inhibitors, these molecules eradicate PARP1 deficient cells and act as multi-centrosome de-clustering agents, which are useful in eradicating multi-centrosomal human cancer cells during mitosis by spindle distortion and extra-centrosomes de-clustering that lead to mitotic catastrophe cell death while leaving normal bi-centrosomal cells unaffected. Unlike cancer cells, normal cells are independent of HSET functioning during mitosis. The cytotoxic activity of PJ-34 was achieved at higher concentrations than required for PARP1 inhibition, in a large (orders of magnitude) difference in therapeutically effective amount (e.g., $IC_{50}$) and in non-brca cancer cells that were not eradicated by non-phenanthrene PARP inhibitors.

The term "cancer" as used herein should be understood to encompass any neoplastic disease which is characterized by abnormal and uncontrolled cell division causing malignant growth or tumor. Cancer cells, unlike benign tumor cells, exhibit the properties of invasion and metastasis and are highly anaplastic. Cancer as used herein may refer to either a solid tumor or tumor metastasis. Non-limiting examples of cancer are breast cancer, cervical cancer, ovary cancer, endometrial cancer, melanoma, prostate cancer and pancreatic cancer. In a specific embodiment, the cancer is breast cancer.

Examples of cancers which are treateable by compounds disclosed herein are selected amongst blastoma, carcinoma, lymphoma, leukemia, sarcoma, mesothelioma, glioma, germinoma, choriocarcinoma, melanoma, glioblastoma, lymphoid malignancies and any other neoplastic disease or disorder.

Non-limiting examples of cancers are squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, glioblastoma, ovarian cancer, liver cancer, bladder cancer, hepatoma, colon cancer, rectal cancer, colorectal cancer, endometrial or uterine carcinoma, salivary gland carcinoma, kidney or renal cancer, vulval cancer, thyroid cancer, hepatic carcinoma, anal carcinoma, penile carcinoma, as well as head and neck cancer.

In some embodiments, said cancer is a solid cancer, selected in a non-limiting manner from sarcomas and skin cancer.

In some embodiments, the cancer is selected from breast cancer, lung cancer, pancreatic cancer, ovary cancer and leukemia.

In other embodiments, the cancer is breast cancer.

MCF-7 cells represent an in-vitro model of the most abundantly occurring estrogen dependent human breast cancer. The subject invention shows a very efficient and rapid killing of MCF-7 breast cancer cells by PJ-34, both in vitro and in vivo, without killing non-dividing cells (brain neurons and cardiomyocytes) or dividing normal cells like MCF-10A human epithelial cells or mouse embryonic fibroblasts (MEF), and with only temporarily slowing down the proliferation of dividing normal cells MCF10A and MEF.

The subject invention also shows efficient killing of MCF-7 and MDA-MB-231 breast cancer cells by each of Tiq-A and Phen.

MDA-MB-231 human breast cancer cells are an in vitro model for human cancer cells that lack the estrogen, progesterone and Her2 receptors. The subject invention demonstrates a very efficient and rapid method for killing MDA-MB-231 breast cancer cells by PJ-34, both in vitro and in vivo, without killing non-dividing cells (brain neurons and cardiomyocytes) or dividing normal cells like MCF-10A human epithelial cells, and with only temporarily slowing down the proliferation of dividing normal cells as MCF10A.

As used herein, a subject can be a male or a female subject; the subject can be a human or any other mammal.

The term "treating cancer" as used herein should be understood to e.g. encompass treatment resulting in a decrease in tumor size; a decrease in rate of tumor growth; stasis of tumor size; a decrease in the number of metastasis; a decrease in the number of additional metastasis; a decrease in invasiveness of the cancer; a decrease in the rate of progression of the tumor from one stage to the next; inhibition of tumor growth in a tissue of a mammal having a malignant cancer; control of establishment of metastases; inhibition of tumor metastases formation; regression of established tumors as well as decrease in the angiogenesis induced by the cancer, inhibition of growth and proliferation of cancer cells and so forth. The term "treating cancer" as used herein should also be understood to encompass prophylaxis such as prevention as cancer reoccurs after previous treatment (including surgical removal) and prevention of cancer in an individual prone (genetically, due to life style, chronic inflammation and so forth) to develop cancer. As used herein, "prevention of cancer" is thus to be understood to include prevention of metastases, for example after surgical procedures or after chemotherapy.

As used herein, the breast cancer can be a luminal breast cancer or a basal like breast cancer. Luminal tumors generally express estrogen receptors (ER) with or without co-expression of the progesterone receptor (PR). Basal-like tumors are defined by lack of ER, PR and the human epidermal growth factor receptor (HER2); they express cytokeratins.

Tumors from Brca1 genetic mutation carriers are often basal like breast cancers (BLBC), whereas Brca2 deficient breast cancer cells have been shown to be mainly luminal cancers.

As used herein, breast cancer can be female breast cancer or male breast cancer.

As used herein, the breast cancer can be any breast cancer such as, but not limited to the luminal breast cancers MCF-7, modified MCF-7, DoxR-MCF7, T47D, adenocarcinoma, MDA-MB-231 and the BLBC cancers SUM149, HCC1937 and SUM1315MO2.

In some embodiments, the breast cancer is not associated with a deficiency or mutation in brca 1 and brca 2, i.e. the breast cancer is brca1(+/+) and brca2(+/+).

In other embodiments, the homozygous breast cancer is MCF-7. The breast cancer MCF-7 is also known as MCF-7/ADR, MCF-7 TH and NCI/ADR (Mehta K. et al., (2002) J. Natl. Canc. Inst. 94, 1652-1654).

In other embodiments, the breast cancer is associated with a deficiency or mutation in brca1 but not associated with a deficiency or mutation in brca2 (namely, normal homozygous for brca2), i.e., brca1(−/−), brca1(−/+) or brca1 (+/−) and brca2+/+.

Examples of breast cancer associated with brca1(−/−) are HCC1937 and SUM1315MO2.

An example of breast cancer associated with brca1(+/−) is MDA-MB-231.

In yet other embodiments, the breast cancer is associated with a deficiency or mutation in brca2 but not associated with a deficiency or mutation in brca1, i.e. is brca1+/+ and brca2−/− or brca2−/+ or brca2+/−.

In yet other embodiments, the breast cancer cell lines MDA231 are Brca1 (+/+) and Brca2 (+/+) namely, are NOT Brca mutants.

In yet other embodiments, the human cancer cell lines DLD-1, H1299, PANC1, HeyAB, SkoV3, REH are not Brca mutants.

The compounds of formula (I) (e.g. PJ-34, Phen and Tiq-A) may be used in the invention in their free base or free acid forms or as pharmaceutically acceptable salt.

The salts may be pharmacologically tolerable salts of inorganic and organic acids used in pharmacy. Those suitable are water-soluble and water-insoluble acid addition salts with acids such as hydrochloric acid (HCl), hydrobromic acid, phosphoric acid, nitric acid, sulfuric acid, acetic acid, citric acid, D-gluconic acid, benzoic acid, 2-(4-hydroxybenzoyl) benzoic acid, butyric acid, sulfosalicylic acid, maleic acid, lauric acid, malic acid, fumaric acid, succinic acid, oxalic acid, tartaric acid, embonic acid, stearic acid, toluenesulfonic acid, methanesulfonic acid or 3-hydroxy-2-naphthoic acid. In some embodiments, the salt is a hydrochloride salt.

The compounds and salts thereof, as well as any composition comprising same are specifically useful for the treatment and prevention of tumors, more particularly tumors located in e.g. breast, ovary, uterus, prostate, skin and pancreas and most specifically those located in the breast. Compounds used in the invention (e.g. PJ-34, Tiq-A, and Phen) and compositions thereof are further useful for the prevention of metastases after surgical procedures or after chemotherapy.

Suitable routes of administration of compounds used in the invention (e.g. PJ-34, Phen and Tiq-A) and compositions thereof are oral, rectal, nasal, topical (including transdermal, buccal and sublingual), vaginal or parenteral (including subcutaneous, intramuscular, intravenous and intradermal) administration or administration via an implant, such as, but not limited to, an osmotic pump, which may for example be implanted within a tumor. In some embodiments, the compounds or compositions thereof can be administered orally.

The exact dose and regimen of administration of compounds used in the invention (e.g. PJ-34, Phen and Tiq-A, including salts thereof) or pharmaceutical compositions thereof, will necessarily be dependent upon the therapeutic effect to be achieved (e.g. treatment of breast cancer) and may vary with the route of administration, and the age and condition of the individual subject to whom the medicament is to be administered.

A dosage for humans is likely to contain 0.0001-25 mg per kg body weight per day. The desired dose may be presented as one dose or as multiple sub-doses administered at appropriate intervals. In one embodiment, the dose is from about 1 to about 20 mg per kg body weight. In another embodiment, the dose is from about 5 to about 18 mg per kg body weight. In yet another embodiment, the dose is from about 7 to about 16 mg per kg body weight. In yet another embodiment, the dose is from about 10 to about 15 mg per kg body weight.

In another embodiment, the dose is from about 0.1 to about 0.9 mg/kg body weight. In another embodiment, the dose is from about 0.2 to about 0.8 mg/kg body weight. In another embodiment, the dose is from about 0.3 to about 0.7 mg/kg body weight. In another embodiment, the dose is from about 0.4 to about 0.6 mg/kg body weight. In another embodiment, the dose is from about 0.5 mg/kg body weight. In a specific embodiment, the dose is about 0.135 mg/kg body weight.

In some embodiments, the dose is at least 30 mg/kg body/day.

In some embodiments, the dose is at most 120 mg/kg body/day.

In some embodiments, the dose is between 30 mg/kg body and 120 mg/kg body. In some embodiments, the dose is between 30 mg/kg body and 100 mg/kg body. In some embodiments, the dose is between 30 mg/kg body and 90 mg/kg body. In some embodiments, the dose is between 30 mg/kg body and 80 mg/kg body. In some embodiments, the dose is between 30 mg/kg body and 70 mg/kg body. In some embodiments, the dose is between 30 mg/kg body and 60 mg/kg body. In some embodiments, the dose is between 30 mg/kg body and 50 mg/kg body. In some embodiments, the dose is between 30 mg/kg body and 40 mg/kg body.

In some embodiments, the dose is between 40 mg/kg body and 120 mg/kg body. In some embodiments, the dose is between 50 mg/kg body and 120 mg/kg body. In some embodiments, the dose is between 60 mg/kg body and 120 mg/kg body. In some embodiments, the dose is between 70 mg/kg body and 120 mg/kg body. In some embodiments, the dose is between 80 mg/kg body and 120 mg/kg body. In some embodiments, the dose is between 90 mg/kg body and 120 mg/kg body. In some embodiments, the dose is between 100 mg/kg body and 120 mg/kg body. In some embodiments, the dose is between 110 mg/kg body and 120 mg/kg body.

In some embodiments, the dose is between 50 mg/kg body and 80 mg/kg body.

In some embodiments, the dose is between 50 mg/kg body and 60 mg/kg body. In some embodiments, the dose is 30 mg/kg body, 40 mg/kg body, 50 mg/kg body, 60 mg/kg body, 70 mg/kg body or 80 mg/kg body. In some embodiments, the dose is 30 mg/kg body, 40 mg/kg body or 50 mg/kg body. In some embodiments, the dose is between 30 mg/kg body and 50 mg/kg body.

The present invention thus also relates to pharmaceutical compositions comprising compounds in admixture with pharmaceutically acceptable carriers (auxiliaries), and optionally other therapeutic agents. The auxiliaries must be "acceptable" in the sense of being compatible with the other ingredients of the composition and not deleterious to the recipients thereof.

Pharmaceutical compositions include those suitable for oral, rectal, nasal, topical (including transdermal, buccal and sublingual), vaginal or parenteral (including subcutaneous, intramuscular, intravenous and intradermal) administration or administration via an implant such as, but not limited to, an osmotic pump, which may for example be implanted within a tumor. The compositions may be prepared by any method well known in the art of pharmacy.

The compositions of the invention may be administered daily or at any regimen depending inert alia on the subject to be treated, the state of the disease, the specific drug or combination of drugs and any other factor a medical practitioner may consider. In some embodiments, the composition of the invention is administered on a daily basis. In other embodiments, the composition is administered once, twice or three times daily. In other embodiments, the composition is administered over a period of time, e.g., over a period of 5, 10, 15 or any other number of days.

Such methods include the step of bringing in association compounds used in the invention or combinations thereof with any auxiliary agent. The auxiliary agent(s), also named accessory ingredient(s), include those conventional in the art, such as carriers, fillers, binders, diluents, disintegrants, lubricants, colorants, flavouring agents, anti-oxidants, and wetting agents.

Pharmaceutical compositions suitable for oral administration may be presented as discrete dosage units such as pills, tablets, dragées or capsules, or as a powder or granules, or as a solution or suspension. The active ingredient may also be presented as a bolus or paste. The compositions can further be processed into a suppository or enema for rectal administration.

The invention further includes a pharmaceutical composition, as hereinbefore described, in combination with packaging material, including instructions for the use of the composition for a use as herein before described.

For parenteral administration, suitable compositions include aqueous and non-aqueous sterile injection. The compositions may be presented in unit-dose or multi-dose containers, for example sealed vials and ampoules, and may be stored in a freeze-dried (lyophilised) condition requiring only the addition of sterile liquid carrier, for example water, prior to use. For transdermal administration, e.g. gels, patches or sprays can be contemplated. Compositions or formulations suitable for pulmonary administration e.g. by nasal inhalation include fine dusts or mists which may be generated by means of metered dose pressurized aerosols, nebulisers or insufflators.

The compounds of formula (I) or compositions thereof may be administered in conjunction with other compounds, including, but not limited to, chemotherapeutic agents such as cytotoxic and cytostatic agents, immunological modifiers such as interferons and interleukins, MEK inhibitors, anti-progestogens, cytokines, folic acid, vitamins, minerals and so forth, and/or in combination with surgery and/or radiation therapy.

The MEK inhibitor can be any MEK inhibitor, such as, but not limited to PD184325 (CI-1040, N-(3-chloro-4-fluorophenyl)-7-methoxy-6-(3-morpholin-4-ylpropoxy)quinazolin-4-amine), PD0325901 (N-[(2R)-2,3-dihydroxypropoxy]-3,4-difluoro-2-[(2-fluoro-4-iodophenyl)amino]-benzamide), PD98059 (2'-amino-3'-methoxyflavone) and U0126 (1,4-diamino-2,3-dicyano-1,4-bis(aminophenylthio)butadiene).

The term "cytotoxic agent" as used herein should be understood to encompass any agent used for the treatment of abnormal and uncontrolled progressive cellular growth. Non-limiting examples of such cytotoxic agents include the alkylating agents cyclophosphamide (CTX)(Bristol-Meyers Squibb), ifosfamide (Bristol-Meyers Squibb), chlorambucil (Glaxo Wellcome), and carmustine (Bristol-Meyers Squibb); the anti-metabolites cytarabine (Pharmacia & Upjohn), 6-mercaptopurine (Glaxo Wellcome), 6-thioguanine (Glaxo Wellcome), and methotrexate (Immunex); the antibiotics doxorubicin (Pharmacia & Upjohn), daunorubicin (NeXstar), and mitoxantrone (Immunex); and miscellaneous agents such as vincristine (Lilly), vinblastine (Lilly), and paclitaxel (Bristol-Meyers Squibb) or their pharmaceutically acceptable salts.

In some embodiments, where the phenanthridine derivative is administered in combination with at least one cytotoxic agent, as defined, the two or more components may be administered in combination or separately with one agent administered prior to, simultaneously with or after administration of the other agent.

The method of the invention may similarly be carried out in conjunction with one or more anti-cancer methodology such as irradiation, chemical treatment, surgical treatment and others.

In an aspect the present invention, there is provided a use of a compound of the general formula (I), or pharmaceutically acceptable salts thereof:

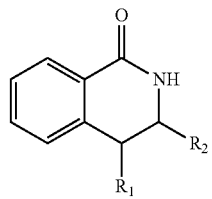

(I)

wherein $R_1$ and $R_2$ together with the carbon atoms to which they are bonded form a 5 or 6 membered aromatic or hetero-aromatic ring, optionally substituted by at least one group selected from amino, formamido, alkyl substituted amido, amine substituted amido, alkylamino substituted amido for the preparation of a medicament to treat or prevent cancer or in a method for the treatment and/or prevention of cancer.

The term "5 or 6 membered aromatic ring" as used herein is understood to encompass an aromatic ring having 5 or 6 carbon atoms together with the two carbon atoms to which $R_1$ and $R_2$ are bonded, thus forming a fused 5 or 6 membered aromatic ring on the 3,4-substituted-isoquinolin-1-one ring system.

The term "5 or 6 membered hetero-aromatic ring" as used herein is understood to encompass any heterocyclic aromatic ring having 5 or 6 atoms, containing one or more independent hetero-atoms selected from nitrogen, oxygen and sulfur, which is fused to the 3,4-substituted-isoquinolin-1-one ring system of the compound of formula (I), through the two carbon atoms to which $R_1$ and $R_2$ are bonded. It should be noted that a heteroatom may be positioned on any position on the fused 5 to 6 membered hetero-aromatic ring formed.

Non-limiting examples of 5-membered hetero-aromatic rings include: furylene, thienylene, pyrrolylene, oxazolylene, thiazolylene, imidazolylene, isoxazolylene, isothiazolylene, 1,2,3-triazolylene, 1,2,4-triazolylene, 1,2,3-oxadiazolylene, 1,2,4-oxadiazolylene, 1,2,5-oxadiazolylene, 1,3,4-oxadiazolylene, 1,2,3-thiadiazolylene, 1,2,4-thiadiazolylene, 1,2,5-thiadiazolylene, 1,3,4-thiadiazolylene and the like. Non-limiting examples of 6-membered hetero-aromatic rings include pyridyl, pyridazinyl, pyrimidinyl, pyrazinyl, 1,2,3-triazinyl, 1,2,4-triazinyl, 1,3,5-triazinyl and the like.

The term "optionally substituted" as used herein means that the 5 or 6 membered aromatic or hetero-aromatic ring is either unsubstituted or substituted with one or more of the substituents specified on any position of the ring relative to the fused ring system. When the 5 or 6 membered aromatic or hetero-aromatic ring is substituted with more than one substituent the substituents may be the same or different.

The term "amino" as used herein is meant to encompass primary, secondary or tertiary amines where the point of attachment is through the nitrogen atom which is substituted with $C_1$-$C_6$ straight or branched alkyl. In case of a tertiary amine, the substituent is the same or different.

The term "formamido" as used herein is meant to encompass a —NH—C(O)—H group.

The term "alkyl substituted amido" as used herein is meant to encompass a —NH—C(O)—$C_1$-$C_6$ alkyl group.

The term "alkylamino substituted amido" as used herein is meant to encompass a —NH—C(O)—$C_1$-$C_6$ alkyl-amino group.

The term "alkyl substituted amino" as used herein is meant to encompass a —$C_1$-$C_6$ alkyl-amino group.

The term "$C_1$-$C_6$ alkyl" should be understood to encompass any straight or branched alkyl moiety having 1, 2, 3, 4, 5 or 6 carbon atoms.

In some embodiments, in a compound of formula (I) $R_1$ and $R_2$ together with the carbon atoms to which they are bonded form a 6-membered aromatic or hetero-aromatic ring. In other embodiments, the 6-membered aromatic ring formed is a phenylene ring. In further embodiments, the phenylene ring is substituted by an amido group having the formula: —NHCOR$_3$, wherein $R_3$ is selected from a group consisting of amino and alkyl substituted amino. In some embodiments, $R_3$ is an alkyl substituted amino. In further embodiments, the alkyl substituted amino is —$CH_2N(CH_3)_2$.

In other embodiments, $R_1$ and $R_2$ together with the carbon atoms to which they are bonded form a 5-membered aromatic or hetero-aromatic ring. In further embodiments, the hetero-aromatic ring formed is a thienylene ring.

The subject invention further provides a use of a compound selected from the group consisting of N-(6-oxo-5,6-dihydro-phenanthridin-2-yl)-N,N-dimethylacetamide, HCl (PJ-34), 4H-Thieno[2,3-c]isoquinolin-5-one (Tiq-A) and 6-(5H)-phenanthridinone (Phen) or combinations thereof for the preparation of a medicament to treat or prevent cancer. In some embodiments, the compound is N-(6-oxo-5,6-dihydro-phenanthridin-2-yl)-N,N-dimethylacetamide HCl (PJ-34).

In another aspect the invention provides a pharmaceutical composition comprising a compound of the general formula (I), or a pharmaceutically acceptable salt thereof:

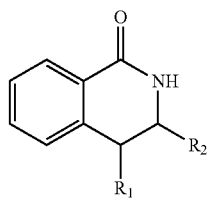

wherein $R_1$ and $R_2$ together with the carbon atoms to which they are bonded form a 5 or 6 membered aromatic or hetero-aromatic ring, optionally substituted by at least one group selected from amino, formamido, alkyl substituted amido, amine substituted amido, alkylamino substituted amido and a pharmaceutically acceptable carrier for use in the treatment or prevention of cancer.

The subject invention further provides a pharmaceutical composition comprising a compound selected from the group consisting of N-(6-oxo-5,6-dihydro-phenanthridin-2-yl)-N,N-dimethylacetamide HCl (PJ-34), 4H-thieno[2,3-c]isoquinolin-5-one(Tiq-A) and 6(5H)-phenanthridinone (Phen) or combinations thereof, and a pharmaceutically acceptable carrier for use in the treatment or prevention of cancer. In some embodiments, the compound is N-(6-oxo-5,6-dihydro-phenanthridin-2-yl)-N,N-dimethylacetamide HCl (PJ-34).

In a further aspect the invention provides a method for the treatment or prevention of cancer in a subject, the method comprising administering a therapeutically effective amount of a compound of the general formula (I), or a pharmaceutically acceptable salt thereof:

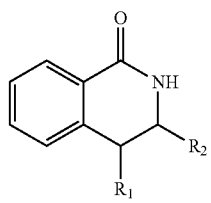

wherein $R_1$ and $R_2$ together with the carbon atoms to which they are bonded form a 5 or 6 membered aromatic or hetero-aromatic ring, optionally substituted by at least one group selected from amino, formamido, alkyl substituted amido, amine substituted amido, alkylamino substituted amido.

The subject invention further envisages a method for the treatment or prevention of cancer comprising administering a therapeutically effective amount of a compound selected from the group consisting of N-(6-oxo-5,6-dihydro-phenanthridin-2-yl)-N,N-dimethylacetamide HCl (PJ-34), 4H-Thieno[2,3-c]isoquinolin-5-one(Tiq-A) and 6(5H)-phenanthridinone (Phen) or combinations thereof and a pharmaceutically acceptable carrier to a subject suffering from cancer. In some embodiments, the compound is N-(6-oxo-5,6-dihydro-phenanthridin-2-yl)-N,N-dimethylacetamide HCl (PJ-34).

In some embodiment, the cancer is breast cancer. The breast cancer is selected from brca1(+/+) and brca2(+/+). In some embodiments, the breast cancer is MCF-7 and MDA231.

In other embodiments, the breast cancer is brca1(−/−) or brca1(−/+) or brca1 (+/−). In yet other embodiments, the breast cancer is brca2(−/−) or brca2(−/+) or brca2(+/−).

Compounds of the invention (e.g. PJ-34, Tiq-A and Phen) or compositions thereof are further useful to test whether cancer cells taken from a biopsy are sensitive to such compounds (e.g. PJ-34, Tiq-A and/or Phen).

As stated above, a compound of formula (I) or compositions thereof may be administered in conjunction with other compounds, including, but not limited to MEK inhibitors. MEK is a key protein kinase in the RAS/RAF/MEK/ERK pathway, which signals for cancer cell proliferation and survival. MEK is frequently constitutively activated in cancer cells, in particular in tumors that have mutations in the RAS and RAF oncogenes. MEK also regulates the biosynthesis of the inflammatory cytokines TNF, IL-6 and IL-1, which can act as growth and survival factors in cancer.

The MEK inhibitor may be any MEK inhibitor, such as, but not limited to PD184325 (CI-1040, N-(3-chloro-4-fluorophenyl)-7-methoxy-6-(3-morpholin-4-ylpropoxy)quinazolin-4-amine), PD0325901 (N-[(2R)-2,3-dihydroxypropoxy]-3,4-difluoro-2-[(2-fluoro-4-iodophenyl)amino]-benzamide), PD98059 (2'-amino-3'-methoxyflavone) and U0126 (1,4-diamino-2,3-dicyano-1,4-bis(aminophenylthio)butadiene).

Administering compound a MEK inhibitor, such as U0126 with one or more compounds of formula (I) such as PJ-34, Tiq-A and Phen, enhances eradication of cancer cells as compared to administering a MEK inhibitor alone or to administering one of the compounds of formula (I) alone. This effect may be additive or synergistic.

The administering of a compound of the general formula (I) with a MEK inhibitor may be in combination with, simultaneously to, separately or sequentially to the other.

In another aspect, the invention provides a method for the treatment or prevention of cancer comprising administering a therapeutically effective amount of a compound the general formula (I) and at least one MEK inhibitor to a subject suffering from cancer.

In some embodiments, at least one compound of formula (I) is administered with at least one MEK inhibitor selected from PD184325 (CI-1040, also named Gefitinib or Iressa: N-(3-chloro-4-fluorophenyl)-7-methoxy-6-(3-morpholin-4-ylpropoxy)quinazolin-4-amine), PD0325901, PD98059 and U0126.

In another aspect, the invention provides a method for the treatment or prevention of cancer comprising administering a therapeutically effective amount of a compound selected from the group consisting of N-(6-oxo-5,6-dihydro-phenanthridin-2-yl)-N,N-dimethylacetamide HCl (PJ-34), 4H-thieno[2,3-c]isoquinolin-5-one (Tiq-A) and 6-(5H)-phenanthridinone (Phen) with at least one MEK inhibitor.

In some embodiments, the method comprises administering a therapeutically effective amount of a compound selected from the group consisting of N-(6-oxo-5,6-dihydro-phenanthridin-2-yl)-N,N-dimethylacetamide HCl (PJ-34), 4H-thieno[2,3-c]isoquinolin-5-one (Tiq-A) and 6-(5H)-phenanthridinone (Phen) with at least one MEK inhibitor selected from PD184325 (CI-1040), PD0325901, PD98059 and U0126.

In some embodiments, the combination of at least one compound of formula (I) and at least one MEK inhibitor is a combination selected from:
PJ-34 and U0126;
Tiq-A and U0126; and
Phen and U0126.

The present invention is further described in the following examples which are not in any way intended to limit the scope of the invention as claimed.

EXAMPLES

The following materials were used in the below described examples:

Human Breast cancer cell lines MCF-7 and MDA-MB-231, Lung cancer cells (H1299), Pancrease cancer cells (PANC1), Ovary cancer cells (HeyAB and skoV3), Colon cancer cells (DLD1) and leukemia (REH) and the human epithelial cells MCF-10A were from ATCC Co. (American Type Culture Collection, P.O. Box 1549, Manassas, Va. 20108, USA)—ATCC deposit number HTB-22™ obtained via Almog Diagnostic & Medical equipment Ltd. Industrial Area Bd 3 Il-Shoham, 73142 Israel. PJ-34 and Phen were purchased from ALEXIS biochemicals, Cat # ALX-270-289. (Alexis Corporation, Industriestasse 17, CH-4415 Lausen, Switzerland). Tiq-A and 3-AB were purchased from Sigma.

Cells were cultured in 6-wells multi-dish plates (Nunc Denmark). MCF-7 and MDA231 cells were cultured in 6-wells multi-dish plates (Nunc Denmark). MCF-7 and MDA231 cells were maintained in a medium containing DMEM (cat #01055-1A), 10% Horse serum (cat #04-124-1A), 1% L-Glutamine (cat #03-020-1B), and 1% Pen-Strep Ampho (cat #03-033-1B) (Gibco, Invitrogene, purchased from Rhenium, Jerusalem 91035 Israel.

MCF-10A human epithelial cells were cultured in DMEM/F12 (Gibco) with FBS (Gibco) 6%, EGF (100 μg/ml, Cytolab, Rehovot, Israel) 0.02%, Hydrocortisone (50 μM, Sigma) 2.8%, Insulin (10 mg/ml, Sigma) 0.1%, Pen/Strep (Gibco) 1%.

Fibroblasts were prepared from mouse embryos as described by Menssier de Murcia J., et al., (1997) *Proc. Natl. Acad. Sci. USA.* 94, 7303-7307. The fibroblasts were cultured in the same medium as the MCF-7 cells, except for replacement of Horse serum by Fetal Bovine Serum (Biological Industries, Kibbutz Beit HaEmek 25115 Israel, cat #04-121-1A).

Microscope: Inverted fluorescent Olympus 1×51 microscope.

Mice: female CD-1 nu/nu 5-6 weeks old mice (Charles River Labs, Sulzfeld, Germany) were purchased in Israel from Harlan Labs, Jerusalem. The mice were maintained under pathogen-free conditions with access to mouse chow and water ad libitum.

Example 1

Effect of a Single Application of 5, 7.5, 10 and 20 μM PJ-34 on Survival of MCF-7 Cells after 48 Hours FIG. 1 shows MCF-7 cells photographed before treatment (control) and shows that the MCF-7 cancer cells were destroyed within 48 hours after a single application of 5, 7.5, 10 and 20 μM PJ-34, 24 hours after seeding.

Example 2

Figures 1A, 1B:
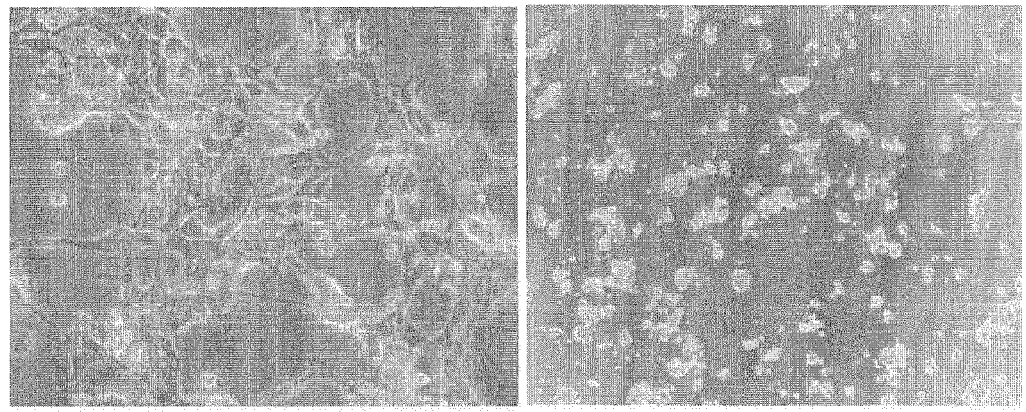
FIGS. 1A, 1C and 1E: MCF-7 breast cancer cells (control).
FIGS. 1B, 1D and 1I: MCF-7 breast cancer cells incubated for 48 hours after single application of PJ-34 (20 μM) 24 hours after seeding.
Figures 1C, 1D:
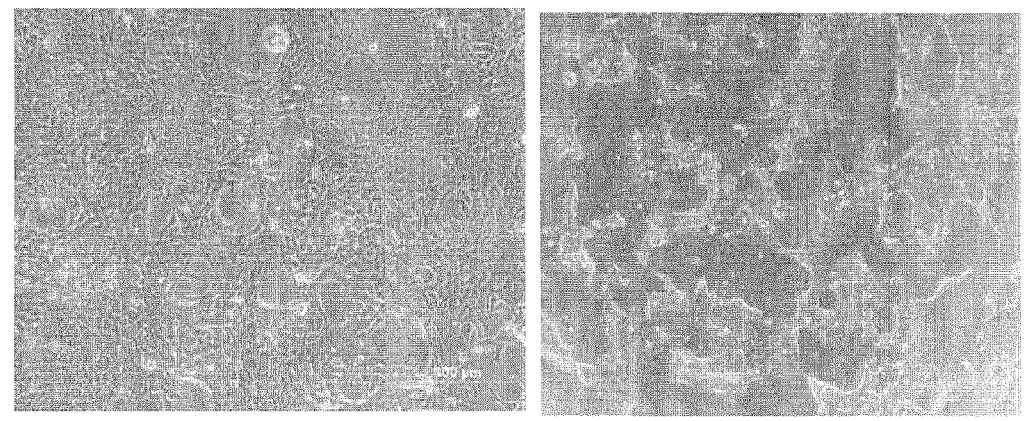
Figure 1E:
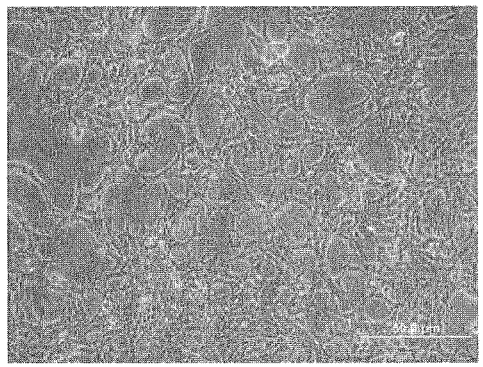
Figure 1F:
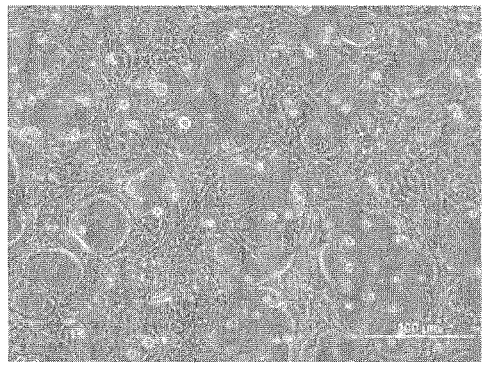
FIG. 1F: MCF-7 breast cancer cells incubated for 48 hours after single application of PJ-34 (5 μM) 24 hours after seeding.
Figure 1G:
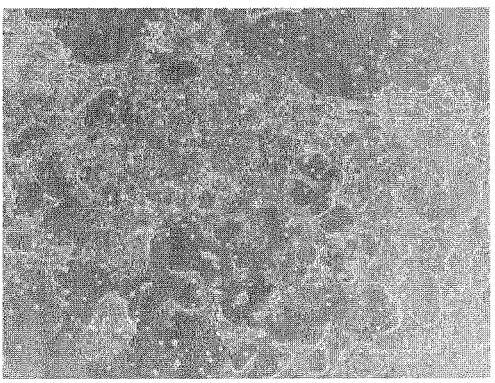
FIG. 1G: MCF-7 breast cancer cells incubated for 48 hours after single application of PJ-34 (7.5 μM) 24 hours after seeding.
Figure 1H:
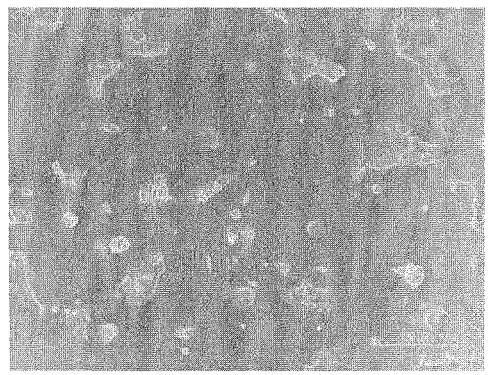
FIG. 1H: MCF-7 breast cancer cells incubated for 48 hours after single application of PJ-34 (10 μM) 24 hours after seeding.
Figure 1I:
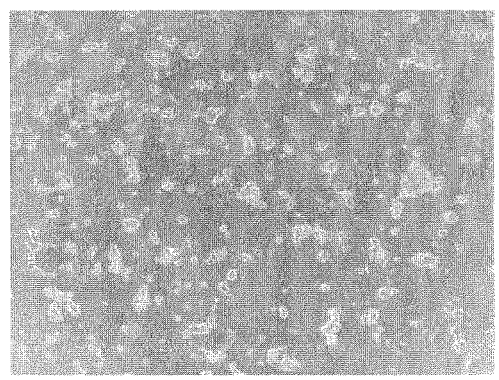
Figure 2:
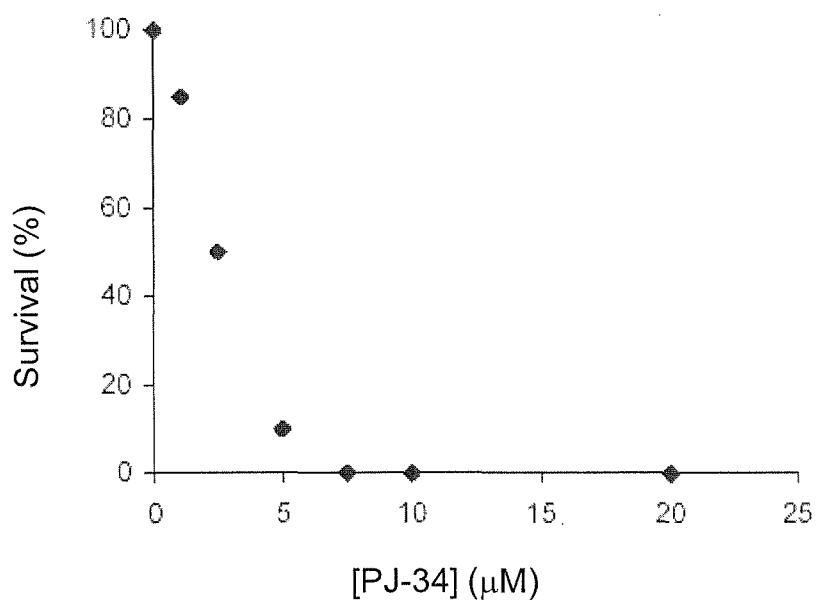
FIG. 2

Effect of PJ-34 at Various Concentrations on Survival of MCF-7 Cells after 48 Hours MCF-7 cells were seeded (about 50,000/well) in 6-well plates. Cultured cells were exposed to PJ-34, 24 hours after seeding by single application of concentrations of 1, 2, 5, 7.5, 10 and 20 μM and incubated for 48 hours (in the medium containing the PJ-34). Cells were counted and pictured under microscope 48 hours after application of PJ-34. FIG. 2 shows that more than 99.5% cell death was measured forty eight hours after the single application of 10-20 μM PJ-34.

Example 3

Effect of PJ-34 at Various Concentrations on Survival of MCF-7 Cells after 2 Weeks in PJ-34 Free Medium MCF-7 cells were seeded (around 50,000/well) in 6-well plates. Cultured cells were exposed to PJ-34 24 hours after seeding at concentrations of 1, 5, and 10 μM. Cells treated by single application with 1, 5 and 10 μM PJ-34 were incubated for 48 hours (in the medium containing the PJ-34) and were re-seeded after the 48 hours at a density of $5–7\times10^4$ in 10 cm plates for colony formation, in PJ-34 free medium. After 2 weeks incubation in PJ-34 free medium without application of PJ-34, cells were fixed (methanol: acetic acid 3:1), stained with crystal violet and counted to determine cells survival.

Figure 3:
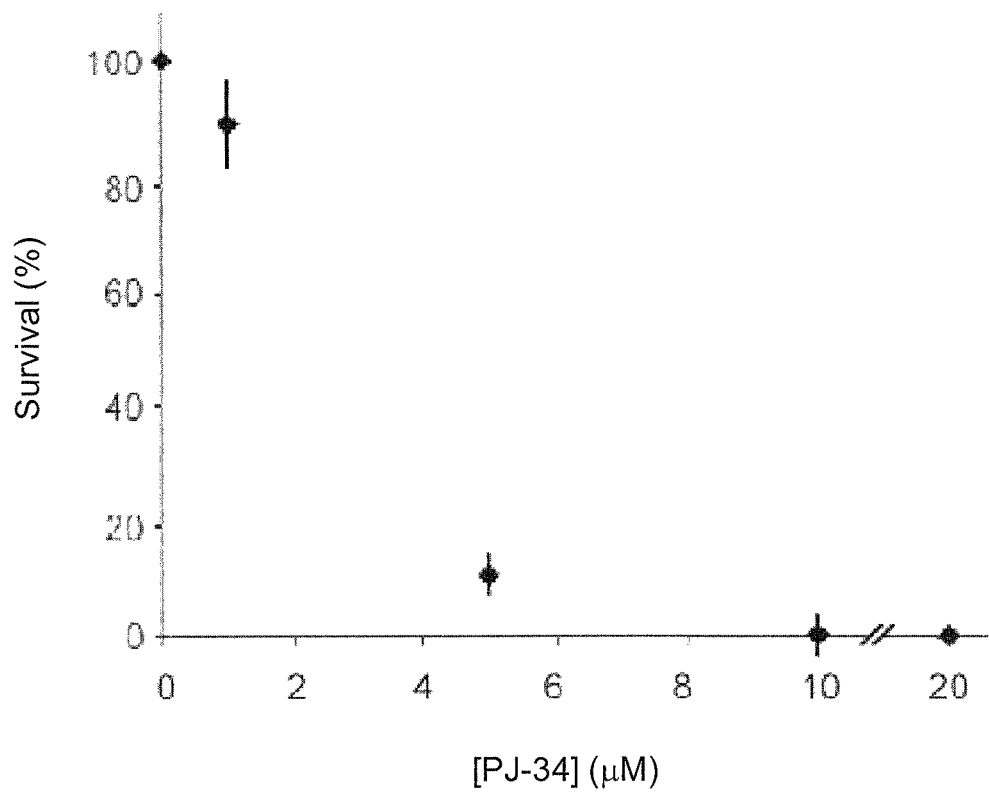

FIG. 3 shows that MCF-7 breast cancer cells treated with 10-20 μM PJ-34 and incubated for 48 hours in PJ-34 containing medium did not recover after two additional weeks of incubation in PJ-34 free medium without any additional application of PJ-34.

Example 4

Effect of PJ-34 on Survival of Non-Malignant Fibroblasts

Mouse fetal fibroblasts (which are not maliganant) were seeded at a density of $5–7\times10^4$ in 3 cm plates. Cultured cells were exposed to a single application of 10 μM PJ-34, 24 hours after seeding and incubated for 48 hours. PJ-34 (10 μM) was applied again 72 hours after seeding and incubated for an additional 100 hours.

Figure 5:
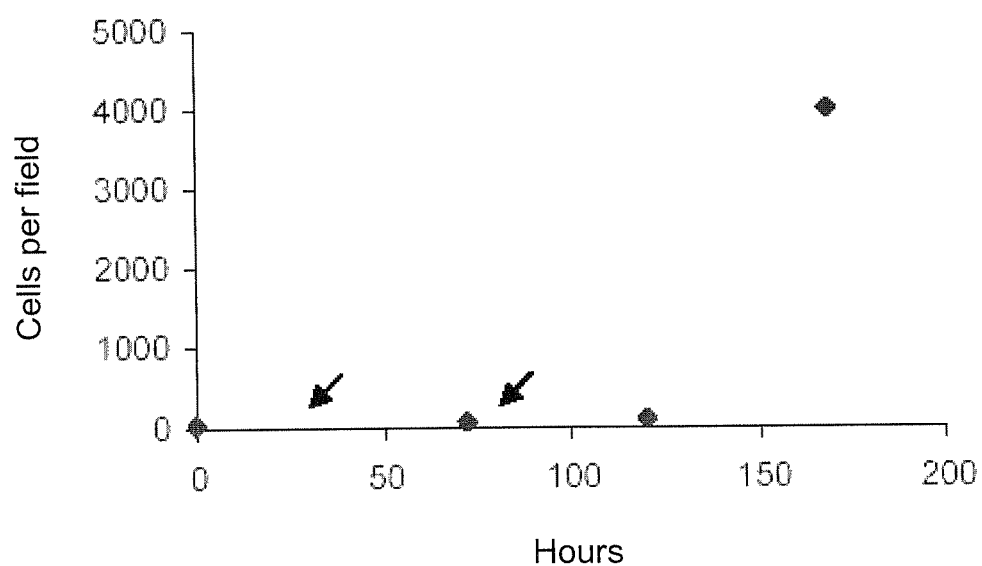

The proliferation of the fibroblasts was retarded (about two-to three fold) in the presence of a total of 20 μM PJ-34. However, within 100 hours in the presence of 20 μM PJ-34 in the medium, cell counts were similar to those of untreated fibroblasts. Thus, FIG. 5 shows that proliferation of mouse fetal fibroblasts was slowed down by repeated applications of 10 μM PJ-34 but also shows that fibroblasts survived the treatment with PJ-34.

FIGS. 4A, 4B and 4C show control fibroblast cell cultures after 12, 72 and 170 hours after seeding respectively; FIG. 4D shows the fibroblasts exposed (24 hours after seeding) to 10 μM PJ-34 after 48 hours of incubation (i.e., photographed 72 hours after seeding). FIG. 4E shows the fully recovered fibroblast proliferation in the presence of a total of 20 μM PJ-34 (an additional 10 μM PJ-34 was added to the medium 72 hours after seeding) in the medium after approximately 100 hours incubation with 20 μM PJ-34 (photographed 170 hours after seeding).

Example 5

Effect of Single Application PJ-34 on Survival of MDA-MB-231 Cells after 2 and 3 Weeks MDA-MB-231 cells were seeded (around 50,000/well) in 6-well plates. Cultured cells were exposed to PJ-34 24 hours after seeding at a concentration of 30 μM. Cells treated by single application with 30 μM PJ-34 were incubated for 48 hours (in the medium containing the PJ-34) and were re-seeded after the 48 hours at a density of $5-7 \times 10^4$ in 6-well dishes, in PJ-34 free medium. After 2 weeks and after 3 weeks incubation in PJ-34 free medium without application of PJ-34, cells were fixed (methanol:acetic acid 3:1), stained with crystal violet and counted to determine cells survival. MDA231 cells did not recover after two and three weeks in the PJ-34 free medium.

Example 6

Effect of PJ-34 on MCF-7 Xenotransplants Developed in Nude Mice

Xenotransplants of MCF-7 were established in six (6) female CD-1 nu/nu 5-6 week old mice.

The mice were injected subcutaneously with $10^7$ MCF-7 cells (injected in 150 μl of MEM and 150 μl of Matrigel Basement Membrane Matrix (Becton Dickinson, Bedford, Mass., USA; In Israel, Bactolab Diagnostics)) to develop xenotransplants.

After 7 weeks, tumors at a size of about 0.7-1 cm were observed in the three mice not treated with PJ-34 (FIG. 6A).

In the other three mice, wherein PJ-34 (2 mM dissolved in 200 μl PBS) was inserted in a subcutaneously implanted Alzet osmotic pump (Biotest. Ltd. P.O. Box 7042, Kfar Saba, Israel 44425) designed to constantly release PJ-34 (at about 10 μM concentration) during 14 days, no visible MCF-7 tumors developed (FIG. 6B).

The treatment with PJ-34 did not affect viability, growth or behavior of the mice for 3 months after the treatment. Mice were sacrificed after 3 months.

Thus, PJ-34 prevented the development of MCF-7 xenotransplants in nude female mice injected with MCF-7 cells.

Example 7

Effect of a Single Application of Tiq-A and Single Application of Phen and a Single Application of 3-AB on Survival of MCF-7 Cells after 48-72 Hours FIG. 7 shows MCF-7 breast cancer control cells 96 hours after seeding, both as is (FIG. 7A) and in medium containing a maximal amount of 0.1% DMSO (FIG. 7B).

FIGS. 8A, 8B and 8C shows photographed MCF-7 breast cancer cells 72 hours after treatment with a single application of 50 μM Tiq-A 24 hours after seeding.

FIGS. 8D, 8E and 8F show photographed MCF-7 breast cancer cells 72 hours after treatment with a single application of 100 μM Tiq-A 24 hours after seeding.

FIG. 9A shows MCF-7 cells photographed 48 hours after treatment with a single application of 25 μM Phen 24 hours after seeding. FIGS. 9B and 9C show MCF-7 cells photographed 72 hours after treatment with a single application of 50 μM Phen 24 hours after seeding.

Figure 10:
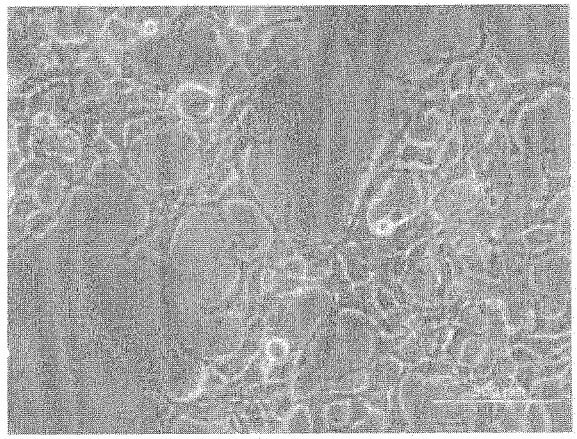

FIG. 10 shows MCF-7 cells photographed 72 hours after treatment with a single application of 1 mM 3-AB (3-aminobenzamide) 1 (not shown) and 24 hours after seeding.

All of PJ-34, Tiq-A and Phen were efficient in killing MCF-7 cells.

Example 8

Effect of PJ-34 on the Development of MCF-7 and MDA-MB-231 Xenotransplants in Nude Female Mice Female CD-1 nu/nu mice are injected subcutaneously with GFP (green fluorescent protein) transfected MCF-7 or MDA-MB-231 cells, which can be traced in the animal by confocal microscopy.

About $10^7$ MCF-7 or MDA-MB-231 cells are injected in 150 μl of MEM (Gibco, Rhenium, Jerusalem Israel) and 150 μl of Matrigel Basement Membrane Matrix (Becton Dickinson, Bedford, Mass., USA; In Israel, Bactolab Diagnostics). Transfection with GFP will enable tracing of the subcutaneous xenotransplants even before tumors are developed. Transfection of MCF-7 and MDA-MB-231 cells with GFP is carried out as described in Caceres et al., 2003 *Luminescence* 18, 218-223.

Nine (9) groups of mice each containing 6 nude female mice (6 weeks old) are implanted with osmotic pumps containing PJ-34 at different periods of time as follows:

Group 1: pump implanted 1 hour after injection with GFP transfected MCF-7 or MDA-MB-231 cells.
Group 2: pump implanted 12 hours after injection with GFP transfected MCF-7 or MDA-MB-231 cells.
Group 3: pump implanted 24 hours after injection with GFP transfected MCF-7 or MDA-MB-231 cells.
Group 4: pump implanted 48 hours after injection with GFP transfected MCF-7 or MDA-MB-231 cells.
Group 5: pump implanted 72 hours after injection with GFP transfected MCF-7 or MDA231 cells.
Group 6: pump implanted 7 days after injection with GFP transfected MCF-7 or MDA-MB-231 cells.
Group 7: pump implanted 14 days after injection with GFP transfected MCF-7 or MDA-MB-231 cells.
Group 8: pump implanted 21 days after injection with GFP transfected MCF-7 cells.
Group 9: pump implanted 30 days after injection with GFP transfected MCF-7 cells.

PJ-34 (2 mM dissolved in 100 μl PBS) is inserted in the subcutaneously implanted Alzet osmotic pump, designed to constantly release PJ-34 (at about 10 μM concentration) during 14 days.

The fluorescence of MCF-7 or MDA-MB-231 cells in the injected and PJ-34 treated mice is monitored by confocal microscopy.

Example 9

Efficiency of PJ-34 Cancer Treatment Using Different Routes of Administration 7 weeks after injection with MCF-7 cells, tumors at a size of about 0.7-1 cm developed in female nude mice that were not treated with PJ-34. Ten (10) days after injection, tumors at a size of 0.5 cm developed in mice that were not treated with PJ-34.

5 groups of mice receive treatment as follows:
a) Two control groups of mice which are not injected with MCF-7 cells, but are treated with PJ-34 (per os, i.v. or by osmotic pump). These mice are tested for their tolerance to PJ-34 and are not sacrificed.
b) Three groups of mice are injected with MCF-7 or MDA-MB-231 cells $10^7$ cells in 150 μl of MEM and 150 μl of matrigel as described above for Example 8. After development of MCF-7 tumors, the effect of PJ-34 on tumor growth is examined during treatment with PJ-34 applied either i.v. (group 2), per os (group 3) or by intratumoral implantation of osmotic pump (group 4). Changes in the size of the MCF-7 or MDA-MB-231 tumors are monitored.

Example 10

Phenanthridine-Derived PARP Inhibitors Efficiently Eradicated MCF-7 and MDA-MB-231 Breast Cancer Cells without Impairing Human Epithelial MCF-10A or Mouse Embryonic Fibroblasts The effect of PARP inhibitors on MCF-7 and MDA-MB-231 human breast cancer cells was examined (cells were seeded in about 500,000 cells/3-mm well in six-well plates). Cells were treated with the potent PARP inhibitors, PJ-34, Tiq-A, and Phen applied only once, 24 hours after seeding. MCF-7 cells did not survive after 48 to 72 hours of incubation with 10 µM PJ-34, nor after incubation with Tiq-A (100 µM) or Phen (50 µM) (FIG. 11A). At these concentrations, PJ-34, Tiq-A, and Phen also inhibit the activity of PARP-1. Significant cell death was observed even at lower concentrations of PJ-34 (FIG. 11B). More than 99% of MCF-7 cells were eradicated after 48 hours of incubation with 10 µM PJ-34 (FIG. 11B). The damage was irreversible. No recovery was observed in MCF-7 cells treated with PJ-34 for 48 to 72 hours and then reseeded in PJ-34-free medium and incubated for 2 additional weeks in the absence of PJ-34 (FIG. 11C). Massive cell death also was observed in MDA231 incubated for 72 to 96 hours with PJ-34 applied only once, 24 hours after seeding. These cells were completely eradicated by incubation with 20-30 µM PJ-34 (FIG. 11D). No recovery was observed in MDA231 cells incubated with 30 µM PJ-34 for 72 hours, after reseeding in PJ-34-free medium and incubation for 2 additional weeks.

Flow cytometry disclosed G2/M arrest and cell death in both MCF-7 and MDA231 cells. G2/M arrest was already observed in both cell types 6 hours after treatment with 10 µM PJ-34. It was not relieved within 120 hours of the experiment and was accompanied by massive cell death (FIG. 12).

Normal dividing cells, human epithelial cells MCF-10A, were similarly arrested at G2/M (FIG. 13A and FIG. 13B). Their arrest also was detected 6 hours after application of PJ-34 (10 µM). However, unlike the malignant cells, MCF10A cells were only temporarily arrested (no arrest observed after 18 hours of incubation with PJ-34), and this transient arrest was not accompanied by cell death (FIG. 13A and FIG. 13B). MCF-10A cells overcame the cell-cycle arrest, and continued to proliferate as normal cells, even when incubated with the same concentrations of PJ-34 and for the same durations used to eradicate MDA-MB-231 cells (compare FIG. 11D and FIG. 13A). Also, proliferation of MCF-10A cells was not significantly reduced, even after a long incubation of 14 days with 10 µM PJ-34 (FIG. 13A).

G2/M cell-cycle arrest also was detected in mouse embryonic fibroblasts (FIG. 14A) after 6 hours of incubation with PJ-34 (10 µM) (FIG. 14B). These cells also overcame the cell-cycle arrest, and the arrest in cell cycle was not accompanied by cell death (FIG. 14B). Thus, treatment with PJ-34 at these concentrations induced a transient G2/M arrest in these normal proliferating cells, which was not accompanied by cell death (FIGS. 13 and 14), whereas the cell cycle of malignant cells MCF-7 and MDA-MB-231 was permanently arrested, and these cells were eradicated by incubation with PJ-34 applied only once 24 hours after seeding (FIGS. 1-3, 11 and 12). An efficient eradication of MCF-7 cells was observed after 48 hours of incubation with 10 µM PJ-34, whereas MDA-MB-231 cells were massively eradicated only after 72 hours of incubation with PJ-34, 20-30 µM. Quiescent cells, brain cortical neurons, and cardiomyocytes were not impaired at all by incubation with the examined phenanthridine-derivatives that also act as PARP inhibitors (10 to 30 µM PJ-34, 100 µM Tiq-A, and 50 µM Phen).

Phenanthridine-derived PARP inhibitors interfered with cell proliferation by causing G2/M arrest in both normal (human epithelial cells MCF10A and mouse embryonic fibroblasts) and human breast cancer cells MCF-7 and MDA-MB-231. However, whereas the normal cells were only transiently arrested, G2/M arrest in the malignant breast cancer cells was permanent and was accompanied by a massive cell death.

Example 11

Effect of PJ-34 on the Development of MC-7 and MDA-MB-231 Xenotransplants

Xenotransplants were developed in female CD-1 nu/nu 5 to 6 weeks old. MCF-7 and MDA 231 cells were injected subcutaneously, about $10^7$ MCF-7 or MDA231 cells in 150 µl of PBS and 150 µl of Martigel Basement Membrane Matrix Becton Dickinson, Bedford, Mass., USA; In Israel Bactolab Diagnostics). In mice treated with PJ-34, injection was adjacent to subcutaneous osmotic pumps dripping PJ-34 by a slow release. The mice were maintained under specific pathogen-free conditions with access to mouse chow and water ad libitum. PJ-34 (2 mM dissolved in 100 µl PBS) was inserted in subcutaneously implanted Alzet osmotic pumps designed to release PJ-34 continuously (at about 0.6 nmol/h) for 14 days. For comparison, in the in vitro experiments, the amount of PJ-34 per dish was approximately 20 nmol. Subcutaneous implantation of these pumps was performed before injection by a veterinarian (Dr. Kastel David). All the experiments with nude mice conform to the Guide for the Care and Use of Laboratory Animals published by the NIH (publication No. 85-23, revised 1996). Approval was granted by the Israeli Ministry of Health ethics review board in the Tel-AvivUniversity (M08033).

Results

PJ-34 Prevented the Development of MCF-7 and MDA-MB-231 Xenotransplants in Nude Female Mice.

In vivo experiments were carried out in nude female mice (nu/nu) injected subcutaneously with MCF-7 or MDA-MB-231 cells (FIG. 15). To test the effect of PJ-34 on the development of xenotransplants in the injected mice, PJ-34 (2 mM dissolved in 100 µl PBS) was inserted into subcutaneously implanted osmotic pumps (Alzet) that enable its constant slow release for 14 days. In the control nude mice, pumps contained only PBS, or pumps were not implanted. Each mouse was injected subcutaneously with approximately $10^7$ MCF-7 or MDA-MB-231 cells dispersed in Matrigel. Tumors developed within 6 to 7 weeks in the control mice injected with MCF-7 cells and within 10 days in the control mice injected with MDA231 cells. One mouse died 3 weeks after being injected with MDA-MB-231 cells. In contrast, no visible tumors developed in the PJ-34-treated mice during 4 months after injection of MCF-7 cells and during the 10 weeks after injection with MDA-MB-231 cells (FIGS. 15A and 15B). Importantly, the 14-day treatment with a slow release of PJ-34 did not affect the vitality, growth, development, or any other behavior of the treated mice during the follow-up periods.

After 10 weeks, we detected tumors in two of the five mice that were injected with MDA-MB-231 cells and treated with PJ-34. These tumors were of human origin, as indicated by histochemistry (labeling with mouse anti-human mitochondria antibody (Millipore/Biotest) applied after blocking ("mouse-on-mouse"; Vector Labs/Zotal)). The other 3 mice that were treated with PJ-34 survived for more than 4 months, and continued growing similarly to the untreated and un-injected mice.

Tumor-free survival curves for mice injected with MCF-7 cells and for mice injected with MDA-MB-231 cells are presented in FIG. 15C. The effect of treatment with PJ-34 on tumor-free survival is indicated, and significance was calculated with the log-rank significance test. The significance was P=0.0253 for mice injected with MCF-7 cells, and P=0.023 for mice injected with MDA-MB-231 cells.

Example 12

The Effect of PJ-34 on Human Colon Cancer DLD1 Cells

Human colon cancer DLD1 cells (seeded about 50,000 cells/3-mm well in 6-well plates) were incubated, as detailed in Example 10, with PJ-34 for 96 hours applied only once, 24 hours after seeding.

The cancer cells were completely eradicated by incubation with 20 μM PJ-34 compared to the untreated cells (control) (FIG. 16).

Example 13

The Effect of PJ-34 on Human Lung Cancer Cells H1299

The cells (seeded about 50,000 cells/3-mm well in 6-well plates) were incubated, as detailed in Example 10, with PJ-34 for 96 hours applied only once, 24 hours after seeding.

The cancer cells were completely eradicated by incubation with 20 μM PJ-34 compare to the untreated cells (control) (FIG. 17).

Example 14

The Effect of PJ-34 on Pancreatic Cancer Cells, PANC1

The cells (seeded about 50,000 cells/3-mm well in 6-well plates) were incubated, as detailed in Example 10, with PJ-34 for 96 hours applied only once, 24 hours after seeding.

The cells were completely eradicated by incubation with 20 μM μM PJ-34 compare to the untreated cells (control) (FIG. 18).

Example 15

The Effect of PJ-34 on Ovarian Cancer HeyAB Cells

The cells (seeded about 50,000 cells/3-mm well in 6-well plates) were incubated, as detailed in Example 10, with PJ-34 for 96 hours applied only once, 24 hours after seeding.

The cells were completely eradicated by incubation with 20 μM PJ-34 compare to the untreated cells (control) (FIG. 19).

Example 16

The Effect of PJ-34 on Lymphoid Leukemia REH Cells

The cells (seeded about 50,000 cells/3-mm well in 6-well plates) were incubated, as detailed in Example 10, with PJ-34 for 96 hours applied only once, 24 hours after seeding.

The cells were completely eradicated by incubation with 20 μM PJ-34 compare to the untreated cells (control) (FIG. 20).

Example 17

Efficiency of the Combination of MEK and PARP Inhibitors on Eradication of Human Breast Cancer Cells (a Synergistic Effect)

HCC1937 (triple negative, BRCA deficient) human breast cancer cells (seeded about 50,000 cells/3-mm well in 6-well plates were incubated with PJ-34 and U0126 for 48 hours applied only once, 24 hours after seeding (FIGS. 21A-H).

Figure 21A:
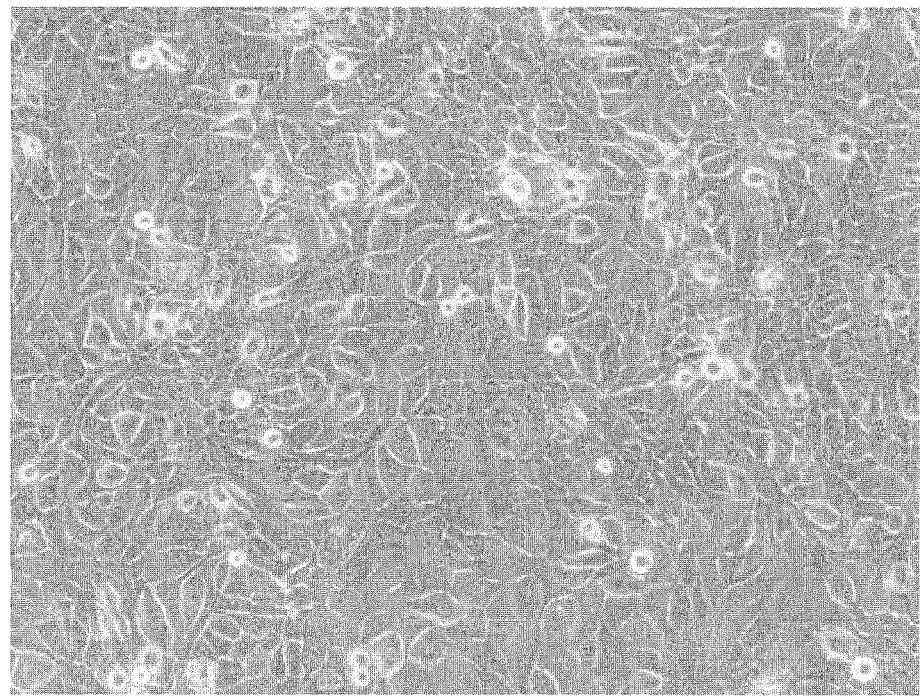

FIG. 21A shows untreated cells 72 hours after seeding (control).

Figure 21B:
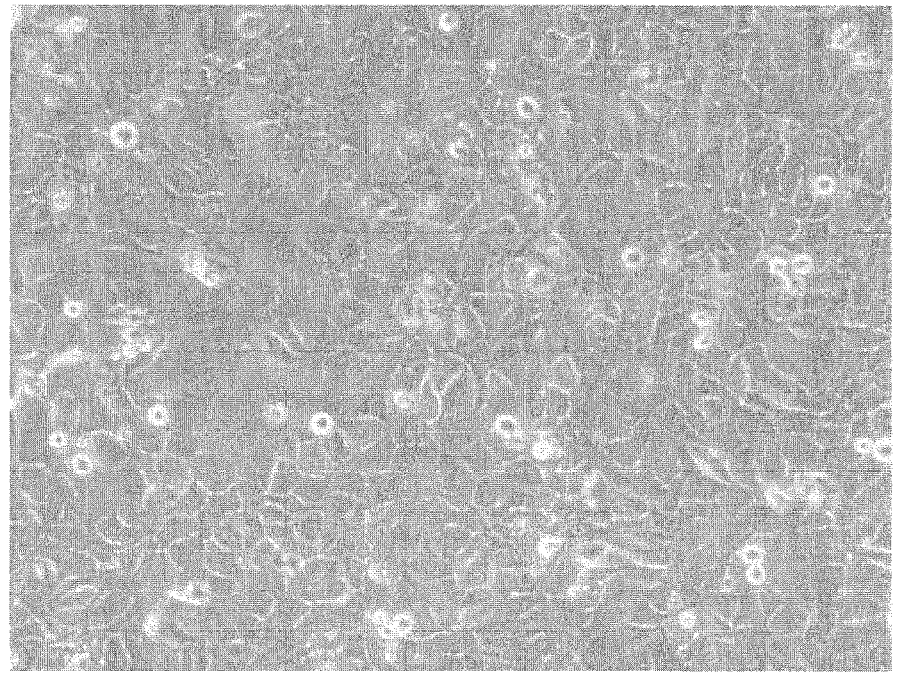

FIG. 21B shows cells which were incubated with single application of 5 μM MEK inhibitor, U0126.

Figure 21C:
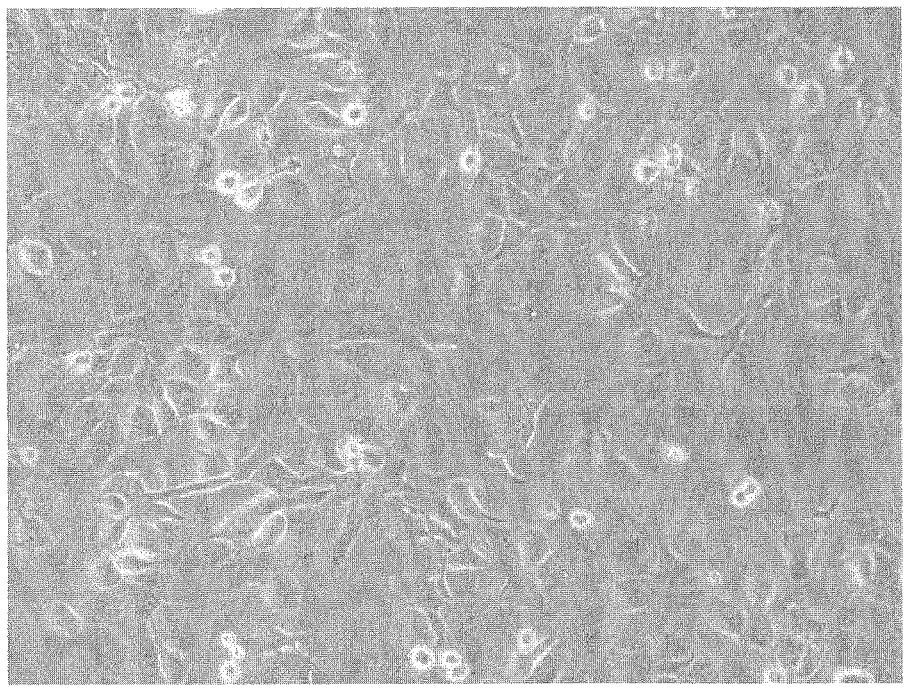

FIG. 21C shows cells which were incubated with single application of 10 μM MEK inhibitor, U0126.

Figure 21D:
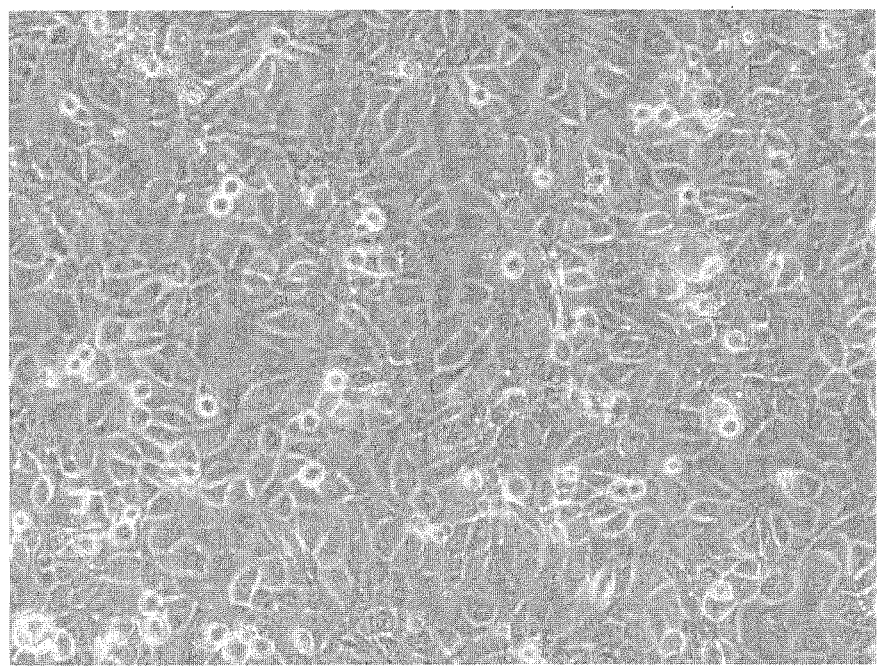

FIG. 21D shows cells which were incubated with single application of 5 μM PJ-34.

Figure 21E:
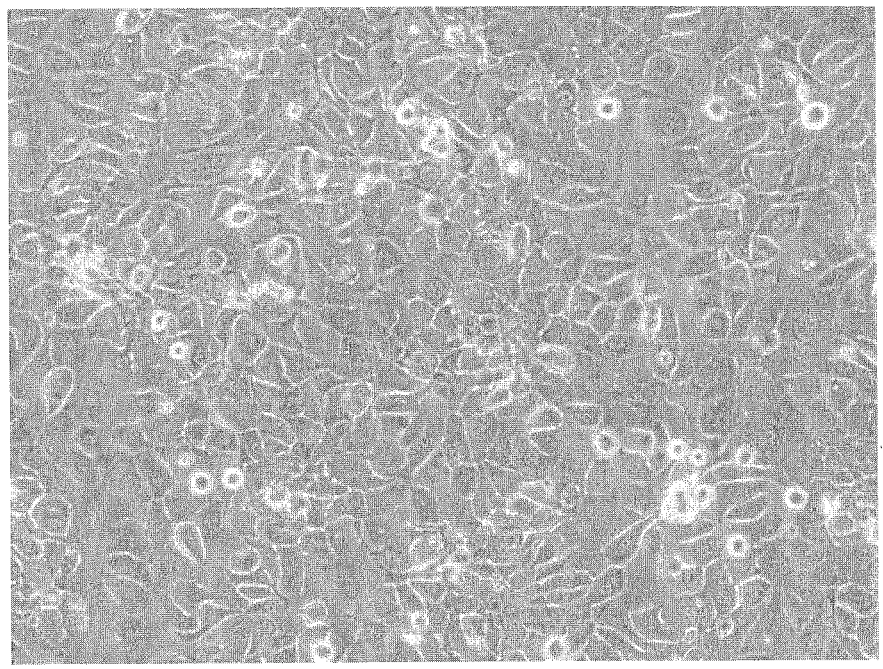

FIG. 21E shows cells which were incubated with single application of 10 μM PJ-34.

Figure 21F:
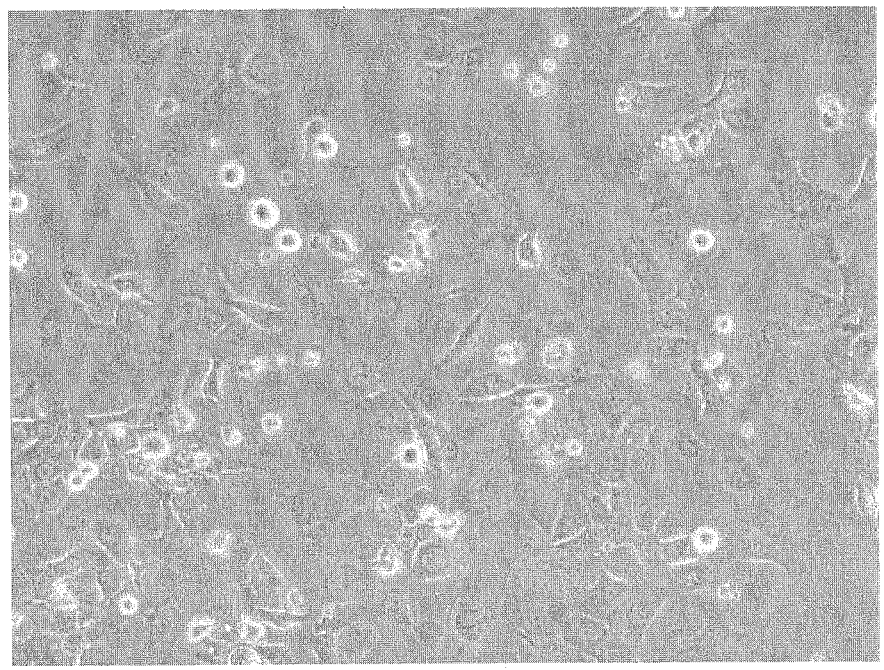

FIG. 21F shows cells which were incubated with 5 μM PJ-34 and 5 μM U0126.

Figure 21G:
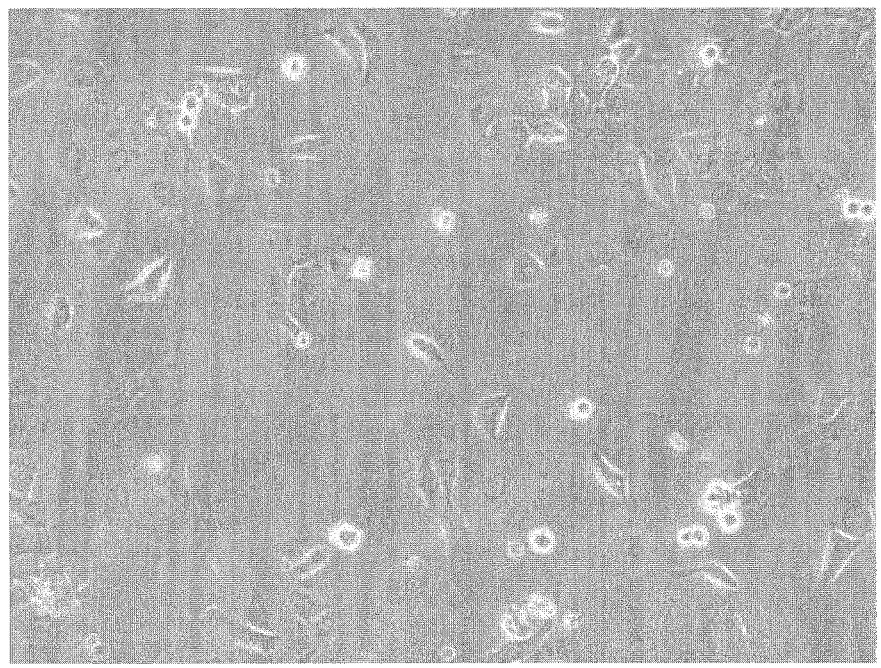

FIG. 21G shows cells which were incubated with 10 μM PJ-34 and 5 μM U0126.

Figure 21H:
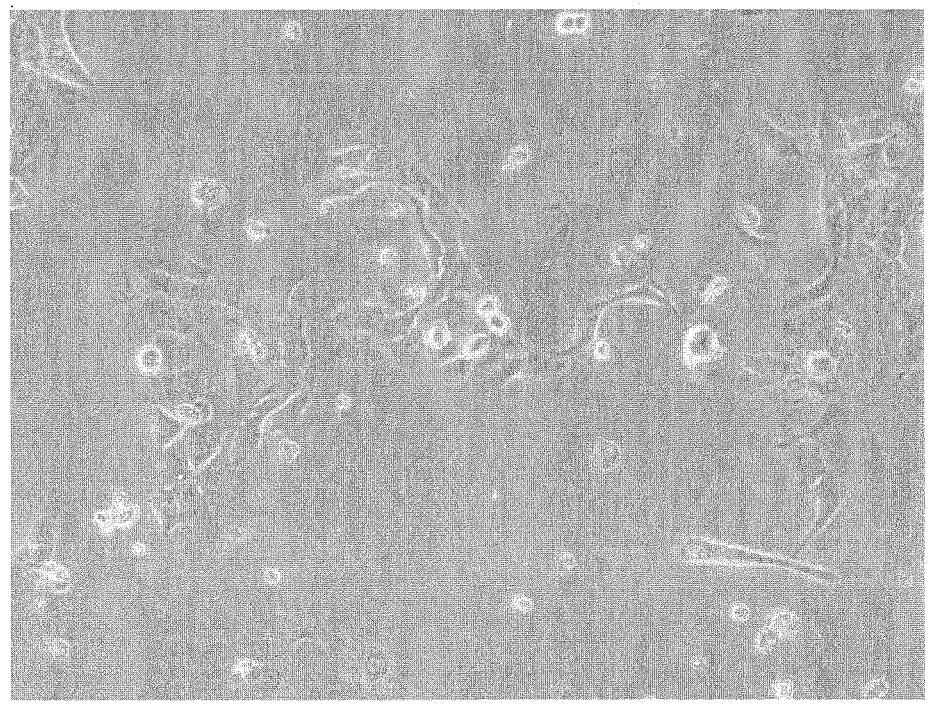

FIG. 21H shows cells which were incubated with 50 μM Tiq-A and 5 μM U0126.

A synergistic effect between the MEK inhibitor U0126 and the phenanthridine derivatives PJ-34 and Tiq-A that also act as PARP inhibitors was observed compare to the effect of each of these inhibitors alone.

Example 18

A Comparison Between the Efficiency of PJ-34 and Other PARP-1 Inhibitors for Eradication of Breast Cancer MDA-MB-231 Cells in a Cell Culture FIG. 22 shows the cytotoxicity of various PARP1 inhibitors in MDA-MB-231 breast cancer cells. Survival rate (percentage relative to untreated cells, control) of MDA-MB-231 breast cancer cells after 72 hours of incubation with PJ-34 (Ki=30 nM) or any of the more potent PARP-1 inhibitors, ABT888 (Ki=5.2 nM), AG14361 (Ki<5 nM), BSI-201 (irreversible inhibitor of PARP-1 binding to DNA), each of them applied 24 hours after seeding at the indicated concentrations. Each value is an average value of three measurements obtained in three different experiments.

When PJ-34 was compared to other potent PARP-1 inhibitors, the cytotoxicity of PJ-34 was higher (i.e., lower % survival) in cancer cells (MDA-MB-231) that were treated with 10-30 μM PJ-34 (0.4-1% survival) as compared to the same type of cells that were treated with other known potent PARP1 inhibitors ABT888, BSI-201 and AG-14361 (above 95% survival).

Example 19

PJ-34 is Cytotoxic to Parp-1$^{-/-}$ Mouse Embryonic Fibroblasts (MEF)

MEF were incubated 72 hours with PJ-34 at the indicated concentrations. The fraction of cells with multi-focal spindles in PJ-34 treated MEF (Parp-1$^{+/+}$ (black line) and Parp-1$^{-/-}$ (grey line)) is indicated. FIG. 23B: The survival of Parp-1$^{-/-}$ MEF and Parp-1$^{+/+}$ MEF incubated 72 hours with PJ-34 at the indicated concentrations, relative to the survival of control untreated MEF (Parp-1$^{+/+}$ (black line) and Parp-1$^{-/-}$ (grey line)). Cell survival was measured by luminescent detection of ATP production in the cells. Parp-1$^{-/-}$ cells were more eradicated by PJ-34. The mean values of 4 measurements for each cell line in 3 different experiments are indicated.

Acting as extra-centrosomes declustering agent PJ-34 dose dependently caused un-clustered centrosomes (labeled by γ-tubulin), distorted spindles (microtubules labeled by α-tubulin) and cell death in Parp1($^{-/-}$) cells despite their Parp1 deficiency. Normal MEF were hardly affected by PJ-34.

The fact that PJ-34 eradicates PARP(−/−) MEF cells, and causes multipolar spindles in these multi-centrosomal cells even in the absence of PARP1, supports the argument that PJ-34 induces cell death in multi-centrosomal cells in a PARP1 independent mechanism.

Example 20

Post Translational Modification of HSET in MDA-MB-231 Breast Cancer Cells

FIG. 24A shows several phosphorylation sites which may be involved in post-translational modifications of HSET.

FIG. 24B-I and II the effect of PJ-34, Tiq-A and Phen on the post translational modifications of HSET was demonstrated by measuring changes in the pI (isoelectric point) of the protein (2-D gel electrophoresis).

Post translational modifications of HSET in MDA-MB-231 breast cancer cells (FIG. 24B-I) were measured by the shifts in its isoelectric point (pI). PJ-34, Tiq-A and to a lesser extent Phen(6) prevent the post translational modification of HSET in MDA-MB-231 cancer cells (pI shifts from about pH8 to about pH6). In contrast, the potent PARP1 inhibitor ABT888, at concentration 5-20 μM did not affect the post translational modification of HSET. Also, HSET is not modified in normal epithelial cells MCF10A. The vertical lines mark the point of loading of the proteins including HSET in the cell extracts. The arrows mark the shifted pI of HSET. In untreated MDA-MB-231 cells, the largest shift in pI of HSET was to pH 5.6 in the untreated MDA-MB-231 cells. FIG. 24B-II shows that the pI of HSET in MCF10A cells was not shifted and the pI of this basic protein HSET was between 9 and 10 pH, and was not changed in MDA-MB-231 cells treated with PJ-34.

This analysis disclosed several HSET modifications indicated by several shifts in its pI. PJ-34, Tiq-A and Phen prevented some of HSET modifications, In contrast the PARP1 inhibitor ABT888 did not interfere with the post translational modifications of HSET. The shifts in the pI of HSET indicating its post-translational modifications in MDA-MB-231 cells treated with ABT-888 was similar to the shifts in pI in control untreated cells (FIG. 3B). The shift in the pI of HSET in the cancer cells indicates modification of HSET by negative charges added to the protein, e.g., phosphorylation (FIG. 24A).

Example 21

PJ-34, Tiq-A and Phen interfere with the binding of kinesin-14/HSET to γ-tubulin Treatment of MDA-MB-231 human breast cancer cells with PJ-34 (20 μM) Tiq-A (100 μM) and Phen(6) (50 μM) (48 hours) interfered with the binding of γ-tubulin to kinesin-14/HSET. ABT-888, a non-phenanthrene potent PARP1 inhibitor, did not affect the binding of γ-tubulin to HSET.

FIG. 25 shows that preventing HSET post-translational modifications correlated with down-regulation of its binding to γ-tubulin. Thus, PJ-34, Tiq-A and Phen interfered with the co-immunoprecipitation of HSET with γ-tubulin.

In contrast, ABT888 did not interfere with the binding of HSET to γ-tubulin, as it did not interfere with the modification of HSET (FIGS. 24B and 25).

The impaired binding of un-modified HSET to γ-tubulin (FIG. 25) may be involved in the activity of PJ-34 Tiq-A and Phen as centrosomes de-clustering agents.

Example 22

Co-Localization of γ-Tubulin and Tankyrase1 in MDA-MB-231 Cells

FIG. 26 shows that the co-localization of tankyrase1 and γ-tubulin (in the centrosomes) in the spindle poles of MDA-MB-231 breast cancer cells is distorted by PJ-34 applied once, 24 hours after seeding. Cells were incubated with PJ-34 (20 μM) for 48 hours. Un-clustered centrosomes co-localize with tankyrase-1. Abnormal arrangement of chromosomes (labeled by DAPI) in the spindle of MDA-MB-231 cells treated with PJ-34, were observed which prevented their normal mitosis.

FIG. 27 shows that PJ-34 does not interfere with the binding of tankyrase1 with γ-tubulin.

PJ-34 does not interfere with the binding of tankyrase1 to γ-tubulin in the multi-centrosomal cells MDA-MB-231 (FIGS. 26 and 27). Moreover, in cells treated with PJ-34, the centrosomes are apparently anchored to tankyrase1 (via binding of tankyrase1 to γ-tubulin; FIG. 26) in many foci, even outside the spindle poles (FIG. 26). This suggests that the treatment with PJ-34 causes clusters of γ-tubulin bound to tankyrase1 (possibly indicating centrosomes clusters on polymers of tankyrase1) promoting centrosomes de-clustering outside the spindle poles in the presence of PJ-34.

FIG. 28 shows that PJ-34 (but not ABT-888) exclusively interferes with the co-immunoprecipitation of α-tubulin with γ-tubulin in cancer cells.

Thus, the combined effects on HSET and tankyrase1 and the reduced binding of α-tubulin (in the microtubules) to γ-tubulin (in the centrosomes) in the presence of PJ-34, but not ABT888 are consistent with multifocal spindles and scattered centrosomes in multi-centrosomal cancer cells treated with PJ-34.

Example 23

FIG. 29-FIG. 31 Show Erradication of the Malignant U-87 Glioblastoma (Brain Cancer) Cells Treated with PJ-34, Phen and Tiq-A FIG. 29A—U-87 Glioblastoma cells treated with PJ-34 for 72 h.

FIG. 29B—U-87 Glioblastoma cells treated with PJ-34 for 96 h.

FIG. 30—U-87 Glioblastoma cells treated with Phen for 96 h.

FIG. 31—U-87 Glioblastoma cells treated with Tiq-A for 96 h.

The malignant U-87 Glioblastoma cells were incubated with these molecules applied once 24 hours after seeding. Cell viability was measured by FACS. The results of 3 different experiments carried in duplicates are presented.

Glioblastoma U-87 cells were incubated for 72 and 96 hours after a single application of PJ-34 and for 96 hours after a single application of Phen or Tiq-A, at a concentration of 0, 0.5, 1, 10, 20 and 30 µM applied 24 hours after seeding.

As presented in FIGS. 29-31, PJ-34, Tiq-A and Phen all were cytotoxic in glioblastoma cancer cells at high concentrations, much higher than the concentrations that inhibit the activity of PARP1 (e.g. EC50 for PJ-34 20 nM, for Phen 120 nM and for Tiq-A 450 nM). The supplemental experimental results presented here further supports the conclusion that the correlation observed so far amongst PJ-34, Tiq-A and Phen would lead one of ordinary skill in the art to reasonably expect that this close correlation would also hold for other specific cancer cells tested with PJ-34.

Example 24

Efficiency of PJ-34 in Cancer Treatment Using Intra-Peritoneal Route of Administration In vivo experiments were carried out in nude female mice (nu/nu) injected subcutaneously with MDA-MB-231 cells (FIG. 32).

To test the effect of PJ-34 on the development of xenotransplants in the injected mice, female CD-1 nu/nu mice (Harlan, Israel) were injected subcutaneously with MDA-MB-231 cells. About $10^6$ cells were injected in 100 µl of MEM (Gibco, Rhenium, Jerusalem Israel) and 100 µl of Matrigel Basement Membrane Matrix (Becton Dickinson, Bedford, Mass., USA; In Israel, Bactolab Diagnostics).

Two weeks after injection with MDA-MB-231 cells, palpable (50-80 mm$^3$) tumors developed in all the female nude mice. One pair of mice remained un-treated. The other pair was injected i.p (intra-peritoneal) daily for 14 days with 50 mg/kg PJ-34 (Alexis Biochemicals/Enzo Life Sciences). PJ-34 was dissolved in 100 microL saline. Tumors' size was measured every day in all the mice (both treated and untreated). The treated mice were photographed on the first day and on the last day of treatment. Tumor sizes were 750 mm$^3$ and 850 mm$^3$ in the untreated mice, versus 130 mm$^3$ and 150 mm$^3$ in the treated mice.

FIGS. 32A-D: treatment with PJ-34 prevented development of MDA-MB-231 xenotransplants in nude mice (untreated—FIG. 32A, treatad—FIG. 32B and FIG. 32C. FIG. 32D: tumor progression in female nude mice after subcutaneous injection of human MDA231 cells in the absence or presence of treatment with PJ-34.

The invention claimed is:

1. A method for the treatment of cancer in a subject, said method comprising orally administering to said subject an amount of a compound selected from the group consisting of N-(6-oxo-5,6-dihydro-phenanthridin-2-yl)-N,N-dimethylacetamide (PJ-34), 6-(5H)-phenanthridinone (Phen) and any pharmaceutically acceptable salt of any of said compounds, wherein the compound is administered in an amount of 30 mg/kg body weight/day to 120 mg/kg body weight/day and has a lethal effect on the cells of said cancer, and wherein said cancer is selected from the group consisting of breast cancer, lung cancer, pancreatic cancer, ovarian cancer, colon cancer, glioblastoma and leukemia.

2. The method according to claim 1, wherein the amount of said compound is selected from the group consisting of between 30 mg/kg body weight/day and 100 mg/kg body weight/day, between 30 mg/kg body weight/day and 90 mg/kg body weight/day, between 30 mg/kg body weight/day and 80 mg/kg body weight/day, between 30 mg/kg body weight/day and 70 mg/kg body weight/day, between 30 mg/kg body weight/day and 60 mg/kg body weight/day, between 30 mg/kg body weight/day and 50 mg/kg body weight/day, between 30 mg/kg body weight/day and 40 mg/kg body weight/day, between 40 mg/kg body weight/day and 120 mg/kg body weight/day, between 50 mg/kg body weight/day and 120 mg/kg body weight/day, between 60 mg/kg body weight/day and 120 mg/kg body weight/day, between 70 mg/kg body weight/day and 120 mg/kg body weight/day, between 80 mg/kg body weight/day and 120 mg/kg body weight/day, between 90 mg/kg body weight/day and 120 mg/kg body weight/day, between 100 mg/kg body weight/day and 120 mg/kg body weight/day, between 110 mg/kg body weight/day and 120 mg/kg body weight/day, between 50 mg/kg body weight/day and 80 mg/kg body weight/day, and between 50 mg/kg body weight/day and 60 mg/kg body weight/day.

3. The method according to claim 1, wherein the amount of said compound is selected from 30 mg/kg body weight/day, 40 mg/kg body weight/day, 50 mg/kg body weight/day, 60 mg/kg body weight/day, 70 mg/kg body weight/day and 80 mg/kg body weight/day.

4. The method according to claim 1, wherein the compound is PJ-34 or any pharmaceutically acceptable salt thereof.

5. The method according to claim 1, wherein said cancer is breast cancer.

6. The method according to claim 1, wherein the compound is administered in an amount between 30 mg/kg body weight/day and 100 mg/kg body weight/day.

7. The method according to claim 1, wherein the cancer is glioblastoma.

8. A method for the treatment of cancer in a subject, said method comprising intravenously administering to said subject an amount of a compound selected from the group consisting of N-(6-oxo-5,6-dihydro-phenanthridin-2-yl)-N, N-dimethylacetamide (PJ-34), 6-(5H)-phenanthridinone (Phen) and any pharmaceutically acceptable salt of any of said compounds, wherein the compound is administered in an amount of 1 mg/kg body weight/day to 20 mg/kg body weight/day and has a lethal effect on the cells of said cancer, and wherein said cancer is selected from the group consisting of breast cancer, lung cancer, pancreatic cancer, ovarian cancer, colon cancer, glioblastoma and leukemia.

9. The method according to claim 8, wherein the compound is N-(6-oxo-5,6-dihydro-phenanthridin-2-yl)-N,N-dimethylacetamide (PJ-34) or any pharmaceutically acceptable salt thereof.

* * * * *